(12) United States Patent
Moloney et al.

(10) Patent No.: US 8,530,212 B2
(45) Date of Patent: Sep. 10, 2013

(54) CARBENE PRECURSOR COMPOUND FOR PRODUCING AN ADHESIVE SURFACE ON A SUBSTRATE

(75) Inventors: Mark Moloney, Oxford (GB); Jon-Paul Griffiths, Yarnton (GB)

(73) Assignee: ISIS Innovation Limited, Summertown, Oxford (GB)

( * ) Notice: Subject to any disclaimer, the term of this patent is extended or adjusted under 35 U.S.C. 154(b) by 961 days.

(21) Appl. No.: 12/377,487

(22) PCT Filed: Aug. 22, 2007

(86) PCT No.: PCT/GB2007/003194
§ 371 (c)(1),
(2), (4) Date: Nov. 23, 2009

(87) PCT Pub. No.: WO2008/023170
PCT Pub. Date: Feb. 28, 2008

(65) Prior Publication Data
US 2010/0068783 A1    Mar. 18, 2010

(30) Foreign Application Priority Data
Aug. 23, 2006    (GB) .................................. 0616724.1

(51) Int. Cl.
C12N 11/08    (2006.01)
C12N 11/06    (2006.01)
C07K 17/08    (2006.01)
C08L 89/00    (2006.01)
C07K 17/06    (2006.01)

(52) U.S. Cl.
USPC ........... 435/180; 435/181; 525/54.1; 530/402

(58) Field of Classification Search
None
See application file for complete search history.

(56) References Cited

U.S. PATENT DOCUMENTS

| | | | |
|---|---|---|---|
| 2,710,862 A | 6/1955 | Schroeder et al. | |
| 3,376,278 A | 4/1968 | Wayne et al. | |
| 4,280,819 A | 7/1981 | Hartle et al. | |
| 4,309,453 A | 1/1982 | Reiner et al. | |
| 5,002,582 A | 3/1991 | Guire et al. | |
| 5,075,427 A | 12/1991 | Kang et al. | |
| 5,154,808 A | 10/1992 | Miyasaka et al. | |
| 5,490,983 A | 2/1996 | Worley et al. | |
| 6,060,046 A | 5/2000 | Steinberg et al. | |
| 6,110,936 A | 8/2000 | Gravestock | |
| 6,699,527 B1 | 3/2004 | Moloney et al. | |
| 7,034,129 B2 | 4/2006 | Moloney et al. | |
| 7,939,581 B2 * | 5/2011 | Moloney et al. .............. | 523/122 |
| 2003/0186448 A1 | 10/2003 | Bourget et al. | |
| 2008/0146731 A1 | 6/2008 | Moloney et al. | |

FOREIGN PATENT DOCUMENTS

| | | |
|---|---|---|
| CA | 812736 | 5/1969 |
| CN | 1518536 | 8/2004 |
| EP | 0 014 843 A2 | 1/1980 |
| EP | 0 177 248 | 4/1986 |
| EP | 0 425 485 B1 | 10/2000 |
| FR | 1 500 512 | 11/1967 |
| GB | 2 013 201 A | 8/1979 |
| WO | WO 95/19949 | 7/1995 |
| WO | WO 96/01294 | 1/1996 |
| WO | WO 99/01514 | 1/1999 |
| WO | 00/26180 | 5/2000 |
| WO | 02/32590 | 4/2002 |
| WO | 2005/028423 | 3/2005 |
| WO | 2006/075183 | 7/2006 |

OTHER PUBLICATIONS

Journal of Organic Chemistry, 1990, vol. 55(8), pp. 2325-2332 & Chemical Abstracts, abstr. No. 112:178564.
Nippon Kagaku Kaishi, 1989, vol. (8), pp. 1431-1439 & Chemical Abstracts, abstr. No. 112:118034.
Tetrahedron, 1985,vol. (8), pp. 1435-1440 & Chemical Abstracts, abstr. No. 103:141146.
Tetrahedron, 1994, vol. 50(12), pp. 3785-3796 & Chemical Abstracts, Abstr. No. 121:41146.
Chemical Abstracts, abstr. No. 109:230881 & Journal of Heterocyclic Chemistry, 1988, vol. 25(2), pp. 447-452.
Vorotnikov, A.P. et al., Khim. Fiz. (1991) 10(11), 1475-9; & Chemical Abstracts vol. 116, No. 3, Jan. 20, 1992, abstract No. 20575.
D. R. Braybrook et al., J. Photochem. Photobid A: Chem, 1993, 70, 171.
D.D. Tanner et al., J. Org.Chem., 1980, 45, 5177.
S. Hünig et al, Eur. J. Org. Chem., 2002, 10, 1603-1613.
Reactive & Functional Polymers, 2000, 45, 137-144.
D. Davies, Nature, 2003, 2, 114.
J.C. Tiller et al., PNAS, 2001, 98, 5981.

(Continued)

*Primary Examiner* — David M Naff
(74) *Attorney, Agent, or Firm* — Nixon & Vanderhye P.C.

(57) ABSTRACT

A process for producing a substrate having an adhesive surface, which process comprises: (a) contacting the substrate with a carbene precursor, which carbene precursor is a compound of the following formula (1): whose substituent groups are defined herein, provided that when R is aryl or heteroaryl, said aryl or heteroaryl may be substituted by one, two, three, four or five groups, which groups are independently selected from various groups including -$L_B$-$W_B$; and (b) either: (i) when $W_A$ or $W_B$ comprises an adhesive functional group, generating a carbene reactive intermediate from the carbene precursor so that it reacts with the substrate to functionalise the surface, thereby yielding said substrate having an adhesive surface; or (ii) when $W_A$ or $W_B$ comprises a group which is a precursor of an adhesive functional group, generating a carbene reactive intermediate from the carbene precursor so that it reacts with the substrate to functionalise the surface, and (c) converting said group which is a precursor into an adhesive functional group thereby yielding said substrate having an adhesive surface. The invention further relates to carbene precursor compounds for use in the process, substrates produced by the process and to processes for preparing certain precursor compounds.

(I)

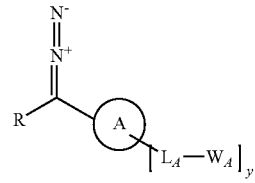

21 Claims, 1 Drawing Sheet

(56) References Cited

OTHER PUBLICATIONS

M. W. Eknoian and S. D. Worley, *Journal of Bioactive and Compatible Polymers*, 1998, 13, 303.
D. B. Elrod and S. D. Worley, *Journal of Bioactive and Compatible Polymers*, 1999, 14, 258.
G. Sun, L. C. Allen, E. P. Luckie, W. B. Wheatley, and S. D. Worley, *Industrial & Engineering Chemistry Research*, 1995, 34, 4106.
S. D. Worley and G. Sun, *Trends in Polymer Science*, 1996, 4, 364.
Y. Makioka, S. -Y Uebori, M. TsurLo,Y. Taniguchi, K. Takaki, andY. Fujiwara, *J.Org.Chem.*, 1996, 61, 372.
G. Sun and X. Xu, *Textile Chemist and Colorist*, 1998, 30, 26.
G. Sun and J.F. Williams, *Chemistry & Industry*, 1999, 658.
G. Sun and X. Xu, *Textile Chemist and Colorist*, 1999, 31, 31.
S. V. Sunthankar, R. Gopalan, and A. B. Vayla, *Ind. J. Chem.*, 1973, 11, 503.63.
*Journal of Environmental Health*, 1998, 60, 47.
H. Carlsohn, U. C. Hipler, A. Breuer, A. Schutz, H. Schutz, and M. Hartmann, *Pharmazie*, 1983, 38, 823.
J. Hazziza-Laskar, N. Nurdin, G. Helary, and G. Sauvet, Journal of Applied Polymer Science, 1993, 50, 651.
J. Hazziza-Laskar, G. Helary, and G. Sauvet , *Journal of Applied Polymer Science*, 1995, 58, 77.
J. Kizlink, A. Fargasova, and L. Reinprecht, *Drevarsky Vyskum*, 1996, 41, 19.
N. Nurdin, G. Helary, and G. Sauvet, *Journal of Applied Polymer Science*, 1993, 50, 663.
N. Nurdin, G. Helary, and G. Sauvet, *Journal of Applied Polymer Science*, 1993, 50, 671.
G. Sauvet, S. Dupond, K. Kazmierski, and J. Chojnowski, *Journal of Applied Polymer Science*, 2000, 75, 1005.
G. N. Tew, D. Lui, B. Chen, R. J. Doerksen, J. Kaplan, P. J. Carroll, M. L. Klein, and W. F. D. Grado, *PNAS*, 2002, 99, 5110.
D. E. Bergbreiter, B. Srinivas, G. F. Xu, H. N. Gray and A. Bandella, *Journal of Plastic Film & Sheeting*, 1996, 12, 15-26.
G. Fourche, *Polymer Engineering and Science*, 1995, 35, 968-975.
W. H. Waddell, L. R. Evans, J. G. Gillick and D. Shuttleworth, *Rubber Chemistry and Technology*, 1992, 65, 687-696.
M. Dhayal, K. Awasthi,Y. K. Vijay and D. K. Avasthi, *Vacuum*, 2006, 80, 643-646.
P. K. Wu andT. M. Lu, *Applied Physics Letters*, 1997, 71, 2710-2712.
International Search Report for PCT/GB2007//003194, mailed Nov. 6, 2007.
Written Opinion of the International Searching Authority for PCT/GB2007/003194, mailed Nov. 6, 2007.
J. Lin, S. Y. Qiu, K. Lewis and A. M. Klibanov, *Biotechnol. Prog.*, 2002, 18, 1082-1086.
J. Lin, S. Y. Qiu, K. Lewis and A. M. Klibanov, *Biotechnol. Bioeng.*, 2003, 83, 168-172.
J. Lin, J. C. Tiller, S. B. Lee, K. Lewis and A. M. Klibanov, *Biotechnol. Lett.*, 2002, 24, 801-805.
H. Shao, W. D. Meng and F. L. Qing, *J. Fluor. Chem.*, 2004, 125, 72 1-724.
B. Jansen and W. Kohnen, *Journal of Industrial Microbiology*, 1995, 15, 391-396.
Y. H. Sun, L. X. Feng and X. X. Zheng, *J. Appl. Polym. Sci.*, 1999, 74, 2826-2831.
Y. Ikada, *Biomaterials*, 1994, 15, 725-736.
Z. L. Shi, K. G. Neoh and E. T. Kang, *Langmuir*, 2004, 20, 6847-6852.
D. L. Pappas, J. J. Cuomo and K.G.. Sachdev, *Journal of Vacuum Science & Technology A-Vacuum Surfaces and Films*, 1991,9,2704-2708.
Sartomer Application Bulletin 4025, Oct. 2005, pp. 1-7.
Polymer, 1981, vol. 22, January, pp. 7-16.
Y. H. Choi, J. H. Kim, K. H. Paek, W. T. Ju and Y. S. Hwang, *Surface & Coatings Technology*, 2005, 193, 319-324.
S.Yang and M. C. Gupta, *Surface & Coatings Technology*, 2004, 187, 172-176.
H. Z. Liu, N. Y. Cui, N. M. D. Brown and B. J. Meenan, *Surface & Coatings Technology*, 2004, 185, 311-320.
B. T. Ginn and 0. Steinbock,*Langmuir*, 2003, 19, 8117-8118.
G. H. Shin,Y. H. Lee, J. S. Lee,Y. S. Kim, W. S. Choi and H. J. Park, *Journal of Agricultural and Food C'hemistry*, 2002, 50, 4608-46 14.
B. Tomcik, D. R. Popovic, I. V. Jovanovic and Z. L. J. Petrovic, *Journal of Polymer Research-Taiwan*, 2001, 8, 259-266.
G. R. Yang, H. Shen, C. Li and T. M. Lu, *Journal of Electronic Materials*, 1997, 26, 78-82.
C. M. Chan, T. M. Ko and H. Hiracka, *Surface Science Reports*, 1996, 24, 3-54.
M. H. Bernier, L. J. B. Klembergsapieha, L. Martinu and M. R. Wertheimer, *ACS Symposium Series*, 1990, 440,147-160.
H. J. Griessner and J. H. Hodgkin, *Biomaterials*, 1988, 9, 292-292.
L. Guzman, R. Celva, A. Miotello, B. Voltolini, F. Ferrari and M. Adami, *Surface & Coatings Technology*, 1998, 104, 375-379.
P. Laurens, *Annales De Chimie-Science Des Materiaux*, 2003, 28, 67-80.
M. Charbonnier, M. Romand, H. Esrom and R. Seebock, *Journal OfAdhesion*, 2001, 75, 381-404.
M. Ozdemir and H. Sadikoglu, *Trends in Food Science & Technology*, 1998, 9, 159-167.
S. J. Sofia and E. W. Merrill, *Journal of Biomedical Materials Research*, 1998, 40, 153-163.
E. Sancaktar, *Journal OfAdhesion Science and Technology*, 1999, 13, 179-201.
S. Siau, A. Vervaet, E. Schacht, U. Demeter and A. Van Caister, *Thin Solid Films*, 2006, 495, 348-356.
J. Friedrich, G. Kuhn, R. Mix, A. Fritz and A. Schonhals, *Journal OfAdhesion Science and Technology*, 2003, 17, 1591-1617.
V. M. Rudoy and V. A. Ogarev, *Makromolekulare Chemie-Macromolecular Symposia*, 1991, 44, 303-315.
D. B. Packham, *International Journal OfAdhesion and Adhesives*, 2003, 23, 437-448.
L. A. Felton and J. W. McGinity, *European Journal of Pharmaceutics and Biopharmaceutics*, 1999, 47, 3-14.
G. Fourche, *Polymer Engineering and Science*, 1995, 35, 957-967.
I. Lee and R. P. Wool, Macromolecules, 2000, 33, 2680-2687.
A. J. Crosby, M. Hageman and A. 1)uncan, *Langmuir*, 2005, 21, 11738-11743.
T. X. Xie and G. S. Yang, *J. Appl. Polym. Sci.*, 2004, 93, 2478-2483.
P. J. Cole and C. W. Macosko, *Journal of Plastic Film & Sheeting*, 2000, 16, 2 13-2.
A. K. Bhowmick and T. Inoue, *Journal OfAdhesion*, 1996, 59, 265-280.
A. J. Crosby, *Journal of Materials Science*, 2003, 38, 4439-4449.
N. Maeda, N. H. Chen, M. Tirrell and J. N. Israelachvili, *Science*, 2002, 297, 379-3 82.
J. T. Koberstein, D. E. Duch, W. Hu, T. J. Lenk, R. Bhatia, H. R. Brown, J. P. Lingelser andY. Gallot, *Journal of Adhesion*, 1998, 66, 229-249.
A. P. Chiriac, *Polymer Testing*, 2001, 20, 873-877.
I. Neamtu, A. P. Chiriac, G. E. loartid and C. I. Simionescu, *Polymer Testing*, 1999, 18, 415-427.
K. Kato, E. Uchida, E. T. Kang, Y. Uyama andY. Ikada, *Progress in Polymer Science*, 2003, 28, 209-259.
E. Ranucci, A. Sandgren, N. Andronova and A. C. Albertsson, *J. Appl. Polym. Sci.*, 2001, 82, 1971-1985.
Z. P. Wu, D. Z. Wu, W. T. Yang and R. G. Jin, *Journal of Materials Chemistry*, 2006, 16, 310-316.
M. Ozdemir, C. U. Yurteri and H. Sadikoglu, *Critical Reviews in Food Science and Nutrition*, 1999, 39, 457-477.
M. Herrero, B. Quemener, S. Ulve, H. Reinecke, C. Mijangos andY. Grohens, *Journal of Adhesion Science and Technology*, 2006, 20, 183-195.
D. Delmar-Greenberg, *Abstracts of Papers of the American Chemical Society*, 2003, 225, U579-U579.
M. J. Bridgett, M. C. Davies and S. P. Denyer, *Biomaterials*, 1992, 13, 411-416.
Proc. Natl. Acad. Sci. of the USA, 2006, vol. 103(31), pp. 11452-11456 & Chemical Abstracts, abstr. No. 145:408227.
Pure and Applied Chemistry, 1997, vol. 69(4), pp. 4196-4197 & Chemical Abstracts, abstr. No. 127: 161420.
Journal of Organic Chemistry, 1993, vol. 58(16), pp. 4196-4197 & Chemical Abstract abstr No. 119:202826.
Journal of the American Chemical Society, 1992, vol. 114(19), pp. 7590-7591 & Chemical Abstracts, abstr. No. 17:150487.
Journal of the American Chemical Society, 1991, vol. 113(10), pp. 3925-3934 & Chemical Abstracts, abstr. No. 114:228175.

* cited by examiner

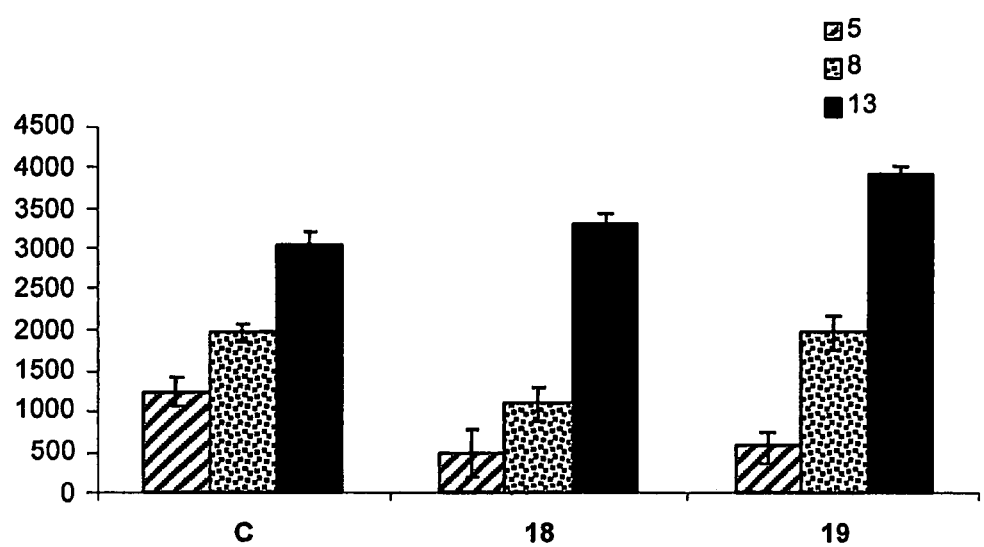

CARBENE PRECURSOR COMPOUND FOR PRODUCING AN ADHESIVE SURFACE ON A SUBSTRATE

This application is the U.S. national phase of International Application No. PCT/GB2007/003194, filed 22 Aug. 2007, which designated the U.S. and claims priority to Great Britain Application no. 0616724.1, filed 23 Aug. 2006, the entire contents of which are hereby incorporated by reference.

FIELD OF INVENTION

The present invention relates to a process for producing a substrate having an adhesive surface using an arylcarbene as the reactive intermediate. The process allows the ability of a substrate to adhere to other materials to be tailored. Other surface properties, including dispersability, hydrophobicity, hydrophilicity, oleophobicity and oleophilicity, may also be controlled by application of this invention as desired. The invention in particular relates to a process for producing a polymeric or an inorganic substrate which is capable of adhesion to a further material. The invention further relates to carbene precursor compounds for use in the process, substrates produced by the process and to processes for preparing certain precursor compounds.

Modern technology and products are critically dependent on the use of advanced materials with properties carefully tailored to the desired specific application. These properties can rarely be achieved with one homogeneous material, but are readily available by coating or laminating one material onto another, giving a composite whose properties combine the desired properties of each component. Of particular importance is the achievement of nanolayer surface modifications, since this changes the surface characteristics of the polymer, but without changing the bulk (e.g. mechanical strength) properties of the substrate. Such composite materials possessing hybrid properties find wide application in the aeronautical, automotive, hygiene, computing, and consumer product industries, frequently as components which are critical for successful function of a device or product. Such high value-added plastic and polymeric materials can, however, be expensive to produce, since each polymer hybrid-needs to be individually designed and tested for optimal properties, and downstream development and production costs can represent a significant barrier to their adoption.

Polymers are well known for their wide availability and low cost, and have been used for a myriad of product applications. However, it is very common for their superior performance in one area to be compromised by a poor or less than desirable performance in another. The performance of any polymeric material in a given application will depend upon any of a number of characteristics, including brittleness, flexibility, colour, thermal and light stability, solvent resistance and biocompatibility amongst many others. Although these properties might be desired or required, deficiencies often arise in polymer performance because these macroscopic properties are compromised by undesirable or unsuitable surface characteristics. Alternatively, it would be of substantial value if a method for the reliable modification of a polymer surface were available so that novel surface characteristics could be introduced onto a polymer. Thus, it would be highly advantageous to be able to manipulate macroscopic properties and surface characteristics independently, so as to maintain favoured bulk properties of the polymer, but to adjust surface properties to suit a given application, and this approach has received some attention; common methods include abrasion and sand blasting, chemical treatment, and surface activation. Amongst the latter, a diversity of techniques has been developed: atom bombardment, plasma treatment, ion implantation, laser treatment, electron beam, and welding are all well known. Although effective and widely used in industrial applications, the disadvantage with many of these techniques is their high operating cost and large infrastructure requirements, which makes them unsuitable for a wide spectrum of applications. Polymer surface modification has been reported using chemical surface treatments; for example, cured epoxy polymers containing reactive hydroxyl groups were chemically modified with trichlorotriazine followed by either iminodiacetic acid or imidazole, in order to enhance the electrochemical deposition of copper.

Adhesion of polymeric materials is of particular importance in a diversity of applications, since this determines the nature of the surface interaction of a polymer with its environment, and some important causative factors for adhesion have been reported such as the density of functional groups and surface topography. Adhesion can also be important in fibre-polymer composite materials and in co-extrusion. However, although understanding of the factors which determine interfacial effects is increasingly advanced, using this knowledge to design preferred surface characteristics is still in its infancy. One approach for the modification of the adhesion-characteristics is to modify the bulk polymer itself; for example, acrylates which are polymerised in the presence of a vegetable extract from *Asclepias syriaca* exhibit improved adhesive properties, although the polymerisation step is slowed; cross-linking in acrylovinylic polymers followed by corona discharge or cold plasma treatment can improve adhesion. An important disadvantage of this approach is that, in order to achieve surface modification, the entire bulk characteristics of the polymer are changed, which is highly undesirable if the enhancement of surface properties comes at the expense of the required bulk properties. Surface grafting using physical treatments can alter a variety of properties, but as discussed above, can be limited by cost and infrastructure requirements. Chemical pre-treatment of polyimide polymers by sulfonation and by hydroxide can enhance metallisation (silver), but this is achieved by chemical degradation of the surface.

Diverse applications for surface modified polymers range from food packaging, to the incorporation of disinfecting function. The modification of bacterial adhesion has been studied and, for example, polystyrene modified with polyethylene oxide and polypropylene oxide exhibits anti-adhesive effects with *Staphylococcus epidermidis*. The incorporation of bactericidal activity and prevention of biofilm formation has been shown to be possible, and so has the reverse, the improvement of biocompatibility. A further application of significance is the metallisation of polymer surfaces of relevance in printed circuit board and electronic technology.

In particular, a trend towards increased use of low surface energy polymers such as polyethylene and polypropylene is driven by a number of factors including the regulatory framework which requires the replacement of polymers such as polystyrene, PVC and teflon for less toxic alternatives; favourable polymer feedstock prices; their ease of moulding and shaping; their suitability for packaging applications; and environmental and recycling considerations. However, it has been noted that PPP and PE cannot normally be surface activated, because their low surface energy inhibits wetting by a solvent. Thus, the key advantage of these polymers in many applications—their inertness—can become their key limitation, since this inertness prevents novel polymeric functions to be developed.

There is therefore a continuing need to develop an improved system for modifying the adhesive properties of substrates such as polymeric materials.

SUMMARY OF THE INVENTION

A process has now been developed which allows the surface of a substrate to be functionalised in such a way as to impart adhesive properties to the surface. The resulting functionalised surface is thus capable of adhering to a variety of materials. Other surface properties of the substrate, such as hydrophobicity, hydrophilicity, oleophobicity, oleophilicity and dispersability, may also be controlled or modified using this process as desired. This process is applicable to a wide variety of substrates, including both organic and inorganic materials.

Accordingly, the present invention provides a process for producing a substrate having an adhesive surface, which process comprises:

(a) contacting the substrate with a carbene precursor, which carbene precursor is a compound of the following formula (I):

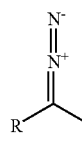

wherein:

A is an aryl or heteroaryl ring;

y is 1, 2, 3, 4 or 5;

$L_A$ is a single bond, -alk-, -arylene-, -alk-arylene-, -X-alk-, -X-alk-X-, -X-arylene-, X-arylene-X-, -X-alk-arylene-, -alk-X-arylene-, -alk-arylene-X, -X-alk-X-arylene-, -alk-X-arylene-X- or -X-alk-X-arylene-X-, wherein X is N(R"), O, or S and wherein alk is $C_{1-20}$ alkylene which is optionally interrupted by N(R"), O, S or arylene, wherein R" is H, $C_{1-6}$ alkyl or aryl;

$W_A$ is a group comprising an adhesive functional group or a group which is a precursor of an adhesive functional group;

R is selected from hydrogen, aryl, heteroaryl, $C_{1-10}$ alkoxy, aryloxy, di($C_{1-10}$)alkylamino, alkylarylamino, diarylamino, $C_{1-10}$ alkylthio, arylthio and $CR'_3$, wherein each R' is independently selected from a halogen atom, aryl, heteroaryl, $C_{3-7}$ cycloalkyl, $C_{3-7}$ heterocyclyl and $C_{1-6}$ alkyl, which $C_{1-6}$ alkyl is optionally interrupted by N(R"), O, S or arylene wherein R" is as defined above;

provided that when R is aryl or heteroaryl, said aryl or heteroaryl may be unsubstituted or substituted by one, two, three, four or five groups, which groups are independently selected from $C_{1-6}$ alkyl, aryl, cyano, amino, keto, $C_{1-10}$ alkylamino, di($C_{1-10}$alkylamino, arylamino, diarylamino, arylalkylamino, amido, hydroxy, halo, carboxy, ester, $C_{1-6}$ alkoxy, aryloxy, haloalkyl, thiol, $C_{1-10}$ alkylthio, arylthio, sulfonic acid, sulfonyl and -$L_B$-$W_B$, wherein $L_B$ is as defined above for $L_A$ and is the same as or different from $L_A$, and $W_B$ is as defined above for $W_A$ and is the same as or different from $W_A$; and (b) either (i) when $W_A$ or $W_B$ comprises an adhesive functional group, generating a carbene reactive intermediate from the carbene precursor so that it reacts with the substrate to functionalise the surface, thereby yielding said substrate having an adhesive surface; or (ii) when $W_A$ or $W_B$ comprises a group which is a precursor of an adhesive functional group, generating a carbene reactive intermediate from the carbene precursor so that it reacts with the substrate to functionalise the surface, and (c) converting said group which is a precursor into an adhesive functional group thereby yielding said substrate having an adhesive surface.

In step (b), the carbene reactive intermediate is typically generated by electromagnetic irradiation, ultrasonic irradiation or thermal irradiation. Typically, the carbene reactive intermediate is generated by thermal irradiation, for instance by heating.

The adhesive functional groups which are introduced onto the surface of the substrate by the process of the invention are themselves capable of interaction with the surfaces of other materials (termed herein "adherends"), in order to aid adhesion of the substrate to those materials. Different adhesive functional groups are capable of interaction with different adherends. Thus, by selecting an appropriate adhesive functional group, the substrate in question can be adhered to a particular adherend as desired.

Furthermore, by selecting an appropriate adhesive functional group certain other surface properties of the substrate, including dispersability, hydrophobicity, hydrophilicity, oleophobicity and oleophilicity, may be modified or controlled as desired.

The process of the invention offers significant economic and technical bulk advantages. First, it is applicable to a diverse range of substrates including but not limited to natural and synthetic polymers and inorganic solids, and to a diverse range of adherends which may be adhered to such substrates. Second, only the surface of the substrate is modified: the fact that the functionality is confined to the surface of the substrate is advantageous because the bulk of the substrate is effectively unchanged and therefore the bulk properties of the substrate, including mechanical strength, remain unaffected by the adhesive properties that are imparted to its surface. This is particularly significant for applications in which it is important to retain the properties of the individual materials in a composite material formed by adhesion.

The invention further provides a carbene precursor compound of the following formula (I):

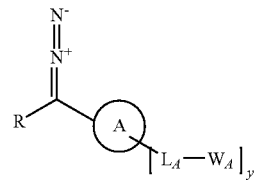

wherein:

A is an aryl or heteroaryl ring;

y is 1, 2, 3, 4 or 5;

$L_A$ is a single bond, -alk-, -arylene-, -alk-arylene-, -X-alk-, -X-alk-X-, -X-arylene-, X-arylene-X-, -X-alk-arylene-, -alk-X-arylene-, -alk-arylene-X, -X-alk-X-arylene-, -alk-X-arylene-X- or -X-alk-X-arylene-X-, wherein X is N(R"), O, or S and wherein alk is $C_{1-20}$ alkylene which is optionally interrupted by N(R"), O, S or arylene, wherein R" is H, $C_{1-6}$ alkyl or aryl;

$W_A$ is a group comprising an adhesive functional group or a group which is a precursor of an adhesive functional group;

R is selected from aryl, heteroaryl, $C_{1-10}$ alkoxy, aryloxy, di($C_{1-10}$)alkylamino, alkylarylamino, diarylamino, $C_{1-10}$ alkylthio, arylthio and $CR'_3$, wherein each R' is independently selected from a halogen atom, aryl, heteroaryl, $C_{3-7}$ cycloalkyl, $C_{5-7}$ heterocyclyl and $C_{1-6}$ alkyl, which $C_{1-6}$ alkyl is optionally interrupted by N(R"), O, S or arylene wherein R" is as defined above, provided that R is not $CF_3$;

provided that when R is aryl or heteroaryl, said aryl or heteroaryl may be unsubstituted or substituted by one, two, three, four or five groups, which groups are independently selected from $C_{1-6}$ alkyl, aryl, cyano, amino, keto, $C_{1-10}$ alkylamino, di($C_{1-10}$)alkylamino, arylamino, diarylamino, arylalkylamino, amido, hydroxy, halo, carboxy, ester, $C_{1-4}$ alkoxy, aryloxy, haloalkyl, thiol, $C_{1-10}$alkylthio, arylthio, sulfonic acid, sulfonyl and -$L_B$-$W_B$, wherein $L_B$ is as defined above for $L_A$ and is the same as or different from $L_A$, and $W_B$ is as defined above for $W_A$ and is the same as or different from $W_A$, provided that the compound is not: 4,4'-bis(N-acetyl-2-aminoethyl)diphenyldiazomethane, 1-{2-[4-(diazo-phenyl-methyl)-benzyloxy]-ethyl}-3-phenyl urea, 4-([N-ethyl-N-phenyl-2-aminoethyl]oxymethyl)phenyl phenyl diazomethane, bis-4,4'-N,N-dimethylamino diphenyldiazomethane, 4-([3,4-dimethoxyphenyl]oxymethyl)phenyl phenyl diazomethane, 4-([3-N,N-diethylaminophenyl]oxymethyl)phenyl phenyl diazomethane, 4-([N-ethyl-N-phenyl-2-aminoethyl]oxymethyl)phenyl phenyl diazomethane or bis-4,4'-tert-butyl ester diphenyldiazomethane.

The present invention further provides a process for producing a substrate having a functionalised surface, which process comprises: (a) contacting the substrate with a carbene precursor compound of formula (I) as defined above; and (b) generating a carbene reactive intermediate from the carbene precursor so that it reacts with the substrate to functionalise the surface, thereby yielding said substrate having a functionalised surface.

The invention further provides a substrate which is obtainable by the process of the invention for producing a substrate having an adhesive surface as defined above. Yet further, the invention provides a substrate which is obtainable by the process of the invention for producing a substrate having a functionalised surface as defined above.

The invention further provides a substrate having a functionalised surface, which surface is functionalised with one or more groups of the following formula (II):

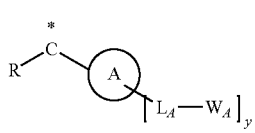

(II)

wherein:
* is the point of attachment of the group of formula (II) to the substrate;
A is an aryl or heteroaryl ring;
y is 1, 2, 3, 4 or 5;
$L_A$ is a single bond, -alk-, -arylene-, -alk-arylene-, -X-alk-, -X-alk-X-, -X-arylene-, X-arylene-X-, -X-alk-arylene-, -alk-X-arylene-, -alk-arylene-X, -X-alk-X-arylene-, -alk-X-arylene-X- or -X-alk-X-arylene-X-, wherein X is N(R"), O, or S and wherein alk is $C_{1-20}$ alkylene which is optionally interrupted by N(R"), O, S or arylene, wherein R" is H, $C_{1-6}$ alkyl or aryl;

$W_A$ is a group comprising a functional group selected from: OH, $NH_2$, SH, M, a group containing an aliphatic carbon-carbon double bond, a group containing an epoxide group, and a group having the following structure:

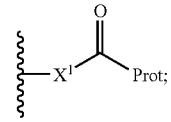

$X^1$ is a single bond, C(R")(R'''), N(R") or O, wherein R" is as defined above and R''' is H, $C_{1-6}$ alkyl or aryl;

Prot is a protecting group which is a precursor to a -CH=$CH_2$ group;

M is a group that is capable of adhering to a metal, a metal alloy or a metal salt, or M is a group which is a precursor of a group that is capable of adhering to a metal, metal alloy or a metal salt;

R is selected from hydrogen, aryl, heteroaryl, $C_{1-10}$ alkoxy, aryloxy, di($C_{1-10}$)alkylamino, alkylarylamino, diarylamino, $C_{1-10}$ alkylthio, arylthio and $CR'_3$, wherein each R' is independently selected from a halogen atom, aryl, heteroaryl, $C_{3-7}$ cycloalkyl, $C_{5-7}$ heterocyclyl and $C_{1-6}$ alkyl, which $C_{1-6}$ alkyl is optionally interrupted by N(R"), O, S or arylene wherein R" is as defined above;

provided that when R is aryl or heteroaryl, said aryl or heteroaryl may be unsubstituted or substituted by one, two, three, four or five groups, which groups are independently selected from $C_{1-6}$ alkyl, aryl, cyano, amino, keto, $C_{1-10}$ alkylamino, di($C_{1-10}$)alkylamino, arylamino, diarylamino, arylalkylamino, amido, hydroxy, halo, carboxy, ester, $C_{1-6}$ alkoxy, aryloxy, haloalkyl, thiol, $C_{1-10}$ alkylthio, arylthio, sulfonic acid, sulfonyl and -$L_B$-$W_B$, wherein $L_B$ is as defined above for $L_A$ and is the same as or different from $L_A$, and $W_B$ is as defined above for $W_A$ and is the same as or different from $W_A$.

The point of attachment of the group of formula (II) to the substrate is depicted "*". Thus, in the substrate of the invention having a functionalised surface as defined above, the carbon atom marked "*" is bonded to the substrate. As the skilled person would understand, various different modes of binding of the group of formula (II) to the substrate are possible via that carbon atom. For example, the bond between the carbon atom marked "*" and an atom "Z" of the substrate may be a single covalent bond, in which case that carbon atom is also bonded to another atom (for example a hydrogen atom), as follows:

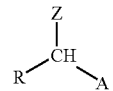

Alternatively, the bond between the carbon atom marked "*" and an atom "Z" of the substrate may be a double bond, as follows:

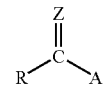

Alternatively, the bond between the carbon atom marked "*" and an atom "Z" of the substrate may be a dative bond (also known as a coordinate bond), in which both electrons are provided by the carbon atom, as follows:

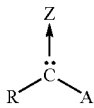

Alternatively, the carbon atom marked "*" of the group of formula (II) may be bonded to two atoms, "Z" and "V", of the substrate, wherein the bonds between the carbon atom marked "*" and the atoms Z and Z' are both single bonds, as follows:

The invention further provides a process for producing a compound of formula (III):

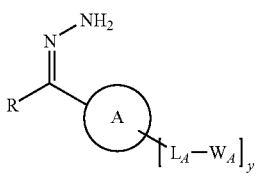

wherein:
A is an aryl or heteroaryl ring;
y is 1, 2, 3, 4 or 5;
$L_A$ is a single bond, -alk-, -arylene-, -alk-arylene-, -X-alk-, -X-alk-X-, -X-arylene-, X-arylene-X-, -X-alk-arylene-, -alk-X-arylene-, -alk-arylene-X, -X-alk-X-arylene-, -alk-X-arylene-X- or -X-alk-X-arylene-X-, wherein X is N(R''), O, or S and wherein alk is $C_{1-20}$ alkylene which is optionally interrupted by N(R''), O, S or arylene, wherein R'' is H, $C_{1-6}$ alkyl or aryl;
$W_A$ is a group comprising an adhesive functional group or a group which is a precursor of an adhesive functional group;
R is selected from aryl, heteroaryl, $C_{1-10}$ alkoxy, aryloxy, di($C_{1-10}$)alkylamino, alkylarylamino, diarylamino, $C_{1-10}$ alkylthio, arylthio and CR'$_3$, wherein each R' is independently selected from a halogen atom, aryl, heteroaryl, $C_{3-7}$ cycloalkyl, $C_{5-7}$ heterocyclyl and $C_{1-6}$ alkyl, which $C_{1-6}$ alkyl is optionally interrupted by N(R''), O, S or arylene wherein R'' is as defined above, provided that R is not $CF_3$;
provided that when R is aryl or heteroaryl, said aryl or heteroaryl may be unsubstituted or substituted by one, two, three, four or five groups, which groups are independently selected from $C_{1-6}$ alkyl, aryl, cyano, amino, keto, $C_{1-10}$ alkylamino, di($C_{1-10}$)alkylamino, arylamino, diarylamino, arylalkylamino, amido, hydroxy, halo, carboxy, ester, $C_{1-6}$ alkoxy, aryloxy, haloalkyl, thiol, $C_{1-10}$ alkylthio, arylthio, sulfonic acid, sulfonyl and -$L_B$-$W_B$, wherein $L_B$ is as defined above for $L_A$ and is the same as or different from $L_A$, and $W_B$ is as defined above for $W_A$ and is the same as or different from $W_A$; and
provided that the compound is not: 4,4'-bis(N-acetyl-2-aminoethyl)benzophenone hydrazone, 1-{2-[4-(hydrazonophenyl-methyl)-benzyloxy]-ethyl}-3-phenyl urea, 4,4-bis-N, N-dimethylamino benzophenone hydrazone, 4-([3,4-dimethoxyphenyl]oxymethyl)benzophenone hydrazone, 4-([3-N,N-diethylaminophenyl]oxymethyl)benzophenone hydrazone, 4-([N-ethyl-N-phenyl-2-aminoethyl]oxymethyl) benzophenone hydrazone or 4,4'-bis-tert-butyl ester benzophenone hydrazone;
the process comprising treating a compound of formula (IV) with hydrazine in the presence of heat:

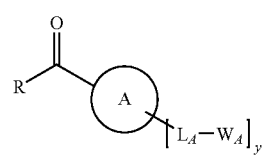

wherein R, A, $L_A$, $W_A$, and y are as defined above.
The resulting compound of formula (III) may subsequently be converted into carbene precursor compounds of formula (I).
Accordingly, the invention further provides a process for producing a carbene precursor compound of formula (I):

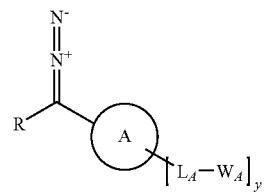

wherein R, A, $L_A$, $W_A$, and y are as defined above for the carbene precursor compounds of the invention, which process comprises oxidizing a compound of formula (III) as defined above.

BRIEF DESCRIPTION OF THE FIGURE

FIG. 1 is a bar chart of the results of the AlamarBlue™ cell proliferation study of Example 13, showing the average relative fluorescent unit (RFU) value (y axis), on days 5, 8 and 13, for the control Hybond-N polymer membrane (C), the Hybond-N membrane functionalised with phosphonic acid (18) and the Hybond-N membrane functionalised with phosphonic acid calcium salt (19) (x axis). The cross-hatched bars show the results at day 5, the spotted bars at day 8 and the solid bars at day 13.

DETAILED DESCRIPTION OF THE INVENTION

The following substituent definitions apply with respect to the compounds of formula (I), groups of formula (II) and compounds of formulae (III) and (IV) defined herein, whether they are defined in relation to the processes, compounds, or substrates of the invention:
A $C_{1-20}$ alkyl group is an unsubstituted or substituted, straight or branched chain saturated hydrocarbon radical. Typically it is $C_{1-10}$ alkyl, for example methyl, ethyl, propyl, butyl, pentyl, hexyl, heptyl, octyl, nonyl or decyl, or $C_{1-6}$ alkyl, for example methyl, ethyl, propyl, butyl, pentyl or hexyl, or $C_{1-4}$ alkyl, for example methyl, ethyl, i-propyl, n-propyl, t-butyl, s-butyl or n-butyl. When an alkyl group is substituted it typically bears one or more substituents selected from $C_{1-6}$ alkyl which is unsubstituted, aryl (as defined herein), cyano, amino, $C_{1-10}$ alkylamino, di($C_{1-10}$)alkylamino, arylamino, diarylamino, arylalkylamino, amido, hydroxy, halo, carboxy, ester, keto, $C_{1-6}$ alkoxy, aryloxy, haloalkyl, sulfonic acid, sulfhydryl (i.e. thiol, —SH), $C_{1-10}$alkylthio, arylthio and sulfonyl. Examples of substituted alkyl groups include haloalkyl, hydroxyalkyl, aminoalkyl, alkoxyallyl and alkaryl groups. The term alkaryl, as used herein, pertains to a $C_{1-20}$alkyl group in which at least one hydrogen atom (e.g., 1, 2, 3) has been replaced with an aryl group. Examples of such groups include, but are not limited to, benzyl (phenylmethyl, PhCH$_2$—), benzhydryl (Ph$_2$CH—), trityl (triphenylmethyl, Ph$_3$C—), phenethyl (phenylethyl, Ph—CH$_2$CH$_2$—), styryl (Ph—CH=CH—), cinnamyl (Ph—CH=CH—CH$_2$—).

A $C_{3-20}$ cycloalkyl group is an unsubstituted or substituted alkyl group which is also a cyclyl group; that is, a monovalent moiety obtained by removing a hydrogen atom from an alicyclic ring atom of a carbocyclic ring of a carbocyclic compound, which moiety has from 3 to 20 carbon atoms (unless otherwise specified), including from 3 to 20 ring atoms. Thus, the term "cycloalkyl" includes the sub-classes cycloalkyenyl and cycloalkynyl. Preferably, each ring has from 3 to 7 ring atoms. Examples of groups of $C_{3-20}$ cycloalkyl groups include cycloalkyl, $C_{3-15}$ cycloalkyl, $C_{3-10}$ cycloalkyl, $C_{3-7}$ cycloalkyl. When a $C_{3-20}$ cycloalkyl group is substituted it typically bears one or more substituents selected from $C_{1-6}$ alkyl which is unsubstituted, aryl (as defined herein), cyano, amino, $C_{1-10}$ alkylamino, di($C_{1-10}$)alkylamino, arylamino, diarylamino, arylalkylamino, amido, hydroxy, halo, carboxy, ester, keto, $C_{1-6}$ alkoxy, aryloxy, haloalkyl, sulfonic acid, sulfhydryl (i.e. thiol, —SH), $C_{1-10}$ alkylthio, arylthio and sulfonyl.

Examples of $C_{3-20}$ cycloalkyl groups include, but are not limited to, those derived from saturated monocyclic hydrocarbon compounds:

cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$);

saturated polycyclic hydrocarbon compounds:
thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$); unsaturated polycyclic hydrocarbon compounds: camphene ($C_{10}$), limonene ($C_{10}$), pinene ($C_{10}$);

polycyclic hydrocarbon compounds having an aromatic ring:
indene ($C_9$), indane (e.g., 2,3-dihydro-1H-indene) ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), aceanthrene ($C_{16}$), cholanthrene ($C_{20}$).

A $C_{3-20}$ heterocyclyl group is an unsubstituted or substituted monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms. When a $C_{3-20}$ heterocyclyl group is substituted it typically bears one or more substituents selected from $C_{1-6}$ alkyl which is unsubstituted, aryl (as defined herein), cyano, amino, $C_{1-10}$ alkylamino, di($C_{1-10}$)alkylamino, arylamino, diarylamino, arylalkylamino, amido, hydroxy, halo, carboxy, ester, keto, $C_{1-6}$ alkoxy, aryloxy, haloalkyl, sulfonic acid, sulfhydryl (i.e. thiol, —SH), $C_{1-10}$ alkylthio, arylthio and sulfonyl.

Examples of groups of heterocyclyl groups include $C_{3-20}$heterocyclyl, $C_{5-20}$heterocyclyl, $C_{3-15}$heterocyclyl, $C_{5-15}$heterocyclyl, $C_{3-12}$heterocyclyl, $C_{5-12}$heterocyclyl, $C_{3-10}$heterocyclyl, $C_{5-10}$heterocyclyl, $C_{3-7}$heterocyclyl, $C_{5-7}$heterocyclyl, and $C_{5-6}$heterocyclyl.

Examples of (non-aromatic) monocyclic $C_{3-20}$ heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of $C_{3-20}$ heterocyclyl groups which are also aryl groups are described below as heteroaryl groups.

An aryl group is a substituted or unsubstituted, monocyclic or bicyclic aromatic group which typically contains from 6 to 14 carbon atoms, preferably from 6 to 10 carbon atoms in the ring portion. Examples include phenyl, naphthyl, indenyl and indanyl groups. An aryl group is unsubstituted or substituted. When an aryl group as defined above is substituted it typically bears one or more substituents selected from $C_1$-$C_6$ alkyl which is unsubstituted (to form an aralkyl group), aryl which is unsubstituted, cyano, amino, $C_{1-10}$ alkylamino, di($C_{1-10}$) alkylamino, arylamino, diarylamino, arylalkylamino, amido, hydroxy, halo, carboxy, ester, keto, alkoxy, aryloxy, haloalkyl, sulfhydryl (i.e. thiol, —SH), $C_{1-10}$ alkylthio, arylthio, sulfonic acid and sulfonyl. Typically it carries 0, 1, 2 or 3 substituents. The term aralkyl as used herein, pertains to an aryl group in which at least one hydrogen atom (e.g., 1, 2, 3) has been substituted with a $C_{1-6}$ alkyl group. Examples of such groups include, but are not limited to, tolyl (from toluene), xylyl (from xylene), mesityl (from mesitylene), and cumenyl (or cumyl, from cumene), and duryl (from durene).

Alternatively, the ring atoms may include one or more heteroatoms, as in a heteroaryl group. A heteroaryl group is a substituted or unsubstituted mono- or bicyclic heteroaromatic group which typically contains from 6 to 10 atoms in the ring portion including one or more heteroatoms. It is generally a 5- or 6-membered ring, containing at least one heteroatom selected from O, S, N, P, Se and Si. It may contain, for example, 1, 2 or 3 heteroatoms. Examples of heteroaryl groups include pyridyl, pyrazinyl, pyrimidinyl, pyridazinyl, furanyl, thienyl, pyrazolidinyl, pyrrolyl, oxazolyl, oxadiazolyl, isoxazolyl, thiadiazolyl, thiazolyl, isothiazolyl, imidazolyl, pyrazolyl, quinolyl and isoquinolyl. A heteroaryl group may be unsubstituted or substituted, for instance, as specified above for aryl. Typically it carries 0, 1, 2 or 3 substituents.

A $C_{1-20}$ alkylene group is an unsubstituted or substituted bidentate moiety obtained by removing two hydrogen atoms, either both from the same carbon atom, or one from each of two different carbon atoms, of a hydrocarbon compound having from 1 to 20 carbon atoms (unless otherwise specified), which may be aliphatic or alicyclic, and which may be saturated, partially unsaturated, or fully unsaturated. Thus, the term "alkylene" includes the sub-classes alkenylene, alkynylene, cycloalkylene, etc., discussed below. Typically it is $C_{1-10}$ alkylene, for instance $C_{1-6}$ alkylene. Preferably it is $C_{1-4}$ alkylene, for example methylene, ethylene, i-propylene, n-propylene, t-butylene, s-butylene or n-butylene. It may also be pentylene, hexylene, heptylene, octylene and the various branched chain isomers thereof. An alkylene group may be unsubstituted or substituted as specified above for alkyl.

In this context, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$ alkylene," as used herein, pertains to an alkylene group having from 1 to 4 carbon atoms. Examples of groups of alkylene groups include $C_{1-4}$ alkylene ("lower alkylene"), $C_{1-7}$ alkylene, $C_{1-10}$ alkylene and $C_{1-20}$ alkylene.

Examples of linear saturated $C_{1-7}$ alkylene groups include, but are not limited to, —$(CH_2)_n$— where n is an integer from 1 to 7, for example, —$CH_2$-(methylene), —$CH_2CH_2$-(ethylene), —$CH_2CH_2CH_2$-(propylene), and —$CH_2CH_2CH_2CH_2$-(butylene).

Examples of branched saturated $C_{1-7}$ alkylene groups include, but are not limited to, —$CH(CH_3)$—, —$CH(CH_3)CH_2$—, —$CH(CH_3)CH_2CH_2$—, —$CH(CH_3)CH_2CH_2CH_2$—, —$CH_2CH(CH_3)CH_2$—, —$CH_2CH(CH_3)CH_2CH_2$—, —$CH(CH_2CH_3)$—, —$CH(CH_2CH_3)CH_2$—, and —$CH_2CH(CH_2CH_3)CH_2$—.

Examples of linear partially unsaturated $C_{1-7}$ alkylene groups include, but is not limited to, —CH=CH— (vinylene), —CH=CH—$CH_2$—, —$CH_2$—CH=$CH_2$—, —CH=CH—$CH_2$—$CH_2$—, —CH=CH—$CH_2$—$CH_2$—$CH_2$—, —$CH_2$—CH=CH—$CH_2$—, —$CH_2$—CH=CH—, —CH=CH—CH=CH—$CH_2$—, CH=CH—$CH_2$—, —CH=CH—CH=CH—$CH_2$—$CH_2$—, —CH=CH—$CH_2$—CH=CH—, and —CH=CH—$CH_2$—$CH_2$—CH=CH—.

Examples of branched partially unsaturated $C_{1-7}$ alkylene groups include, but is not limited to, —$C(CH_3)$=CH—, —$C(CH_3)$=CH—$CH_2$—, and —CH=CH—$CH(CH_3)$—.

Examples of alicyclic saturated $C_{1-7}$ alkylene groups include, but are not limited to, cyclopentylene (e.g., cyclopent-1,3-ylene), and cyclohexylene (e.g., cyclohex-1,4-ylene).

Examples of alicyclic partially unsaturated $C_{1-7}$ alkylene groups include, but are not limited to, cyclopentenylene (e.g., 4-cyclopenten-1,3-ylene), cyclohexenylene (e.g., 2-cyclohexen-1,4-ylene; 3-cyclohexen-1,2-ylene; 2,5-cyclohexadien-1,4-ylene).

An arylene group is an unsubstituted or substituted bidentate moiety obtained by removing two hydrogen atoms, one from each of two different aromatic-ring atoms of an aromatic compound, which moiety has from 5 to 14 ring atoms (unless otherwise specified). Typically, each ring has from 5 to 7 or from 5 to 6 ring atoms. An arylene group may be unsubstituted or substituted, for instance, as specified above for aryl.

In this context, the prefixes (e.g., $C_{5-20}$, $C_{6-20}$, $C_{5-14}$, $C_{5-7}$, $C_{5-6}$, etc.) denote the number of ring atoms, or range of number of ring atoms, whether carbon atoms or heteroatoms. For example, the term "$C_{5-6}$ arylene," as used herein, pertains to an arylene group having 5 or 6 ring atoms. Examples of groups of arylene groups include $C_{5-20}$ arylene, $C_{6-20}$ arylene, $C_{5-14}$ arylene, $C_{6-14}$ arylene, $C_{6-10}$ arylene, $C_{5-12}$ arylene, $C_{5-10}$ arylene, $C_{5-7}$ arylene, $C_{5-6}$ arylene, $C_5$ arylene, and $C_6$ arylene.

The ring atoms may be all carbon atoms, as in "carboarylene groups" (e.g., $C_{6-20}$ carboarylene, $C_{6-14}$ carboarylene or $C_{6-10}$ carboarylene).

Examples of $C_{6-20}$ arylene groups which do not have ring heteroatoms (i.e., $C_{6-20}$ carboarylene groups) include, but are not limited to, those derived from the compounds discussed above in regard to aryl groups, e.g. phenylene, and also include those derived from aryl groups which are bonded together, e.g. phenylene-phenylene (diphenylene) and phenylene-phenylene-phenylene (triphenylene).

Alternatively, the ring atoms may include one or more heteroatoms, as in "heteroarylene groups" (e.g., $C_{5-10}$ heteroarylene).

Examples of $C_{5-10}$ heteroarylene groups include, but are not limited to, those derived from the compounds discussed above in regard to heteroaryl groups.

As used herein the term ester (or carboxylate, carboxylic acid ester or oxycarbonyl) represents a group of formula: —C(H))OR, wherein R is an ester substituent, for example, a $C_{1-6}$ alkyl group, a $C_{3-20}$ heterocyclyl group, or an aryl group (typically a phenyl group). Examples of ester groups include, but are not limited to, —C(=O)OCH$_3$, —C(=O)OCH$_2$CH$_3$, —C(=O)OC(CH$_3$)$_3$, and —C(=O)OPh.

As used herein the term amino represents a group of formula —NH$_2$. The term $C_{1-10}$ alkylamino represents a group of formula —NHR' wherein R' is a $C_{1-10}$ alkyl group, preferably a $C_{1-6}$ alkyl group, as defined previously. The term di($C_{1-10}$)alkylamino represents a group of formula —NR'R" wherein R' and R" are the same or different and represent $C_{1-10}$ alkyl groups, preferably $C_{1-6}$ alkyl groups, as defined previously. The term arylamino represents a group of formula —NHR' wherein R' is an aryl group, preferably a phenyl group, as defined previously. The term diarylamino represents a group of formula —NR'R" wherein W and R" are the same or different and represent aryl groups, preferably phenyl groups, as defined previously. The term arylalkylamino represents a group of formula —NR'R" wherein R' is a $C_{1-10}$ alkyl group, preferably a $C_{1-6}$ alkyl group, and R" is an aryl group, preferably a phenyl group.

A $C_{1-10}$ alkylthio group is a said $C_{1-10}$ alkyl group, preferably a $C_{1-6}$ alkyl group, attached to a thio group. An arylthio group is an aryl group, preferably a phenyl group, attached to a thio group.

A $C_{1-10}$ alkoxy group is a said $C_{1-10}$ alkyl group attached to an oxygen atom. A $C_{1-6}$ alkoxy group is a said $C_{1-6}$ alkyl group attached to an oxygen atom. A $C_{1-4}$ alkoxy group is a $C_{1-4}$ alkyl group attached to an oxygen atom. Examples of $C_{1-4}$ alkoxy groups include, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy). An aryloxy group is an aryl group, preferably a phenyl group, attached to an oxygen atom. An example of an aryloxy group is —OPh (phenoxy).

As used herein, the term "phosphonic acid" represents a group of the formula: —P(=O)(OH)$_2$. As would be understood by the skilled person, a phosphonic acid group (for instance, when employed in the present invention as an adhesive functional group) can exist in protonated and deprotonated forms (for example, —P(=O)(OH)$_2$, —P(O)(O$^-$)$_2$ and —P(=O)(OH)(O$^-$)), and in salt forms (for example, —[P(=O)(OH)(O$^-$)]X$^+$, —[P(=O)(O$^-$)$_2$]2X$^+$ or —[P(=O)(O$^-$)$_2$] Z$^{2+}$, wherein X$^+$ is a monovalent cation and Z$^{2+}$ is a dication). Typically, X$^+$ is an alkali metal cation or a cationic alkaline earth metal monohydroxide. Thus, X$^+$ may be Na$^+$, K$^+$, [CaOH]$^+$ or [MgOH]$^+$, for instance. Typically, X$^+$ is [CaOH]$^+$. Typically, Z$^{2+}$ is an alkaline earth metal dication. Thus, Z$^{2+}$ may be Ca$^{2+}$ or Mg$^{2+}$, for example. Typically, Z$^{2+}$ is Ca$^{2+}$.

As used herein, the term "sulfonic acid" represents a group of the formula: —S(=O)$_2$OH. As would be understood by the skilled person, a sulfonic acid group (for instance, when employed in the present invention as an adhesive functional group) can exist in protonated and deprotonated forms (for example, —S(=O)$_2$OH and —S(=O)$_2$O$^-$), and in salt forms (for example, —S(=O)$_2$O$^-$X$^+$, wherein X$^+$ is a monovalent cation). Typically, X$^+$ is an alkali metal cation or a cationic alkaline earth metal monohydroxide. Thus, X$^+$ may be Na$^+$, K$^+$, [CaOH]$^+$ or [MgOH]$^+$, for instance.

As used herein, the terms "carboxy", "carboxyl" and "carboxylic acid" each represent a group of the formula: —C(=O)OH, or —COOH. As would be understood by the skilled person, a carboxylic acid group (for instance, when employed in the present invention as an adhesive functional group) can exist in protonated and deprotonated forms (for example, —C(=O)OH and —C(=O)O$^-$), and in salt forms (for example, —C(=O)O$^-$X$^+$, wherein X$^+$ is a monovalent cation). Typically, X$^+$ is an alkali metal cation or a cationic alkaline earth metal monohydroxide. Thus, X$^+$ may be Na$^+$, K$^+$, [CaOH]$^+$ or [MgOH]$^+$, for instance.

As used herein, the term "carboxyl amide" represents a group of formula: —C(O)NH$_2$.

As used herein, the term "sulfonamide" represents a group of formula: —S(O)$_2$NH$_2$.

$C_{1-20}$ alkylene and $C_{1-20}$ alkyl groups as defined herein are either uninterrupted or interrupted by one or more heteroatoms or heterogroups, such as S, O or N(R") wherein R" is H, $C_{1-6}$ alkyl or aryl (typically phenyl), or by one or more arylene (typically phenylene) groups. The phrase "optionally interrupted" as used herein thus refers to a $C_{1-20}$ alkyl group or an alkylene group, as defined above, which is uninterrupted or which is interrupted between adjacent carbon atoms by a heteroatom such as oxygen or sulfur, by a heterogroup such as N(R") wherein R" is H, aryl or $C_1$-$C_6$ alkyl, or by an arylene group. For instance, a $C_{1-20}$ alkyl group such as n-butyl may be interrupted by the heterogroup N(R") as follows: —CH$_2$N(R")CH$_2$CH$_2$CH$_3$, —CH$_2$CH$_2$N(R")CH$_2$CH$_3$, or —CH$_2$CH$_2$CH$_2$N(R")CH$_3$. Similarly, an alkylene group such as n-butylene may be interrupted by the heterogroup N(R") as follows: —CH$_2$N(R")CH$_2$CH$_2$CH$_2$—, —CH$_2$CH$_2$N(R")CH$_2$CH$_2$—, or —CH$_2$CH$_2$CH$_2$N(R")CH$_2$—.

Unless otherwise specified, included in the above are the well known ionic, salt, and solvate forms of those substituents. For example, a reference to carboxylic acid, carboxy or carboxyl group (or the formulae —COOH or —C(=O)OH) also includes the anionic (carboxylate) form (—COO$^-$), a salt or solvate thereof. Similarly, a reference to an amino group includes the protonated form (—N$^+$HR$^1$R$^2$), a salt or solvate of the amino group, for example, a hydrochloride salt. Similarly, a reference to a hydroxyl group also includes the anionic form (—O$^-$), or salt or solvate thereof.

The term "Prot" as used herein, means a protecting group which is a precursor to a —CH=CH$_2$ group. Thus, Prot is any protecting group which is capable of being converted into a —CH=CH$_2$ group by chemical reaction, or any protecting group for which a —CH=CH$_2$ group can be substituted by chemical reaction. Examples of protecting groups "Prot" which are precursors to —CH=CH$_2$ include 7-oxabicyclo[2.2.1]hept-2-yl; organometallic groups, for instance iron- or cobalt-containing organometallic groups; and 1,2-dioxygenated substrates. Typically, Prot is 7-oxabicyclo[2.2.1]hept-2-yl. When Prot is 7-oxabicyclo[2.2.1]hept-2-yl, the group —O—C(=O)-Prot is readily converted into the group —O—C(30)—CH=CH$_2$ by heating (see Example 4 below).

The invention provides a process for producing a substrate having an adhesive surface. The term "adhesive surface", as used herein, refers to a surface of the substrate which is capable of acting as an adhesive. A surface of the substrate which is capable of acting as an adhesive is one which is capable of attachment to the surface of another material, which may be known as an "adherend", such that the substrate and the adherend are held together.

Without wishing to be bound by theory, the attachment of the adhesive surface to the surface of the adherend may be through a physical interaction between the adhesive surface and the adherend (e.g. due to an electrostatic attraction between adhesive and adherend, or an attraction owing to their mutual solubility), through a mechanical interaction between adhesive surface and adherend (e.g. due to mechanical interlocking) or through the formation of chemical bonds between adhesive surface and adherend (e.g. covalent bonds, ionic bonds, hydrogen bonds or other non-covalent bonds).

In the carbene precursor compound of formula (I), used in the process for producing a substrate having an adhesive surface, $W_A$ and, where present, $W_B$ are groups comprising either (i) an adhesive functional group, or (ii) a group which is a precursor of an adhesive functional group.

The term "adhesive functional group", as used herein, refers to a functional group which is capable of interaction with the surface of an adherend, in order to facilitate adhesion of the substrate to the adherend. Certain types of adhesive functional groups are capable of interacting with certain types of adherend by forming covalent or non-covalent chemical bonds, or "cross links", to those adherends. Thus, typically, a covalent bond is formed or a non-covalent interaction occurs between the adhesive functional group and the surface of the adherend. Examples of non-covalent interactions are electrostatic or ionic interactions, hydrogen bonding and Van der Waals forces. In one embodiment, the term "adhesive functional group" is a group which is capable of forming a covalent or non-covalent chemical interaction with an adherend. In another embodiment, the term "adhesive functional group" is a group which is capable of forming a covalent or ionic interaction with an adherend. The mechanisms of formation of chemical bonds between adhesive functional group and adherend include free radical cross linking, ionic cross linking and nucleophilic cross linking. Typically, adhesive functional groups such as hydroxyl, amino and thiol are used for nucleophilic cross linking and ionic cross linking reactions, whereas groups comprising aliphatic carbon-carbon double bonds are typically used for free radical cross linking.

Certain types of adhesive functional groups are capable of interaction with certain types of adherends, in order to aid adhesion of the substrate to those adherends. Thus, by selecting an appropriate adhesive functional group, the substrate in question can be adhered to a particular adherend as desired.

Some adhesive functional groups are capable of modifying certain surface properties of the substrate including dispersability, hydrophobicity, hydrophilicity, oleophobicity and oleophilicity. An adhesive functional group may for instance interact with a particular solvent in such a way that it imparts a particular dispersability in that solvent to the substrate. Similarly, an adhesive functional group may interact with water in such a way that it imparts a particular hydrophilicity or hydrophobicity to the substrate. Thus, by selecting an appropriate adhesive functional group, the dispersability, hyrophobicity, hydrophilicity, oleophobicity and/or oleophilicity of the substrate can be controlled as desired.

Accordingly, in one embodiment of the process of the invention for producing a substrate having an adhesive surface, the process is suitable for producing a substrate which has a desirable dispersability, hydrophobicity, hydrophilicity, oleophobicity and/or oleophilicity.

Adhesive functional groups which may be employed in the present invention include OH, $NH_2$ and SH. Accordingly, $W_A$ or $W_B$ is typically a group which comprises at least one OH, $NH_2$ or SH group. Thus, $W_A$ or $W_B$ can be a single OH, $NH_2$ or SH group, or a group which contains a plurality of OH, $NH_2$ or SH moieties. Thus $W_A$ or $W_B$ may be a polyol, polythiol or a group containing a plurality of amino groups. Typically, $W_A$ or $W_B$ is -$L^2$-OH, -$L^2$-$NH_2$, -$L^2$-SH, $C_{1-20}$ alkyl, $C_{3-20}$ cycloalkyl, $C_{3-20}$ heterocyclyl, aryl or heteroaryl, wherein said $C_{1-20}$ alkyl, $C_{3-20}$ cycloalkyl, $C_{3-20}$ heterocyclyl, aryl and heteroaryl are each substituted by -$L^2$-OH, -$L^2$-$NH_2$ or -$L^2$-SH, wherein said $C_{1-20}$ alkyl is optionally interrupted by N(R"), O, S or arylene, wherein R" is H, $C_{1-6}$ alkyl or aryl, and wherein $L^2$ is a single bond, $C_{1-6}$ alkylene, arylene, -arylene-$C_{1-6}$ alkylene- or -$C_{1-6}$ alkylene-arylene-, wherein each of said $C_{1-6}$ alkylene groups is optionally interrupted by N(R"), O, S or arylene. Thus, in one embodiment, $W_A$ or $W_B$ is a group of the following structure:

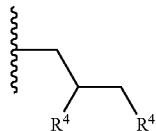

in which each $R^4$, which may be the same or different, is OH, $NH_2$ or SH. Such groups comprising hydroxyl, amino or thiol adhesive functional groups may be used for nucleophilic cross linking and ionic cross linking reactions. Thus, hydroxyl, amino or thiol adhesive functional groups may be used for adhering a substrate to an adherend comprising an unsaturated bond (for instance an adherend which is or comprises an alkene, alkyne or an enol ether) or to an adherend which comprises an alkyl halide, epoxide, alkyl tosylate or equivalent functionality. Such equivalent functionalities would be apparent to one skilled in the art.

Another adhesive functional group which may be employed in the present invention is a group containing an aliphatic carbon-carbon double bond. Accordingly, $W_A$ or $W_B$ is typically a group which comprises at least one aliphatic carbon-carbon double pond. Thus, $W_A$ or $W_B$ can be a group which comprises a single aliphatic carbon-carbon double bond, such as a vinyl group, an acrylonitrile group or an acrylate group, or can be a group which comprises a plurality of aliphatic carbon-carbon double bonds. Thus $W_A$ or $W_B$ may be, or comprise, a polyene, for example a group derived from vinyl norbornene or ethylidene norbornene. $W_A$ or $W_B$ may be a group which comprises one or more groups of the following structure:

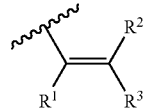

wherein:

$R^1$, $R^2$ and $R^3$, which may be the same or different, are each selected from H, $C_{1-6}$ alkyl, aryl, cyano, amino, $C_{1-10}$ alkylamino, di($C_{1-10}$)alkylamino, arylamino, diarylamino, arylalkylamino, amido, halo, carboxy, ester, $C_{1-6}$ alkoxy, aryloxy, $C_{1-10}$ alkylthio and arylthio. Typically, $R^1$ is H or cyano. Typically, $R^2$ and $R^3$ are independently selected from H, $C_{1-6}$ alkyl and aryl. More typically, $R^2$ and $R^3$ are each H. Typically, $W_A$ or $W_B$ is

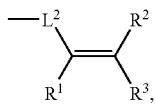

$C_{1-20}$ alkyl, $C_{3-20}$ cycloalkyl, $C_{3-20}$ heterocyclyl, aryl or heteroaryl, wherein said $C_{1-20}$ alkyl, $C_{3-20}$ cycloalkyl, $C_{3-20}$ heterocyclyl, aryl and heteroaryl are each substituted by:

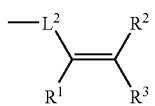

wherein $R^1$, $R^2$ and $R^3$ are as defined above, wherein said $C_{1-20}$ alkyl is optionally interrupted by N(R"), O, S or arylene, wherein R" is H, $C_{1-6}$ alkyl or aryl, and wherein $L^2$ is a single bond, $C_{1-6}$ alkylene, arylene, arylene-$C_{1-6}$ alkylene- or —$C_{1-6}$ alkylene-arylene-, wherein each of said $C_{1-6}$ alkylene groups is optionally interrupted by N(R"), O, S or arylene. Such groups comprising one or more aliphatic carbon-carbon double bonds may be used for free radical cross linking reactions, in order to adhere a substrate to radicals, including carbon-centred and heteroatom-centred (for example, O-, N- or S-centred) radicals. Such groups may also be used for coupling a substrate to an adherend under ionic conditions, in cases where the adherend includes an electrophilic unit such as a carbocation, or a nucleophilic atom such as O, N or S.

$W_A$ or $W_B$ may be a group which comprises one or more groups of the following structure:

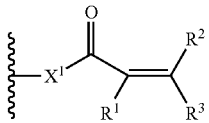

in which X' is a single bond, O, C(R")(R"') or N(R"), wherein R" and R"' are independently selected from H, $C_{1-6}$ alkyl or aryl, and $R^1$, $R^2$ and $R^3$, which may be the same or different, are each selected from H, $C_{1-6}$ alkyl, aryl, cyano, amino, $C_{1-10}$ alkylamino, di($C_{1-10}$)alkylamino, arylamino, diarylamino, arylalkylamino, amido, halo, carboxy, ester, $C_{1-6}$ alkoxy, aryloxy, $C_{1-10}$ alkylthio and arylthio. Typically, R' is H or cyano.

Typically, $R^2$ and $R^3$ are independently selected from H, $C_{1-6}$ alkyl and aryl. More typically, $R^2$ and $R^3$ are each H. Typically, $W_A$ or $W_B$ is:

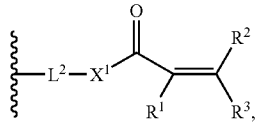

$C_{1-20}$ alkyl, $C_{3-20}$ cycloalkyl, $C_{3-20}$ heterocyclyl, aryl or heteroaryl, wherein said $C_{1-20}$ alkyl, $C_{3-20}$ cycloalkyl, $C_{3-20}$ heterocyclyl, aryl and heteroaryl are each substituted by:

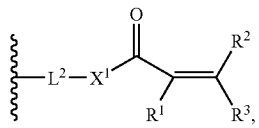

wherein $X^1$, $R^1$, $R^2$ and $R^3$ are as defined above, wherein said $C_{1-20}$ allyl is optionally interrupted by N(R"), O, S or arylene, wherein R" is H, $C_{1-6}$ alkyl or aryl, and wherein $L^2$ is a single bond, $C_{1-6}$ alkylene, arylene, -arylene-$C_{1-6}$ alkylene- or $C_{1-6}$ alkylene-arylene-, wherein each of said $C_{1-6}$ alkylene groups is optionally interrupted by N(R"), O, S or arylene. Such groups may be used for free radical cross linking reactions, in order to adhere a substrate to radicals, including carbon-centred and heteroatom-centred (for example, O-, N- or S-centred) radicals. Such groups may also be used for coupling a substrate to an adherend under ionic conditions, in cases where the adherend includes a nucleophilic atom such as O, N or S. In addition where $X^1$ is O, such groups may be used specifically for acrylate coating adhesion.

Another adhesive functional group which may be employed in the present invention is an epoxide group. Accordingly, $W_A$ or $W_B$ is typically a group which comprises at least one epoxide group. Thus, $W_A$ or $W_B$ can be a group which comprises a single epoxide group, or a group which comprises a plurality of epoxide groups. $W_A$ or $W_B$ may be a group which comprises one or more groups of the following structure:

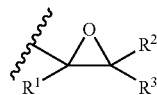

in which $R^1$, $R^2$ and $R^3$, which may be the same or different, are each selected from H, $C_{1-6}$ alkyl, aryl, cyano, amino, $C_{1-10}$ alkylamino, di($C_{1-10}$)alkylamino, arylamino, diarylamino, arylalkylamino, amido, halo, carboxy, ester, $C_{1-6}$ alkoxy, aryloxy, $C_{1-10}$ alkylthio and arylthio. Typically, $R^1$, $R^2$ and $R^3$ are independently selected from H, $C_{1-6}$ alkyl and aryl. More typically, $R^1$, $R^2$ and $R^3$ are each H. Typically, $W_A$ or $W_B$ is

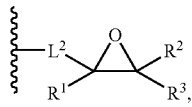

$C_{1-20}$ alkyl, $C_{3-20}$ cycloalkyl, $C_{3-20}$ heterocyclyl, aryl or heteroaryl, wherein said $C_{1-20}$ alkyl, $C_{3-20}$ cycloalkyl, $C_{3-20}$ heterocyclyl, aryl and heteroaryl are each substituted by

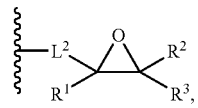

wherein said $C_{1-20}$ alkyl is optionally interrupted by N(R"), O, S or arylene, wherein R" is H, $C_{1-6}$ alkyl or aryl, and wherein $R^1$, $R^2$ and $R^3$ are as defined above and $L^2$ is a single bond, $C_{1-6}$ alkylene, arylene, -arylene-$C_{1-6}$ alkylene- or -$C_{1-6}$ alkylene-arylene-, wherein each of said $C_{1-6}$ alkylene groups is optionally interrupted by N(R"), O, S or arylene wherein R" is as defined above. Such groups comprising one or more epoxide groups may be used for nucleophilic cross linking reactions operated under acidic or basic conditions, in order to adhere a substrate to an adherend which comprises a group that includes a nucleophilic atom such as O, N or S, or to an adherend which comprises another nucleophilic species such as a carbanion (or an organometallic derivative of a carbanion) or an enolate (or an equivalent of an enolate).

Another adhesive functional group which may be employed in the present invention is a group that is capable of adhering to a metal or a metal alloy. Yet another adhesive functional group which may be employed in the present invention is a group that is capable of adhering to a metal ion or a metal salt. Accordingly, $W_A$ or $W_B$ is typically a group which comprises at least one group, denoted "M", that is capable of adhering either to a metal, a metal alloy, or a metal ion or salt. Thus, $W_A$ or $W_B$ can be a group which comprises a single "M" group or a group which comprises a plurality of "M" groups. Typically, $W_A$ or $W_B$ is -$L^2$-M, $C_{1-20}$ alkyl, $C_{3-20}$ cycloalkyl, $C_{3-20}$ heterocyclyl, aryl or heteroaryl, wherein said $C_{1-20}$ alkyl, $C_{3-20}$ cycloalkyl, $C_{3-20}$ heterocyclyl, aryl and heteroaryl are each substituted by -$L^2$-M, wherein said $C_{1-20}$ alkyl is optionally interrupted by N(R"), O, S or arylene, wherein R" is H, $C_{1-6}$ alkyl or aryl, and wherein $L^2$ is a single bond, $C_{1-6}$ alkylene, arylene, -arylene-$C_{1-6}$ alkylene- or —$C_{1-6}$ alkylene-arylene-, wherein each of said $C_{1-6}$ alkylene groups is optionally interrupted by N(R"), O, S or arylene and M is as defined above. The groups "M" that are capable of adhering either to a metal, a metal alloy, metal ion or salt are typically used in order to adhere a substrate to a metal salt, a metal other than an alkali metal or an alkaline earth metal, or an alloy of any metal other than an alkali metal or an alkaline earth metal. Typically, the metal salt is a calcium salt. Typically, the metal other than an alkali metal or an alkaline earth metal or alloy is selected from: Al, Cu, Pb, Au, Ag, Pt, Pd, Sn, Pb and alloys of those metals. The metal may also include group IV (group 14) elements, for example Ge, Si, Pb and C and alloys of those elements. The metallisation of polymer surfaces of relevance in printed circuit board and electronic technology. Thus, adhesion of such metals or alloys to substrates may be of use to the electronics industry, for example in the manufacture of printed circuit boards.

Typically, M is a group comprising one or more phosphonic acid groups. Accordingly, $W_A$ or $W_B$ is typically a group which comprises at least one phosphonic acid group. Thus, $W_A$ or $W_B$ can be a group which comprises a single phosphonic acid group, or a group which comprises a plurality of phosphonic acid groups, such as a bis-phosphonic acid group or a polyphosphonic acid group. Suitable M groups include $P(=O)(OH)_2$ and

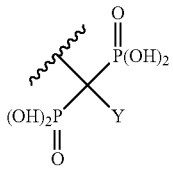

wherein Y is H, $C_{1-6}$ alkyl, aryl, —OH, —SH or $NH_2$. Typically, $W_A$ or $W_B$ is $-L^2-P(=O)(OH)_2$, $C_{1-20}$ alkyl, $C_{3-20}$ cycloalkyl, $C_{3-20}$ heterocyclyl, aryl or heteroaryl, wherein said $C_{1-20}$ alkyl, $C_{3-20}$ cycloalkyl, $C_{3-20}$ heterocyclyl, aryl and heteroaryl are each substituted by $-L^2-P(=O)(OH)_2$, wherein said $C_{1-20}$ alkyl is optionally interrupted by N(R"), O, S or arylene, and wherein $L^2$ is a single bond, $C_{1-6}$ alkylene, arylene, -arylene-$C_{1-4}$ alkylene- or —$C_{1-6}$ alkylene-arylene-, wherein each of said $C_{1-6}$ alkylene groups is optionally interrupted by N(R"), O, S or arylene. Groups comprising phosphonic acid moieties may be used for metal adhesion, or for adhesion through an ion exchange reaction or an ionic cross linking reaction.

Alternatively, M is a group comprising one or more sulfonic acid groups. Accordingly, $W_A$ or $W_B$ is typically a group which comprises at least one sulfonic acid group. Thus, $W_A$ or $W_B$ can be a group which comprises a single sulfonic acid group, or a group which comprises a plurality of sulfonic acid groups, such as a bis-sulfonic acid group or a polysulfonic acid group. Suitable M groups include —$S(=O)_2(OH)$ and —$CY[S(O)_2(OH)]_2$, wherein Y is H, $C_{1-6}$ alkyl, aryl, —OH, —SH or $NH_2$. Typically, $W_A$ or WS is $-L^2-S(=O)_2(OH)$, $C_{1-20}$ alkyl, $C_{3-20}$ cycloalkyl, $C_{3-20}$ heterocyclyl, aryl or heteroaryl, wherein said $C_{1-20}$ alkyl, $C_{3-20}$ cycloalkyl, $C_{3-20}$ heterocyclyl, aryl and heteroaryl are each substituted by $-L^2-S(=O)_2(OH)$, wherein said $C_{1-20}$ alkyl is optionally interrupted by N(R"), O, S or arylene, and wherein $L^2$ is a single bond, $C_{1-6}$ alkylene, arylene, -arylene-$C_{1-6}$ alkylene- or —$C_{1-6}$ alkylene-arylene-, wherein each of said $C_{1-6}$ alkylene groups is optionally interrupted by N(R"), O, S or arylene. Groups comprising sulfonic acid moieties may be used for metal adhesion, or for adhesion through an ion exchange reaction or an ionic cross linking reaction.

Alternatively, M is a group comprising one or more carboxylic acid groups. Accordingly, $W_A$ or $W_B$ is typically a group which comprises at least one carboxylic acid group. Thus, $W_A$ or $W_B$ can be a group which comprises a single carboxylic acid group, or a group which comprises a plurality of carboxylic acid groups, such as a bis-carboxylic acid group or a polycarboxylic acid group. Suitable M groups include —C(=O)OH and —$CY(COOH)_2$, wherein Y is H, $C_{1-6}$ alkyl, aryl, —OH, —SH or $NH_2$. Typically, $W_A$ or $W_B$ is $-L^2$-COOH, $C_{1-20}$ alkyl, $C_{3-20}$ cycloalkyl, $C_{3-20}$ heterocyclyl, aryl or heteroaryl, wherein said $C_{1-20}$ alkyl, $C_{3-20}$ cycloalkyl, $C_{3-20}$ heterocyclyl, aryl and heteroaryl are each substituted by $-L^2$-COOH, wherein said $C_{1-20}$ alkyl is optionally interrupted by N(R"), O, S or arylene, and wherein $L^2$ is a single bond, $C_{1-6}$ alkylene, arylene, -arylene-$C_{1-6}$ alkylene- or —$C_{1-6}$ alkylene-arylene-, wherein each of said $C_{1-6}$ alkylene groups is optionally interrupted by N(R"), O, S or arylene. Groups comprising carboxylic acid moieties may be used for metal adhesion, or for adhesion through an ion exchange reaction or anionic cross-linking reaction.

The adhesive functional groups defined in the preceding paragraphs, which comprise one or more phosphonic acid, sulfonic acid or carboxylic acid groups, can be used for adhesion of the substrate to biological cells or tissue. Adhering a substrate to cells or tissue is of use in tissue engineering applications, applications involving cell cultures and other medical applications. Without wishing to be bound by theory, it is thought that the acidic adhesive functional groups serve to modify the free energy of the surface of the substrate so that the surface is more hydrophilic. That increased hydrophilicity makes the substrate more biocompatible and thus more attractive to biological tissue and cells. This promotes adhesion of the substrate to cells or tissue.

Adhesion of the substrate to cells or tissue is typically enhanced if the phosphonic acid, sulfonic acid or carboxylic acid group is present in the form of a salt with a metal counterion, particularly in the form of a calcium salt. Accordingly, in one embodiment $W_A$ or $W_B$ comprises a group which is a salt of a phosphonic acid group, a salt of a sulfonic acid group or a salt of a carboxylic acid group. Typically, the salt is a calcium salt. Accordingly, $W_A$ or $W_B$ may comprise a group which is a calcium salt of a phosphonic acid group, a calcium salt of a sulfonic acid group or a calcium salt of a carboxylic acid group. More typically, $W_A$ or $W_B$ comprises a group which is a calcium salt of a phosphonic acid group. The use of calcium salts of phosphonic, sulfonic or carboxylic acid group can achieve enhanced adhesion of the substrate to cells or tissue compared with the use of the corresponding free acid groups. Suitable groups "M" as defined above thus include salts, typically calcium salts, of groups of any of the following structures: —$P(=O)(OH)_2$; —$C(Y)[P(=O)(OH)_2]_2$; —C(=O)OH; —$CY(COOH)_2$; —$S(O)_2OH$ and —$CY[S(=O)_2OH]_2$, wherein Y is H, $C_{1-6}$ alkyl, aryl, —OH, —SH or $NH_2$. Accordingly, $W_A$ or $W_B$ is typically $-L^2$-M, $C_{1-20}$ alkyl, $C_{3-20}$ cycloalkyl, $C_{3-20}$ heterocyclyl, aryl or heteroaryl, wherein said $C_{1-20}$ alkyl, $C_{3-20}$ cycloalkyl, $C_{3-20}$ heterocyclyl, aryl and heteroaryl are each substituted by $-L^2$-M; wherein said $C_{1-20}$ alkyl is optionally interrupted by N(R"), O, S or arylene; wherein $L^2$ is a single bond, $C_{1-6}$ alkylene, arylene, -arylene-$C_{1-6}$ alkylene- or —$C_{1-6}$ alkylene-arylene-; wherein each of said $C_{1-6}$ alkylene groups is optionally interrupted by N(R"), O, S or arylene; and wherein M is selected from a salt, typically a calcium salt, of a group having any one of the following structures: —$P(=O)(OH)_2$; —$C(Y)[P(=O)(OH)_2]_2$; —C(=O)OH; —$CY(COOH)_2$; —$S(O)_2OH$ and —$CY[S(=O)_2OH]_2$, wherein Y is H, $C_{1-6}$ alkyl, aryl, —OH, —SH or $NH_2$. Typically, M is —$P(=O)(OH)O^-[CaOH]^+$ or —$C(Y)\{P(=O)(OH)O^-[CaOH]^+\}_2$. More typically, M is —$P(=O)(OH)O^-[CaOH]^+$.

Phosphonic acid, sulfonic acid or carboxylic acid groups can be converted into the corresponding salt forms using well-known methods, for instance by treatment with the appropriate base. For example, phosphonic acid groups, sulfonic acid groups or carboxylic acid groups can be converted into calcium salts of those groups by treatment with calcium hydroxide. In one embodiment of the process of the invention for producing a substrate having an adhesive surface, M is a group having the structure —$P(=O)(OH)_2$; —$C(Y)[P(=O)(OH)_2]_2$; —C(=O)OH; —$CY(COOH)_2$; —$S(=O)_2OH$ or —$CY[S(=O)_2OH]_2$, wherein Y is H, $C_{1-6}$ alkyl, aryl, —OH, —SH or $NH_2$, and the process further comprises the step of converting said group into a salt of said group. Typically, the salt is a calcium salt. More typically, M is —$P(=O)(OH)_2$ and the salt is —$P(=O)(OH)O^-[CaOH]^+$.

Alternatively, M may be a group comprising one or more sulfonamide groups. Accordingly, $W_A$ or $W_B$ is typically a group which comprises at least one sulfonamide group. Thus, $W_A$ or $W_B$ can be a group which comprises a single sulfonamide group, or a group which comprises a plurality of sulfonamide groups, such as a bis-sulfonamide group or a polysulfonamide group. Suitable M groups include —(=O)$_2$NH$_2$ and —CY[S(=O)$_2$NH$_2$]$_2$, wherein Y is H, C$_{1-6}$ alkyl, aryl, —OH, —SH or NH$_2$. Typically, W$_A$ or W$_B$ is -L$^2$-S(=O)$_2$ NH$_2$, C$_{1-20}$ alkyl, C$_{3-20}$ cycloalkyl, C$_{3-20}$ heterocyclyl, aryl or heteroaryl, wherein said C$_{1-20}$ alkyl, C$_{3-20}$ cycloalkyl, C$_{3-20}$ heterocyclyl, aryl and heteroaryl are each substituted by -L$^2$-S(=O)$_2$NH$_2$, wherein said C$_{1-20}$ alkyl is optionally interrupted by N(R"), O, S or arylene, and wherein L$^2$ is a single bond, C$_{1-6}$ alkylene, arylene, -arylene-C$_{1-6}$ alkylene- or —C$_{1-6}$ alkylene-arylene-, wherein each of said C$_{1-6}$ alkylene groups is optionally interrupted by N(R"), O, S or arylene. Groups comprising sulfonamide moieties may be used for metal adhesion, or for adhesion through an ion exchange reaction or an ionic cross linking reaction.

Alternatively, M is a group comprising one or more carboxyl amide groups. Accordingly, W$_A$ or W$_B$ is typically a group which comprises at least one carboxyl amide group. Thus, W$_A$ or W$_B$ can be a group which comprises a single carboxyl amide group, or a group which comprises a plurality of carboxyl amide groups, such as a bis-carboxyl amide group or a poly(carboxyl amide) group. Suitable M groups include —C(=O)NH$_2$ and —CY[C(=O)NH$_2$]$_2$, wherein Y is H, C$_{1-6}$ alkyl, aryl, —OH, —SH or NH$_2$. Typically, W$_A$ or W$_B$ is -L$^2$-C(=C)NH$_2$, C$_{1-20}$ alkyl, C$_{3-20}$ cycloalkyl, C$_{3-20}$ heterocyclyl, aryl or heteroaryl, wherein said C$_{1-20}$ alkyl, C$_{3-20}$ cycloalkyl, C$_{3-20}$ heterocyclyl, aryl and heteroaryl are each substituted by -L$^2$-C(=O)NH$_2$, wherein said C$_{1-20}$ alkyl is optionally interrupted by N(R"), O, S or arylene, and wherein L$^2$ is a single bond, C$_{1-6}$ alkylene, arylene, -arylene-C$_{1-6}$ alkylene- or —C$_{1-6}$ alkylene-arylene-, wherein each of said C$_{1-6}$ allylene groups is optionally interrupted by N(R"), O, S or arylene. Groups comprising carboxyl amide moieties may be used for metal adhesion, or for adhesion through an ion exchange reaction or an ionic cross linking reaction.

In the carbene precursor compounds of formula (I), used in the process for producing a substrate having an adhesive surface, W$_A$ or, where present, W$_B$, may comprise a group which is a precursor of an adhesive functional group.

The term "group which is a precursor of an adhesive functional group", as used herein, refers to a group which may be converted into an adhesive functional group. Thus, a group which is a precursor of an adhesive functional group may be a protected version of the adhesive functional group, wherein deprotection of that group yields the corresponding adhesive functional group. Alternatively (or additionally), a group which is a precursor of an adhesive functional group may one which can be converted into an adhesive functional group in a single synthetic step.

Typically, W$_A$ or, where present, W$_B$, comprises a group which is a precursor of an adhesive functional group when it is necessary to protect the adhesive functional group during step (b) of the process of the invention for producing a substrate having an adhesive surface (i.e. during the step in which the carbene reactive intermediate is generated for reaction with the substrate). Then, once the reaction between the carbene reactive intermediate and the substrate is complete, the group which is a precursor of an adhesive functional group may be converted into the corresponding adhesive functional group.

Alternatively, the group which is a precursor of an adhesive functional group may be converted into the corresponding adhesive functional group during step (b) of the process. Thus, in one embodiment of the process of the invention for producing a substrate having an adhesive surface, either W$_A$ or W$_B$ comprises a group which is a precursor of an adhesive functional group, and step (b), of generating a carbene reactive intermediate from the carbene precursor so that it reacts with the substrate to functionalise the surface, is combined with step (c), of converting said group which is a precursor into an adhesive functional group.

A group which is a precursor of an adhesive functional group which may be employed in the present invention is a group having the following structure:

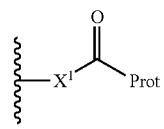

wherein X$^1$ is a single bond, C(R")(R'''), N(R") or O, wherein R" and R''' are independently selected from H, C$_{1-6}$ alkyl or aryl, and Prot is a protecting group which is a precursor to a —CH=CH$_2$ group. Accordingly, W$_A$ or W$_B$ is typically a group which comprises at least one group having the structure:

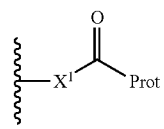

wherein X$^1$ and Prot are as defined above. Thus, W$_A$ or W$_B$ can be a single group having that structure —X$^1$—C(=O)-Prot or a group which contains a plurality groups having the structure —X$^1$—C(=O)-Prot. Typically, W$_A$ or W$_B$ is

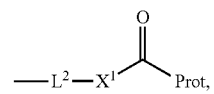

C$_{1-20}$ alkyl, C$_{3-20}$ cycloalkyl, C$_{3-20}$ heterocyclyl, aryl or heteroaryl, wherein said C$_{1-20}$ alkyl, C$_{3-20}$ cycloalkyl, C$_{3-20}$ heterocyclyl, aryl and heteroaryl are each substituted by

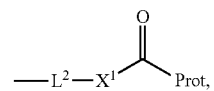

wherein said C$_{1-20}$ alkyl is optionally interrupted by N(R"), O, S or arylene, wherein R" is H, C$_{1-6}$ alkyl or aryl, and wherein L$^2$ is a single bond, C$_{1-6}$ alkylene, arylene, -arylene-C$_{1-6}$ alkylene- or —C$_{1-6}$ alkylene-arylene-, wherein each of said C$_{1-6}$ alkylene groups is optionally interrupted by N(R"), O, S or arylene.

Such groups comprising

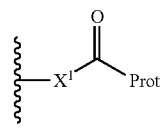

can be converted into an adhesive functional group having the following structure:

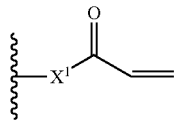

in which $X^1$ is as defined above. Thus, typically, in the process of the invention for producing a substrate having an adhesive surface, either $W_A$ or $W_B$ comprises a group having the structure:

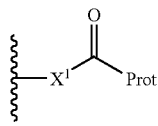

wherein $X^1$ and Prot are as defined above, and step (c) of the process comprises converting said group into an adhesive functional group having the structure:

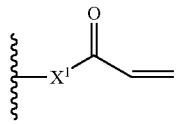

in which $X^1$ is as defined above. Typically, the conversion is effected by electromagnetic irradiation, ultrasonic irradiation or thermal irradiation. More typically, the conversion is effected by thermal irradiation, for instance by heating. Typically, steps (b) and (c) are combined such that conversion into the adhesive functional group takes place during step (b), in which the carbene reactive intermediate is generated for reaction with the substrate.

Other groups which may be employed as precursors of adhesive functional groups include —OH and —NH(R"), wherein R" is selected from H, $C_{1-6}$ alkyl or aryl. Such groups may be converted into a group of the following structure:

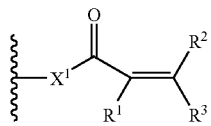

in which $X^1$ is O or N(R"). Thus, in one embodiment of the process of the present invention for producing a substrate having an adhesive surface, either $W_A$ or $W_B$ comprises a group which is a precursor of an adhesive functional group, which group which is a precursor is selected from —OH and —NH(R"), wherein R" is selected from H, $C_{1-6}$ alkyl or aryl, wherein step (c) of the process comprises reacting said —OH or —NH(R") with Hal-C(O)C($R^1$)=$CR^2R^3$, wherein Hal is a suitable leaving group and $R^1$, $R^2$ and $R^3$, which may be the same or different, are each selected from H, $C_{1-6}$ alkyl, aryl, cyano, amino, $C_{1-10}$ alkylamino, di($C_{1-10}$)alkylamino, arylamino, diarylamino, arylalkylamino, amido, halo, carboxy, ester, $C_{1-6}$ alkoxy, aryloxy, $C_{1-10}$ alkylthio and arylthio, thereby converting said —OH or —NH(R") into an adhesive functional group having the following structure:

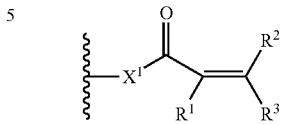

in which $X^1$ is O or N(R"). Typically, $R^1$ is H or cyano. Typically, $R^2$ and $R^3$ are each H. Typically, Hal is a halo group, for instance Cl, Br or I. Alternatively, Hal may be any other suitable leaving group which, for reacting said —OH or —NH(R") with Hal-C(O)C($R^1$)=$CR^2R^3$, is functionally equivalent to a halo group such as Cl, Br or I.

Other groups which may be employed as precursors of adhesive functional groups include groups comprising an aliphatic carbon-carbon double bond. The aliphatic carbon-carbon double bond(s) of such groups can (each) be converted into an epoxide adhesive functional group. Thus, in one embodiment of the process of the present invention for producing a substrate having an adhesive surface, either $W_A$ or $W_B$ comprises a group which is a precursor of an adhesive functional group, which group which is a precursor contains an aliphatic carbon-carbon double bond, wherein step (c) of the process comprises oxidising said aliphatic carbon-carbon double bond to form an epoxide group, thereby converting said group which is a precursor into an epoxide adhesive functional group. Typically, the group which is a precursor of an adhesive functional group is of the following structure:

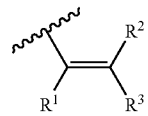

in which $R^1$, $R^2$ and $R^3$, which may be the same or different, are each selected from H, $C_{1-6}$ alkyl, aryl, cyano, amino, $C_{1-10}$ alkylamino, di($C_{1-10}$)alkylamino, arylamino, diarylamino, arylalkylamino, amido, halo, carboxy, ester, $C_{1-6}$ alkoxy, aryloxy, $C_{1-10}$ alkylthio and arylthio; and said epoxide adhesive functional group is of the following structure:

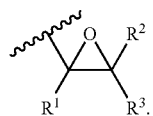

Typically, $R^1$, $R^2$ and $R^3$ are independently selected from H, $C_{1-6}$ alkyl and aryl. More typically, $R^1$, $R^2$ and $R^3$ are each H.

Other groups which may be employed as precursors of adhesive functional groups include groups (denoted herein "M") which are precursors of groups that are capable of adhering to a metal, a metal alloy or a metal ion or salt. Thus, typically, either $W_A$ or $W_B$ of the carbene precursor compounds of the invention comprises a group which is a precursor of a group that is capable of adhering to a metal, metal alloy, or a metal salt or ion. Accordingly, $W_A$ or Ws is typically a group which comprises at least one group, denoted "M", that is a precursor of a group that is capable of adhering to a metal, a metal alloy or a metal ion or salt. Thus, $W_A$ or $W_B$ can be a group which comprises a single "M" group or a group which comprises a plurality of "M" groups. Typically, $W_A$ or $W_B$ is $-L^2-M$, $C_{1-20}$ alkyl, $C_{3-20}$ cycloalkyl, $C_{3-20}$ heterocyclyl, aryl or heteroaryl, wherein said $C_{1-20}$ alkyl, $C_{3-20}$ cycloalkyl, $C_{3-20}$ heterocyclyl, aryl and heteroaryl are each substituted by $-L^2-M$, wherein said $C_{1-20}$ alkyl is optionally interrupted by N(R"), O, S or arylene, wherein R" is H, $C_{1-6}$ alkyl or aryl, and wherein $L^2$ is a single bond, $C_{1-6}$ alkylene, arylene, -arylene-$C_{1-6}$ alkylene- or —$C_{1-6}$ alkylene-arylene-, and wherein each of said $C_{1-6}$ alkylene groups is optionally interrupted by N(R"), O, S or arylene.

Typically, said group M which is a precursor of a group that is capable of adhering to a metal, a metal alloy or a metal salt is either $P(=O)(OR^4)_2$ or:

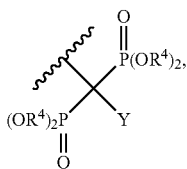

wherein $R^4$ is $C_{1-6}$ alkyl or aryl; and Y is H, $C_{1-6}$ alkyl, aryl, —OH, —SH or $NH_2$. Those groups may be converted into the corresponding phosphonic acid groups. If required, the resulting phosphonic acid groups can be converted into salts (for instance, calcium salts) of those phosphonic acid groups.

In one embodiment of the process of the present invention for producing a substrate having an adhesive surface, either $W_A$ or $W_B$ comprises a group which is a precursor of a group that is capable of adhering to a metal, a metal alloy or a metal salt, wherein step (c) of the process comprises converting said group which is a precursor into a group that is capable of adhering to a metal, a metal alloy or a metal salt. Typically, said group which is a precursor of a group that is capable of adhering to a metal, a metal alloy or a metal salt is either $P(=O)(OR^4)_2$ or:

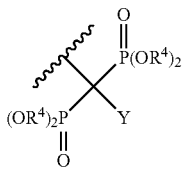

and step (c) of the process comprises converting said group which is a precursor into the corresponding phosphonic acid group having the structure $-P(=O)(OH)_2$ or:

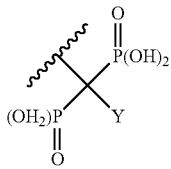

wherein $R^4$ is $C_{1-6}$ alkyl or aryl; and Y is H, $C_{1-6}$ alkyl, aryl, —OH, —SH or $NH_2$. The process may further comprise the step of: (d) converting said phosphonic acid group having the structure $-P(=O)(OH)_2$ or:

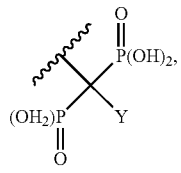

wherein $R^4$ is $C_{1-6}$ alkyl or aryl and Y is H, $C_{1-6}$ alkyl, aryl, —OH, —SH or $NH_2$, into a salt of said phosphonic acid group. Typically, said salt is a calcium salt. More typically, the phosphonic acid group has the structure $-P(=O)(OH)_2$ and the salt has the structure $-P(=O)(OH)O^-[CaOH]^+$.

Typically, in the compounds of the invention of formula (I), $W_A$ and $W_B$ are independently selected from:

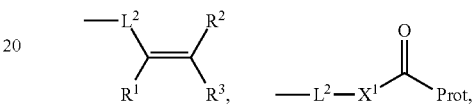

$-L^2-OH$, $-L^2-NH_2$, $-L^2-M$, $C_{1-20}$ alkyl, $C_{3-20}$-cycloalkyl, $C_{3-20}$ heterocyclyl, aryl and heteroaryl, wherein said $C_{1-20}$ alkyl, $C_{3-20}$ cycloalkyl, $C_{3-20}$ heterocyclyl, aryl and heteroaryl are each substituted by one or more groups selected from:

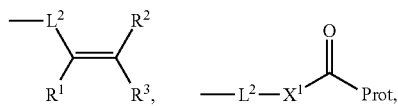

$-L^2-OH$, $-L^2-NH_2$, $-L^2-SH$ and $-L^2-M$, and wherein said $C_{1-20}$ alkyl is optionally interrupted by N(R"), O, S or arylene, wherein R" is as defined in claim 1;

$X^1$ is a single bond, C(R")(R'''), N(R") or O, wherein R" is as defined in claim 1 and R''' is H, $C_{1-6}$ alkyl or aryl;

Prot is a protecting group which is a precursor to a —CH=$CH_2$ group;

$L^2$ is a single bond, $C_{1-6}$ alkylene, arylene, -arylene-$C_{1-6}$ alkylene- or —$C_{1-6}$ alkylene-arylene-, wherein each of said $C_{1-6}$ alkylene groups is optionally interrupted by N(R"), O, S or arylene, wherein R" is as defined in claim 1, provided that when $L^2$ is a single bond the groups

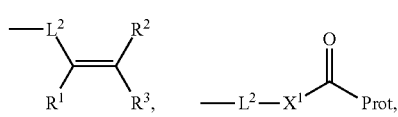

$-L^2-OH$, $-L^2-NH_2$ and $-L^2-SH$ may not be bonded directly to X;

$R^1$, $R^2$ and $R^3$, which may be the same or different, are each selected from H, alkyl, aryl, cyano, amino, $C_{1-10}$ alkylamino, di($C_{1-10}$)alkylamino, arylamino, diarylamino, arylalkylamino, amido, halo, carboxy, ester, $C_{1-6}$ alkoxy, aryloxy, $C_{1-10}$ alkylthio and arylthio; and M is selected from a group that is capable of adhering to a metal, a metal alloy, or a metal salt, and a group which is a precursor of a group that is capable of adhering to a metal, metal alloy or a metal salt. Such compounds may be used in the process of the invention for producing a substrate having an adhesive surface, provided that where $W_A$ or $W_B$ comprises the group:

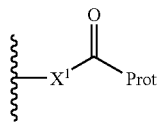

step (c) of the process comprises converting said group into one of the following structure:

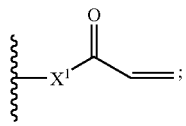

and provided that where $W_A$ or $W_B$ comprises a group which is a precursor of a group that is capable of adhering to a metal, metal alloy or a metal salt, step (c) of the process comprises converting said group which is a precursor into a group that is capable of adhering to a metal, a metal alloy or a metal salt. Typically, $R^1$ is H or cyano. Typically, $R^2$ and $R^3$ are independently selected from H, $C_{1-6}$ alkyl and aryl. More typically, $R^2$ and $R^3$ are each H.

The substrates of the invention having a functionalised surface are functionalised with one or more groups of the following formula (II):

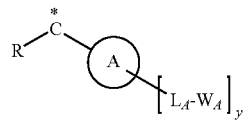

wherein R, *, A, $L_A$, $W_A$ and y are as defined above.

In the substrates of the invention having a functionalised surface, the groups $W_A$ and $W_B$ comprise one or more adhesive functional groups or one or more groups which are precursors of adhesive functional groups. Where $W_A$ or $W_B$ comprises a group which is a precursor of adhesive functional group, it is understood that the substrate may be treated in order to convert that group into the corresponding adhesive functional group. In one embodiment of the substrate of the invention having a functionalised surface, M is selected from: —P(=O)(OR$^4$)$_2$; —P(=O)(OH)$_2$ or a salt thereof;

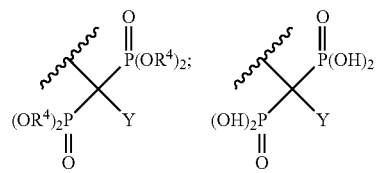

or a salt thereof; —C(=O)OH or a salt thereof; —CY(COOH)$_2$ or a salt thereof; —S(=O)$_2$OH or a salt thereof; —CY[S(=O)$_2$OH]$_2$ or a salt thereof; —C(=O)NH$_2$; —CY[C(=O)NH$_2$]2; —S(=O)$_2$NH$_2$; and —CY[S(=O)$_2$NH$_2$]2 wherein $R^4$ is $C_{1-6}$ alkyl or aryl; and Y is H, $C_{1-6}$ alkyl, aryl, —OH, —SH or NH$_2$. In one embodiment, M is a calcium salt of a group having any one of the following structures: —P(=O)(OH)$_2$, -C(=O)OH, —CY(COOH)$_2$, —S(=O)$_2$OH, —CY[S(=O)$_2$OH]$_2$ and:

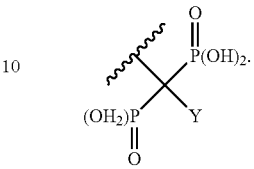

Typically, the calcium salt is —P(=O)(OH)O$^-$[CaOH]$^+$.

Typically, said group containing an aliphatic carbon-carbon double bond of the substrate of the invention having a functionalised surface is selected from:

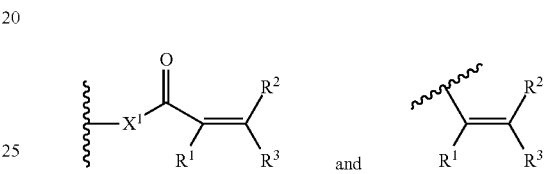

wherein $R^1$, $R^2$ and $R^3$, which may be the same or different, are each selected from H, $C_{1-6}$ alkyl, aryl, cyano, amino, $C_{1-10}$ alkylamino, di($C_{1-10}$)alkylamino, arylamino, diarylamino, arylalkylamino, amido, halo, carboxy, ester, $C_{1-6}$ alkoxy, aryloxy, $C_{1-10}$ alkylthio and arylthio; and $X^1$ is a single bond, O, N(R") or C(R")(R'"), wherein R" and R'" are independently selected from H, $C_{1-6}$ alkyl and aryl.

Typically, said group containing an epoxide group of the substrate of the invention having a functionalised surface has the following structure:

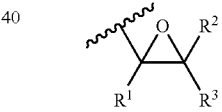

in which $R^1$, $R^2$ and $R^3$, which may be the same or different, are each selected from H, $C_{1-6}$ alkyl, aryl, cyano, amino, $C_{1-10}$ alkylamino, di($C_{1-10}$)alkylamino, arylamino, diarylamino, arylalkylamino, amido, halo, carboxy, ester, $C_{1-6}$ alkoxy, aryloxy, $C_{1-10}$ alkylthio and arylthio.

More typically, $W_A$ and $W_B$ of the substrate of the invention having a functionalised surface are independently selected from:

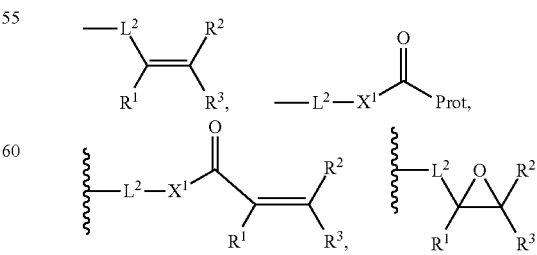

-L$^2$-NH$_2$, -L$^2$-SH, -L$^2$-M, $C_{1-20}$ alkyl, $C_{3-20}$ cycloalkyl, $C_{3-20}$ heterocyclyl, aryl and heteroaryl, wherein said $C_{1-20}$ alkyl, $C_{3-20}$ cycloalkyl, $C_{3-20}$ heterocyclyl, aryl and heteroaryl are each substituted by one or more groups selected from:

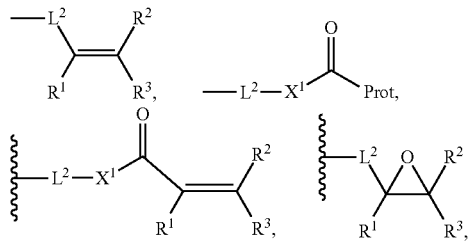

-$L^2$-OH, -$L^2$-NH$_2$, -$L^2$-SH and -$L^2$-M, and wherein said $C_{1-20}$ alkyl is optionally interrupted by N(R"), O, S or arylene, wherein R" is as defined above;

$X^1$ is a single bond, C(R")(R'"), N(R") or O, wherein R" and R'" are as defined above;

Prot is a protecting group which is a precursor to a —CH=CH$_2$ group;

$L^2$ is a single bond, $C_{1-6}$ alkylene, arylene, -arylene-$C_{1-6}$ alkylene- or —$C_{1-6}$ alkylene-arylene-, wherein each of said $C_{1-6}$ alkylene groups is optionally interrupted by N(R"), O, S or arylene wherein R" is as defined in claim 1;

$R^1$, $R^2$ and $R^3$, which may be the same or different, are each selected from H, $C_{1-6}$ alkyl, aryl, cyano, amino, $C_{1-10}$ alkylamino, di($C_{1-10}$)alkylamino, arylamino, diarylamino, arylalkylamino, amido, halo, carboxy, ester, $C_{1-6}$ alkoxy, aryloxy, $C_{1-10}$ alkylthio and arylthio; and M is as defined hereinbefore. Typically, $R^1$ is H or cyano. Typically, $R^2$ and $R^3$ are independently selected from H, $C_{1-6}$ alkyl and aryl. More typically, $R^2$ and $R^3$ are each H.

The carbene precursor compounds of formula (I) used in the process of the invention for producing a substrate having an adhesive surface are typically other than each of the following compounds:

1-{2-[4-(diazo-phenyl-methyl)-benzyloxy]-ethyl}-3-phenyl urea, 4-([N-ethyl-N-phenyl-2-aminoethyl]oxymethyl) phenyl phenyl diazomethane, bis-4,4'-N,N-dimethylamino diphenyldiazomethane, 4-([3,4-dimethoxyphenyl]oxymethyl)phenyl phenyl diazomethane and 4-([3-N,N-diethylaminophenyl]oxymethyl)phenyl phenyl diazomethane.

In the carbene precursor compound of formula (I) used in the process of the invention for producing a substrate having an adhesive surface, the corresponding substrates of the invention, and the substrates of the invention which are functionalised with a group of formula (II), -$L_A$-$W_A$ and, where present, -$L_A$-$W_B$, are typically other than —NMe$_2$.

Typically, -$L_A$-$W_A$ and, where present, -$L_A$-$W_B$, are other than —N=N—Ar$^P$, wherein Ar$^P$ is an unsubstituted or substituted phenyl group. Typically, Ar$^P$ is:

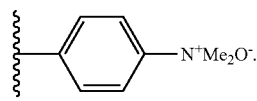

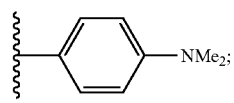

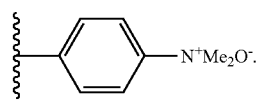

Typically, -$L_A$-$W_A$ and, where present, -$L_A$-$W_B$, are other than —CH$_2$OR$^{QQ}$ wherein R$^{QQ}$ is N-ethyl-N-phenyl-2-aminoethyl, 3,4-dimethoxyphenyl or 3-N,N-dimethylaminophenyl.

Typically, -$L_A$-$W_A$ and, where present, -$L_A$-$W_B$, are other than —N$^+$Me$_2$O$^-$.

Typically, -$L_A$-$W_A$ and, where present, -$L_A$-$W_B$, are other than —CH$_2$O(CH$_2$)$_2$N(H)C(O)N(H)Ph.

Typically, -$L_A$-$W_A$ and, where present, -$L_A$-$W_B$, are other than —CH$_2$O(CH$_2$)$_2$N(Ph)CH$_2$CH$_3$.

More typically, -$L_A$-$W_A$ and, where present, -$L_A$-$W_B$, are other than each of the following moieties:

—CH$_2$OR$^{QQ}$ wherein R$^{QQ}$ is N-ethyl-N-phenyl-2-aminoethyl, 3,4-dimethoxyphenyl or 3-N,N-dimethylaminophenyl;

—NMe$_2$;

—N$^+$Me$_2$O$^-$;

—CH$_2$O(CH$_2$)$_2$N(H)C(O)N(H)Ph;

—CH$_2$O(CH$_2$)$_2$N(Ph)CH$_2$CH$_3$; and

—N=N—Ar$^P$, wherein Ar$^P$ is an unsubstituted or substituted phenyl group.

Typically, Ar$^P$ is:

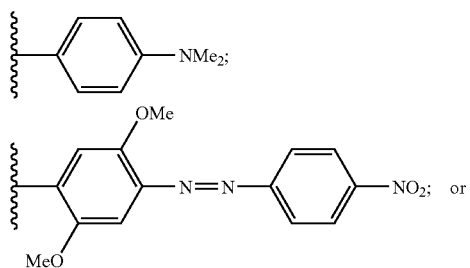

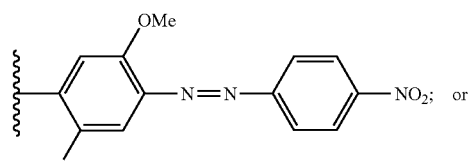

Typically, -$L_A$-$W_A$ and, where present, -$L_A$-$W_B$, are other than hydrogen.

Typically, -$L_A$-$W_A$ and, where present, -$L_A$-$W_B$, are other than hydrogen and other than $Q^P$, wherein:

$Q^P$ is selected from N($Z_1^P$)($Z_2^P$) and CH$_2$—$V^P$—($W^P$—$R^P$)$_a$;

$Z_1^P$ and $Z_2^P$ are independently selected from aryl which is unsubstituted or substituted, heteroaryl which is unsubstituted or substituted, $C_{1-10}$ alkoxy which is unsubstituted or substituted, $C_{1-10}$ alkylamino which is unsubstituted or substituted, di($C_{1-10}$)alkylamino which is unsubstituted or substituted, $C_{1-10}$ alkylthio which is unsubstituted or substituted, and $C_{1-10}$ alkyl which is unsubstituted or substituted and which is optionally interrupted by N($R^{2P}$), O or S wherein $R^{2P}$ is H or $C_{1-6}$ alkyl;

$V^P$ is $C_{1-10}$ alkylene, —O—$C_{1-10}$ alkylene-, —$C_{1-10}$ alkylene-O— or —O-$C_{1-10}$ alkylene-O—;

$W^P$ is a functional group of one of the following formulae (a) to (c):

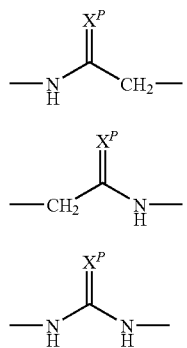

wherein $X^P$ is O, S or $NH_2^+$;

$R^P$ is selected from H, $C_{1-6}$ alkyl which is unsubstituted or substituted, aryl which is unsubstituted or substituted and heteroaryl which is unsubstituted or substituted; and a is 1, 2 or 3.

Typically, -$L_A$-$W_A$ and, where present, -$L_A$-$W_B$, are other than hydrogen and other than —$CH_2OR^Q$, wherein:

$R^Q$ is $Ar^{1Q}$ or $(CH_2)_b N(R^1 NR^{2Q})$;

$Ar^{1Q}$ is:

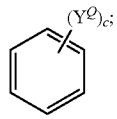

wherein $Y^Q$ is $C_{1-4}$ alkoxy or $N(R^{3Q})(R^{4Q})$;

$R^{3Q}$ and $R^{4Q}$, which may be the same or different, are $C_{1-4}$ alkyl;

c is 0 or an integer of 1 to 3;

$R^{1Q}$ is $C_{1-4}$ alkyl;

$R^{2Q}$ is phenyl; and b is an integer of 1 to 4.

More typically, -$L_A$-$W_A$ and, where present, -$L_A$-$W_B$, are other than hydrogen and other than $Q^P$ and other than —$CH_2OR^Q$, wherein $Q^P$ and $R^Q$ are as defined above.

Further typical features of the carbene precursor compounds of formula (I), the corresponding substrates of the invention, and the substrates of the invention which are functionalised with a group of formula (II), are set out as follows:

Typically, A is aryl. More typically, A is phenyl.

Typically, R is selected from unsubstituted or substituted aryl, unsubstituted or substituted heteroaryl, H, $CF_3$ and tert-butyl. More typically, R is selected from unsubstituted or substituted phenyl, H, $CF_3$ and tert-butyl. More typically, R is unsubstituted or substituted phenyl.

The reactivity of the diazo compound and its derived carbene can be modified by including electron releasing or electron withdrawing groups on the aromatic rings. In addition, the solubility of the diazo compound and its derived carbene can be modified by including groups of a given hydrophilicity or lipophilicity on the aromatic rings. Thus, suitable substituents for A or R (wherein R is substituted aryl, e.g. substituted phenyl, or substituted heteroaryl) include $C_{1-6}$ alkyl, aryl, cyano, amino, keto, $C_{1-10}$ alkylamino, di($C_{1-10}$)alkylamino, arylamino, diarylamino, arylalkylamino, amido, hydroxy, halo, carboxy, ester, $C_{1-6}$ alkoxy, aryloxy, haloalkyl, thiol, $C_{1-10}$ alkylthio, arylthio, sulfonic acid, and sulfonyl. More typically, substituents for A or R (wherein R is substituted aryl, e.g. substituted phenyl, or substituted heteroaryl) are selected from methyl, ethyl, propyl, butyl, —CN, —$NH_2$, keto, —C(=O)$NH_2$, —OH, halo, —COOH, —COOMe and —SH.

The or each group -$L_A$-$W_A$ and the or each group -$L_B$-$W_B$ may occupy any available position on the aryl or heteroaryl ring to which the group is bonded. Thus, when parameter "y" is 1, A is mono-substituted at any ring position by -$L_A$-$W_A$; for instance, when A is a phenyl group it may be substituted at any of positions 2, 3, 4, 5 and 6. When parameter "y" is 2, A is di-substituted at any two positions by -$L_A$-$W_A$; for instance, when A is a phenyl group it may be 2,3-2,4-, 2,5-, 2,6-, 3,4- or 3,5-disubstituted. When parameter "y" is 3, A is tri-substituted at any three positions by -$L_A$-$W_A$; for instance, when A is a phenyl group it may be 2,3,4-, 2,4,5- or 3,4,5-tri-substituted. Likewise, when R is aryl or heteroaryl, said aryl or heteroaryl may be mono-substituted at any ring position by -$L_B$-$W_B$. In that case, when R is a phenyl group it may be substituted at any of positions 2, 3, 4, 5 and 6. Alternatively, said aryl or heteroaryl R may be di-substituted at any ring position by -$L_B$-$W_B$. In that case, when R is a phenyl group, it may be 2,3-2,4-, 2,5-, 2,6-, 3,4- or 3,5-disubstituted. Alternatively, said aryl or heteroaryl R may be tri-substituted at any ring position by -$L_B$-$W_B$. In that case, when R is a phenyl group, it may be 2,3,4-, 2,4,5- or 3,4,5-tri-substituted.

Typically, y is 1.

Typically, when R is aryl or heteroaryl, said aryl or heteroaryl is not substituted by -$L_B$-$W_B$. However, when said aryl or heteroaryl is substituted by -$L_B$-$W_B$, said aryl or heteroaryl R is typically mono-substituted by -$L_B$-$W_B$.

Typically, $L_A$ is a single bond or $C_{1-20}$ alkylene which is substituted or unsubstituted and optionally interrupted by N(R''), O, S or arylene, wherein R'' is H, $C_{1-6}$ alkyl or aryl. More typically, $L_A$ is a single bond or $C_{1-6}$ alkylene which is optionally interrupted by O. For example, $L_A$ may be a single bond, methylene, ethylene, propylene, butylene, pentylene or hexylene, wherein said ethylene, propylene, butylene, pentylene or hexylene, are either uninterrupted or interrupted by a single oxygen atom. $L_A$ may be methylene or —$CH_2$—O—$CH_2$—.

Typically, $L_2$, as used herein, is a single bond or a $C_{1-6}$ alkylene which is substituted or unsubstituted and optionally interrupted by N(R''), O, S or arylene, wherein R'' is H, $C_{1-6}$ alkyl or aryl. More typically, $L_2$ is a single bond or unsubstituted $C_{1-6}$ alkylene which is uninterrupted or interrupted by a single oxygen atom. Even more typically, $L_2$ is a single bond, methylene, ethylene, propylene, butylene, pentylene or hexylene.

Typically R'', as used herein, is H, methyl, ethyl or phenyl. More typically, R'' is H.

Typically R''', as used herein, is H, methyl, ethyl or phenyl. More typically, R''' is H.

Typically, the carbene precursor compound of formula (I) is selected from:

[4-(Diazo(phenyl)methyl)phenyl]methanol;

7-Oxa-bicyclo[2.2.1]hept-5-ene-2-carboxylic acid-4-(diazophenylmethyl)-benzyl ester;

1-(allyloxymethyl)-4-(diazo(phenyl)methyl)benzene; and

[4-(Diazo-phenyl-methyl)-benzyl]phosphonic acid diethyl ester.

Thus, typically, the process of the invention for producing a substrate having a functionalised surface comprises:

(a) contacting the substrate with a carbene precursor, which carbene precursor is selected from:
[4-(Diazo(phenyl)methyl)phenyl]methanol;
7-Oxa-bicyclo[2.2.1]hept-5-ene-2-carboxylic acid-4-(diazophenylmethyl)-benzyl ester;
1-(allyloxymethyl)-4-(diazo(phenyl)methyl)benzene; and
[4-(Diazo-phenyl-methyl)-benzyl]phosphonic acid diethyl ester; and (b) generating a carbene reactive intermediate from the carbene precursor so that it reacts with the substrate to functionalise the surface, thereby yielding said substrate having a functionalised surface.

The process of the invention for producing a substrate having an adhesive surface may comprise reacting the substrate with a plurality of different carbene precursors, typically simultaneously. Simultaneous reaction with two or more different carbene precursors typically results in the production of a substrate whose surface is functionalised with a random mixture of the different carbene functionalities.

Accordingly, in one embodiment, the process of the invention for producing a substrate having an adhesive surface further comprises:

(a') contacting the substrate with a further carbene precursor, which further carbene precursor is a compound of formula (I) as defined herein, which compound is different from the carbene precursor used in step (a); and (b') generating a carbene reactive intermediate from the further carbene precursor so that it reacts with the substrate to functionalise the surface.

Typically, step (b') comprises either:

(i') when $W_A$ or $W_B$ of said further carbene precursor comprises an adhesive functional group, generating a carbene reactive intermediate from the further carbene precursor so that it reacts with the substrate to functionalise the surface; or (ii') when $W_A$ or $W_B$ in said further carbene precursor comprises a precursor of a adhesive functional group, generating a carbene reactive intermediate from the further carbene precursor so that it reacts with the substrate to functionalise the surface, and (c') converting said group which is a precursor into an adhesive functional group.

Typically, steps (a) and (a') occur simultaneously. Typically, the generations of the carbene reactive intermediates in steps (b) and (b') occur simultaneously.

The substrate treated in accordance with the present invention may be any natural or synthetic substrate which is capable of reaction with a carbene reactive intermediate generated from a diarylcarbene precursor of formula (I) as defined above.

Typically the substrate is, or comprises, a natural or synthetic polymer including but not limited to cellulose, polyglycoside, polypeptides, polyacrylates, polyacrylics, polyamides, polyimides, polycarbonates, polyesters, epoxy resins, polyethers, polyketones, polyolefins, rubbers, polystyrenics, polysulfones, polyurethanes, polyvinyls and their co-polymers.

Where the substrate comprises a polymer, the molecular weight of the polymeric substrate may be selected according to the particular utility of the end product.

In one embodiment, the substrate is selected from polyesters, polyacrylates, polyolefins, polyamides, polyimides, polysulfones and epoxy resins. Typically the polyolefin is a homopolymer or copolymer of ethylene, propylene, styrene, PET (polyethylene terephthalate) or EPDM (ethylene propylene diene monomer).

The polymer may be a homopolymer or a copolymer, for instance a block copolymer. It may thus be derived from monomeric units which are the same or different.

The polymer may be modified, for instance by admixture with another organic or inorganic material. The substrate may thus comprise both a polymer and an inorganic material, for instance a mixture of a polymer and an inorganic material such as an inorganic filler. The substrate may, for example, comprise a mixture of one or more of the polymers referred to above and one or more of the inorganic materials referred to herein. Modified polymers of this type are suitable for use in, for instance, semiconductor applications. Technical problems can arise when polymers are used as coating or bonding agents with semiconductors, for example owing to their different behaviour on heating. The inclusion of an inorganic filler with a polymer serves to modify the thermal properties of the polymer and make it better suited for use together with a semiconductor.

In one embodiment, the substrate is, or comprises, a thermoplastic resin or a thermosetting resin.

The substrate may be, or comprise, an inorganic material including but not limited to a metal, a metal alloy, or a metal salt, silica, glasses, alumina, titania, and allotropes of carbon such as diamond, diamond-like carbon, graphite, fullerenes and nanotubes.

In one embodiment the substrate is a metal or an alloy of a metal, which metal is any metal other than an alkali metal or an alkaline earth metal. Typically, the metal other than an alkali metal or an alkaline earth metal or alloy is selected from: Al, Cu, Pb, Au, Ag, Pt, Pd and Sn. The metal may also include group IV (group 14) elements, for example Ge and Si. The metallisation of polymer surfaces is of relevance in printed circuit board and electronic technology. Thus, adhesion of such metals or alloys to other materials may be of use in the electronics industry, for example in the manufacture of printed circuit boards. Alternatively, the substrate is a salt of a metal. Typically, the metal salt is a calcium salt.

Typically, the substrate is, or comprises, a nanoparticle or a microparticle. More typically, the substrate is, or comprises, a high molecular weight material which is a nanoparticle or a microparticle.

As used herein, the term "microparticle" means a microscopic particle whose size is measured in micrometres (µm). Typically, the microparticle has an average diameter of from 1 µm to 1000 µm. More typically, the microparticle has an average diameter of from 1 µm to 500 µm, for instance from 1 µm to 250 µm. Most typically, the microparticle has an average diameter of from 1 µm to 100 µm.

As used herein, the term "nanoparticle" means a microscopic particle whose size is measured in nanometres (nm). Typically, the nanoparticle has an average diameter of from 1 nm to 1000 nm. More typically, the nanoparticle has an average diameter of from 5 nm to 500 µm, for instance from 5 µm to 250 µm. Most typically, the nanoparticle has an average diameter of from 5 µm to 100 µm. Thus, in one embodiment the substrate is, or comprises, $C_{60}$. In another embodiment the substrate is, or comprises, a nanotube. Typically, the nanotube is a carbon nanotube. The nanotube may however comprise atoms other than carbon.

In one embodiment the substrate is, or comprises, a pigment. The pigment may be any colouring agent made from a natural or synthetic substance.

Typically, the substrate is, or comprises, a nanoparticle or a microparticle, which nanoparticle or microparticle is, or comprises, a pigment.

In one embodiment, the substrate is, or comprises, textile.
In another embodiment, the substrate is, or comprises, paper.

The substrate may comprise any two or more of the above-listed materials.

The substrate treated in accordance with the present invention may be in any suitable physical form. Thus, the substrate may be in the form of a film, a layer, a sheet or a board. Alternatively, the substrate may be in powder form, or in the form of pellets, beads, particles, nanoparticles or microparticles. The pellets, beads or particles may be macroscopic particles, i.e. visible to the naked eye, or microscopic particles. Thus, the particles could be microparticles or nanoparticles.

In step (a) of the process of the invention for producing a substrate having an adhesive surface, the substrate is contacted with the carbene precursor, which is a compound of formula (I). Typically, the substrate is contacted with the carbene precursor by dip coating, spray coating, rolling, printing or co-extrusion. The dip coating, spray coating, rolling, printing or co-extrusion may be performed in solution or otherwise. Thus, the dip coating, spray coating, rolling, printing or co-extrusion may be performed using a solution of the carbene precursor or using the neat carbene precursor. Similarly, the dip coating, spray coating, rolling, printing or co-extrusion may be carried out using the neat substrate or using a suitable solution of the substrate.

Typically, the neat substrate is dipped in or sprayed with the neat carbene precursor or a solution of the carbene precursor, in order to form a coating on a surface of the substrate, which coating comprises the carbene precursor. Alternatively, the neat carbene precursor or a solution thereof may be applied to the substrate by printing it, or by rolling it, onto the surface of the substrate. In another embodiment, the substrate and carbene precursor are contacted by co-extruding the substrate and carbene precursor.

In step (b) of the process of the present invention for producing a substrate having an adhesive surface, the generated carbene intermediate reacts with the substrate to functionalise the surface. In this context, the term "surface" means either the whole of the surface of the substrate or only a portion of the surface of the substrate.

The carbene reactive intermediate is typically generated by a thermal process and/or by an irradiation process. Typically, the carbene reactive intermediate is generated by thermal irradiation, for instance by heating. This heat might be applied externally, but may also be as a result of another process, for example, extrusion. Alternatively, the carbene reactive intermediate may be generated by electromagnetic radiation, for instance by UV, microwave or laser irradiation, or by ultrasonic irradiation. Some of these techniques, including laser and UV irradiation, are suitable for generation of the carbene reactive intermediate selectively, i.e. on only a portion of the surface of the substrate.

Typically, only a portion of the surface of the substrate is functionalised. For example, the surface may be modified in certain areas only, to form specific a "pattern" of surface functionalisation. In this way, the two-dimensional-shape-of-the-resulting adhesive surface may be controlled. This may be useful in the design of printed circuit boards, for example, where the adhesion of metal to substrate is only desired in certain specific places.

In one embodiment, the carbene reactive intermediate is generated selectively, i.e. only on certain portions of the surface of the substrate. In this way, only the particular regions of the surface on which the carbene reactive intermediate has been generated become functionalised. This is known as "selective activation", and can be used to form specific a "pattern" of surface functionalisation.

Accordingly, in one embodiment of the process of the invention for producing a substrate having an adhesive surface, the generation of said carbene reactive intermediate in step (b) is performed on only a portion of the surface of the substrate.

Such selective activation can be achieved using "directed activation", which may involve irradiation of certain portions of the surface only. Such directed activation can be achieved, for instance, by laser writing or by UV writing.

Alternatively, such selective activation can be achieved by masking a portion of the surface of the substrate, followed by activation (i.e. generation of the carbene reactive intermediate) on only the unmasked parts of the surface. Usually, this is followed by removal of the mask and washing of the surface to remove unreacted material.

The selective activation process may be repeated any number of times, leading to the build-up of a complex pattern of surface functionalisation in a controlled way.

Alternatively, in order that only a portion of the surface of a substrate is functionalised, the surface may be masked before contacting the substrate with the carbene precursor in step (a). Again, in this way the carbene reactive intermediate only contacts, and subsequently only reacts with, the unmasked areas of the substrate, and does not react with the masked areas.

Additionally or alternatively, chemical patterning techniques, such as selective irradiation, ink jet printing or screen printing (where the carbene precursor compound is used as the printing medium) can be used to control exactly which parts of the surface of the substrate are exposed to the carbene precursor compound (and consequently the carbene reactive intermediate), and consequently, which parts of the surface are functionalised.

For example, by ink jet printing a solution of the carbene precursor compound onto the surface of the substrate in certain places only, the surface may be functionalised with the carbene reactive intermediate in certain places only. The resulting adhesive surface will then have a specific two-dimensional pattern, such that an adherend adheres onto that pattern only.

Such chemical patterning techniques and selective activation techniques can be performed more than once and/or in combination with one another, leading to the build-up of a complex pattern of surface modification.

In one embodiment of the process of the invention for producing a substrate having an adhesive surface, step (a) comprises contacting the substrate with said carbene precursor using chemical patterning. Additionally or alternatively, the process of the invention for producing a substrate having an adhesive surface further comprises masking the substrate prior to contacting said substrate with said carbene precursor.

In one embodiment of the process of the invention for producing a substrate having an adhesive surface, the process further comprises the step of contacting the adhesive surface of said substrate, or a part thereof, with an adherend, under conditions which cause adhesion of said substrate to said adherend.

Typically, the adherend comprises a polymer, an inorganic material, a biological cell or biological tissue.

When the adherend comprises a polymer, the polymer is typically a natural or synthetic polymer including but not limited to cellulose, polyglycoside, polypeptides, polyacrylates, polyacrylics, polyamides, polyimides, polycarbonates, polyesters, epoxy resins, polyethers, polyketones, polyolefins, rubbers, polystyrenics, polysulfones, polyurethanes, polyvinyls and their co-polymers. In one embodiment, the adherend is selected from polyesters, polyacrylates, polyolefins, polyamides, polysulfones and epoxy resins. Typically the adherend is a homopolymer or copolymer of ethylene, propylene, styrene, PET (polyethylene terephthalate) or EPDM (ethylene propylene diene monomer). The polymer may be a homopolymer or a copolymer, for instance a block copolymer. It may thus be derived from monomeric units which are the same or different. The polymer may be modified, for instance by admixture with another organic or inorganic material. The adherend may thus comprise both a polymer and an inorganic material, for instance a mixture of a polymer and an inorganic material such as an inorganic filler. The adherend may, for example, comprise a mixture of one or more of the polymers referred to above and one or more of the inorganic materials referred to above.

In one embodiment, the adherend is, or comprises, a thermoplastic resin or a thermosetting resin.

The adherend may be, or comprise, an inorganic material including but not limited to a metal, a metal alloy, or a metal salt, silica, glasses, alumina, titania, and allotropes of carbon such as diamond, diamond-like carbon, graphite, fullerenes and nanotubes.

In one embodiment the adherend is a metal or an alloy of a metal, which metal is any metal other than an alkali metal or an alkaline earth metal. Typically, the metal other than an alkali metal or an alkaline earth metal or alloy is selected from: Al, Cu, Pb, Au, Ag, Pt, Pd and Sn. The metal may also include group IV (group 14) elements, for example Ge and Si. The metallisation of polymer surfaces is of relevance in printed circuit board and electronic technology. Thus, adhesion of such metals or alloys to substrate materials may be of use in the electronics industry, for example in the manufacture of printed circuit boards.

Typically, the adherend is, or comprises, a nanoparticle or a microparticle. More typically, the adherend is, or comprises, a high molecular weight material which is a nanoparticle or a microparticle.

Thus, in one embodiment the adherend is, or comprises, $C_{60}$. In another embodiment the adherend is, or comprises, a nanotube. Typically, the nanotube is a carbon nanotube. The nanotube may, however, comprise atoms other than carbon.

In one embodiment the adherend is, or comprises, a pigment. The pigment may be any colouring agent made from a natural or synthetic substance.

Typically, the adherend is, or comprises, a nanoparticle or a microparticle, which nanoparticle or microparticle is, or comprises, a pigment.

In one embodiment, the adherend is, or comprises, textile.

In another embodiment, the adherend is, or comprises, paper.

The adherend may comprise any two or more of the above-listed materials.

The adherend may be present in any suitable physical form. Thus, the adherend may be in the form of a film, a layer, a sheet or a board. Alternatively, the adherend may be in powder form, or in the form of pellets, beads, particles, nanoparticles or microparticles. The pellets, beads or particles may be macroscopic particles, i.e. visible to the naked eye, or microscopic particles. Thus, the particles could be microparticles or nanoparticles.

As mentioned above, certain types of adhesive functional groups are capable of interaction with certain types of adherends. Thus, by selecting a suitable adhesive functional group, the substrate can be adhered to a particular adherend as desired (for example to any of the adherends referred to above). Generally, a suitable adhesive functional group is one which is capable of physical interaction with the adherend (e.g. due to an electrostatic attraction between adhesive functional group and adherend) or capable of forming a chemical bond with the adherend (e.g. a covalent bond, ionic bond, hydrogen bond or other non-covalent bond). Typically, a suitable adhesive functional group is structurally similar to one or more of the chemical moieties present in the adherend itself. For example, epoxy or alcohol functional groups would be suitable for adhering a substrate to an epoxy resin adherend, and acrylate or other $\alpha,\beta$-unsaturated ketone groups, or amine functional groups would be suitable for adhering a substrate to a polyacrylate adherend.

Table 1 below lists various adherends, and, for each adherend, some examples of suitable adhesive functional groups that would be expected to aid adhesion to the adherend.

TABLE 1

| Adherend | Examples of suitable adhesive functional groups |
|---|---|
| Epoxy Resin | (epoxide structure with R) <br> R—NH$_2$ <br> R—OH  R—SH |
| Polyacrylate | (acrylate ester and vinyl ketone structures with R) <br> R—NH$_2$  R—SH |
| Polystyryl | (acrylate ester and vinyl ketone structures with R) |
| Polyolefin | R—OH  R—NH$_2$  R—SH <br> (acrylate ester, vinyl, and phosphonic acid structures with R) |

TABLE 1-continued

| Adherend | Examples of suitable adhesive functional groups |
| --- | --- |
| Polyurethane | R—OH  R—NH₂  R—SH |
| Metal, Metal salt, Biological cell, Biological tissue |  and salts thereof, for example calcium salts R—OH  R—NH₂  R—SH |
| Polyester | R—OH  R—NH₂  R—SH |
| Polyamide | R—OH  R—NH₂  R—SH |
| Polycarbonate | R—OH  R—NH₂  R—SH |
| Polyimide | R—OH  R—NH₂  R—SH |

By selecting a suitable adhesive functional group, the substrate can be adhered to a particular adherend as desired. Thus, the process of the invention for producing a substrate having an adhesive surface may be used to achieve improved adhesion in polymer, paper, textile and other material composites, hybrids and laminates.

The process may also be used for the modification of thermoplastic and thermosetting resins.

The invention further provides a carbene precursor compound of the following formula (I):

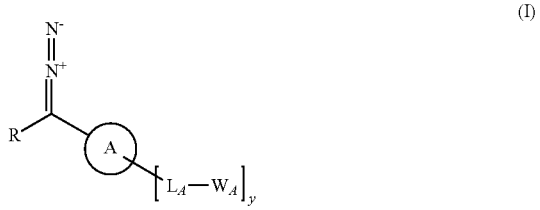

wherein:
A is an aryl or heteroaryl ring;
y is 1, 2, 3, 4 or 5;
$L_A$ is a single bond, -alk-, -arylene-, -alk-arylene-, -X-alk-, -X-alk-X-, -X-arylene-, X-arylene-X-, -X-alk-arylene-, -alk-X-arylene-, -alk-arylene-X, -X-alk-X-arylene-, -alk-X-arylene-X- or -X-alk-X-arylene-X-, wherein X is N(R"), O, or S and wherein alk is $C_{1-20}$ alkylene which is optionally interrupted by N(R"), O, S or arylene, wherein R" is H, $C_{1-6}$ alkyl or aryl;
$W_A$ is a group comprising an adhesive functional group or a group which is a precursor of an adhesive functional group;
R is selected from hydrogen, aryl, heteroaryl, $C_{1-10}$ alkoxy, aryloxy, di($C_{1-10}$)alkylamino, alkylarylamino, diarylamino, $C_{1-10}$ alkylthio, arylthio and $CR'_3$, wherein each R' is independently selected from a halogen atom, aryl, heteroaryl, $C_{3-7}$ cycloalkyl, $C_{5-7}$ heterocyclyl and $C_{1-6}$ alkyl, which $C_{1-6}$ alkyl is optionally interrupted by N(R"), O, S or arylene wherein R" is as defined above;
provided that when R is aryl or heteroaryl, said aryl or heteroaryl may be unsubstituted or substituted by one, two, three, four or five groups, which groups are independently selected from $C_{1-6}$ alkyl, aryl, cyano, amino, keto, $C_{1-10}$ alkylamino, di($C_{1-10}$)alkylamino, arylamino, diarylamino, arylalkylamino, amido, hydroxy, halo, carboxy, ester, $C_{1-6}$ alkoxy, aryloxy, haloalkyl, thiol, $C_{1-10}$ alkylthio, arylthio, sulfonic acid, sulfonyl and -$L_B$-$W_B$, wherein $L_B$ is as defined above for $L_A$ and is the same as or different from $L_A$, and $W_B$ is as defined above for $W_A$ and is the same as or different from $W_A$,
provided that the compound is not: 4,4'-bis(N-acetyl-2-aminoethyl)diphenyldiazomethane, 1-{2-[4-(diazo-phenyl-methyl)-benzyloxy]-ethyl}-3-phenyl urea, 4-([N-ethyl-N-phenyl-2-aminoethyl]oxymethyl)phenyl phenyl diazomethane, bis-4,4'-N,N-dimethylamino diphenyldiazomethane, 4-([3,4-dimethoxyphenyl]oxymethyl)phenyl phenyl diazomethane, 4-([3-N,N-diethylaminophenyl]oxymethyl)phenyl phenyl diazomethane or 4-([N-ethyl-N-phenyl-2-aminoethyl]oxymethyl)phenyl phenyl diazomethane.

Typically, R is selected from aryl, heteroaryl, $C_{1-10}$ alkoxy, aryloxy, di($C_{1-10}$)alkylamino, alkylarylamino, diarylamino, $C_{1-10}$ alkylthio, arylthio and $CR'_3$, wherein each R' is independently selected from a halogen atom, aryl, heteroaryl, $C_{3-7}$ cycloalkyl, $C_{5-7}$ heterocyclyl and $C_{1-6}$ alkyl, which $C_{1-6}$ alkyl is optionally interrupted by N(R"), O, S or arylene wherein R" is as defined above, provided that R is not $CF_3$.

Typically, the compound of formula (I) is not 4,4'-bis(N-acetyl-2-aminoethyl)diphenyldiazomethane, 1-{2-[4-(diazo-phenyl-methyl)-benzyloxy]-ethyl}-3-phenyl urea, 4-([N-ethyl-N-phenyl-2-aminoethyl]oxymethyl)phenyl phenyl diazomethane, bis-4,4'-N,N-dimethylamino diphenyldiazomethane, 4-([3,4-dimethoxyphenyl]oxymethyl)phenyl phenyl diazomethane, 4-([3-N,N-diethylaminophenyl]oxymethyl)phenyl phenyl diazomethane or bis-4,4'-tert-butyl ester diphenyldiazomethane.

The diazo carbene precursor compounds of formula (I) may be prepared by oxidising the corresponding hydrazone compound. Accordingly, the present invention provides a process for producing a carbene precursor compound of formula (I):

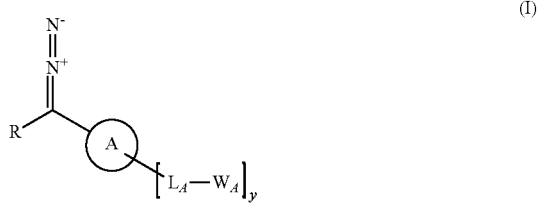

wherein
A is an aryl or heteroaryl ring;
y is 1, 2, 3, 4 or 5;
$L_A$ is a single bond, -alk-, -arylene-, -alk-arylene-, -X-alk-, -X-alk-X-, -X-arylene-, X-arylene-X-, -X-alk-arylene-, -alk- X-arylene-, -alk-arylene-X, -X-alk-X-arylene-, -alk-X-arylene-X- or -X-alk-X-arylene-X-, wherein X is N(R"), O, or S and wherein alk is $C_{1-70}$ alkylene which is optionally interrupted by N(R"), O, S or arylene, wherein R" is H, $C_{1-6}$ alkyl or aryl;

$W_A$ is a group comprising an adhesive functional group or a group which is a precursor of an adhesive functional group;

R is selected from hydrogen, aryl, heteroaryl, $C_{1-10}$ alkoxy, aryloxy, di($C_{1-10}$)alkylamino, alkylarylamino, diarylamino, $C_{1-10}$ alkylthio, arylthio and $CR'_3$, wherein each R' is independently selected from a halogen atom, aryl, heteroaryl, $C_{3-7}$ cycloalkyl, $C_{5-7}$ heterocyclyl and $C_{1-6}$ alkyl, which $C_{1-6}$ alkyl is optionally interrupted by N(R"), O, S or arylene wherein R" is as defined above;

provided that when R is aryl or heteroaryl, said aryl or heteroaryl may be unsubstituted or substituted by one, two, three, four or five groups, which groups are independently selected from $C_{1-6}$ alkyl, aryl, cyano, amino, keto, $C_{1-10}$ alkylamino, di($C_{1-10}$)alkylamino, arylamino, diarylamino, arylalkylamino, amido, hydroxy, halo, carboxy, ester, $C_{1-6}$ alkoxy, aryloxy, haloalkyl, thiol, $C_{1-10}$ alkylthio, arylthio, sulfonic acid, sulfonyl and -$L_B$-$W_B$, wherein $L_B$ is as defined above for $L_A$ and is the same as or different from $L_A$, and $W_B$ is as defined above for $W_A$ and is the same as or different from $W_A$;

provided that the compound is not: 4,4'-bis(N-acetyl-2-aminoethyl)diphenyldiazomethane, 1-{2-[4-(diazo-phenyl-methyl)-benzyloxy]-ethyl}-3-phenyl urea, 4-([N-ethyl-N-phenyl-2-aminoethyl]oxymethyl)phenyl phenyl diazomethane, bis-4,4'-N,N-dimethylamino diphenyldiazomethane, 4-([3,4-dimethoxyphenyl]oxymethyl)phenyl phenyl diazomethane or 4-([3-N,N-diethylaminophenyl]oxymethyl)phenyl phenyl diazomethane, which process comprises oxidising a compound of the following formula (III):

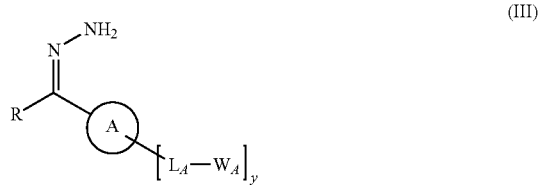

(III)

wherein:

A is an aryl or heteroaryl ring;

y is 1, 2, 3, 4 or 5;

$L_A$ is a single bond, -alk-, -arylene-, -alk-arylene-, -X-alk-, -X-alk-X-, -X-arylene-, X-arylene-X-, -X-alk-arylene-, -alk-X-arylene-, -alk-arylene-X, -X-alk-X-arylene-, -alk-X-arylene-X- or -X-alk-X-arylene-X-, wherein X is N(R"), O, or S and wherein alk is $C_{1-20}$ alkylene which is optionally interrupted by N(R"), O, S or arylene, wherein R" is H, $C_{1-6}$ alkyl or aryl;

$W_A$ is a group comprising an adhesive functional group or a group which is a precursor of an adhesive functional group;

R is selected from hydrogen, aryl, heteroaryl, $C_{1-10}$ alkoxy, aryloxy, di($C_{1-10}$)alkylamino, alkylarylamino, diarylamino, $C_{1-10}$ alkylthio, arylthio and $CR'_3$, wherein each R' is independently selected from a halogen atom, aryl, heteroaryl, $C_{3-7}$ cycloalkyl, $C_{5-7}$ heterocyclyl and $C_{1-6}$ alkyl, which $C_{1-6}$ alkyl is optionally interrupted by N(R"), O, S or arylene wherein R" is as defined above;

provided that when R is aryl or heteroaryl, said aryl or heteroaryl may be unsubstituted or substituted by one, two, three, four or five groups, which groups are independently selected from $C_{1-6}$ alkyl, aryl, cyano, amino, keto, $C_{1-10}$ alkylamino, di($C_{1-10}$)alkylamino, arylamino, diarylamino, arylalkylamino, amido, hydroxy, halo, carboxy, ester, $C_{1-6}$ alkoxy, aryloxy, haloalkyl, thiol, $C_{1-10}$ alkylthio, arylthio, sulfonic acid, sulfonyl and -$L_B$-$W_B$, wherein $L_B$ is as defined above for $L_A$ and is the same as or different from $L_A$, and $W_B$ is as defined above for $W_A$ and is the same as or different from $W_A$; and provided that the compound is not:

4,4'-bis(N-acetyl-2-aminoethyl)benzophenone hydrazone, 1-{2-[4-(hydrazono-phenyl-methyl)-benzyloxy]-ethyl}-3-phenyl urea, 4,4-bis-N,N-dimethylamino benzophenone hydrazone, 4-([3,4-dimethoxyphenyl] oxymethyl)benzophenone hydrazone, 4-([3-N,N-diethylaminophenyl]oxymethyl)benzophenone hydrazone or 4-([N-ethyl-N-phenyl-2-aminoethyl]oxymethyl)benzophenone hydrazone;

to produce a carbene precursor compound of formula (I).

Any suitable oxidant may be used. Suitable oxidants include metal oxides, such as mercuric oxide, nickel peroxide, or hydrogen peroxide or chlorine (bleach). Typically, the oxidant is mercuric oxide. More typically, this oxidation is conducted in the presence of a base, for instance a metal hydroxide and sodium sulphate. The metal hydroxide is typically an alkali metal hydroxide, for instance potassium hydroxide. A saturated solution of the metal hydroxide is generally used. The solvent used for the metal hydroxide is suitably a polar protic solvent such as an alcohol, for instance ethanol. The solvent used for the solution of the compound of formula (III) is suitably a polar aprotic solvent, for instance tetrahydrofuran (THF) or an ether.

Typically, R is selected from aryl, heteroaryl, $C_{1-10}$ alkoxy, aryloxy, di($C_{1-10}$)alkylamino, alkylarylamino, diarylamino, $C_{1-10}$ alkylthio, arylthio and $CR'_3$, wherein each R' is independently selected from a halogen atom, aryl, heteroaryl, $C_{3-7}$ cycloalkyl, $C_{5-7}$ heterocyclyl and $C_{1-6}$ alkyl, which $C_{1-6}$ alkyl is optionally interrupted by N(R"), O, S or arylene wherein R" is as defined above, provided that R is not $CF_3$.

Typically, the compound of formula (I) is not 4,4'-bis(N-acetyl-2-aminoethyl)diphenyldiazomethane, 1-{2-[4-(diazo-phenyl-methyl)-benzyloxy]-ethyl}-3-phenyl urea, 4-([N-ethyl-N-phenyl-2-aminoethyl]oxymethyl)phenyl phenyl diazomethane, bis-4,4'-N,N-dimethylamino diphenyldiazomethane, 4-([3,4-dimethoxyphenyl]oxymethyl)phenyl phenyl diazomethane, 4-([3-N,N-diethylaminophenyl]oxymethyl)phenyl phenyl diazomethane or bis-4,4'-tert-butyl ester diphenyldiazomethane.

Thus, typically, the compound of formula (III) is not 4,4'-bis(N-acetyl-2-aminoethyl)benzophenone hydrazone, 1-{2-[4-(hydrazono-phenyl-methyl)-benzyloxy]-ethyl}-3-phenyl urea, 4,4-bis-N,N-dimethylamino benzophenone hydrazone, 4-([3,4-dimethoxyphenyl]oxymethyl)benzophenone hydrazone, 4-([3-N,N-diethylaminophenyl]oxymethyl)benzophenone hydrazone, 4-([N-ethyl-N-phenyl-2-aminoethyl]oxymethyl)benzophenone hydrazone or 4,4'-bis-tert-butyl ester benzophenone hydrazone.

A compound of formula (I) in which $W_A$ or $W_B$ contains a group selected from —OH and —NH(R") can be further derivatised in order to produce a compound of formula (I) in which $W_A$ or $W_B$ comprises the following group:

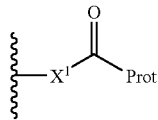

in which Prot is a protecting group which is a precursor to a —CH=CH$_2$ group; and $X^1$ is N(R") or O, wherein R" is selected from H, $C_{1-6}$ alkyl and aryl.

Accordingly, in one embodiment of the process of the present invention for producing a carbene precursor compound of formula (I):

either $W_A$ or $W_B$ comprises a group selected from —OH and —NH(R"), wherein R" is selected from H, $C_{1-6}$ alkyl and aryl, and the process further comprises reacting said —OH or —NH(R") with Hal-C(O)-Prot, wherein Hal is a suitable leaving group and Prot is a protecting group which is a precursor to a —CH=CH$_2$ group, to produce a carbene precursor compound of formula (I) in which either $W_A$ or $W_B$ comprises a functional group having the following structure:

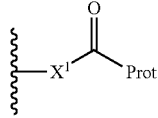

wherein $X^1$ is N(R") or O, wherein R" and Prot are as defined above. Typically, Hal is a halo group, for instance Cl, Br or I. Alternatively, Hal may be any other suitable leaving group which, for reacting said —OH or —NH(R") with Hal-C(O)-Prot, is functionally equivalent to a halo group such as Cl, Br or I. When $X^1$ is O, a suitable leaving group includes any leaving group which gives an active ester.

Typically, the reaction is carried out in the presence of a base. Typically, the base is a Lewis base, for example an alkyl amine such as triethylamine. The reaction is typically carried out at a temperature below room temperature, for example at about 0° C. The solvent used for the reaction is typically an aprotic solvent, such as a hydrocarbon. Typically, toluene is used as the solvent.

The hydrazone compounds of formula (III) may be prepared by treating the corresponding ketone compound with hydrazine in the presence of heat and a solvent. Accordingly, the present invention provides a process for producing a compound of formula (III):

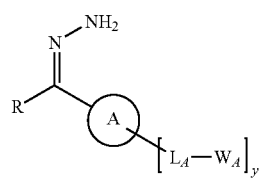

(III)

wherein:
A is an aryl or heteroaryl ring;
y is 1, 2, 3, 4 or 5;

$L_A$ is a single bond, -alk-, -arylene-, -alk-arylene-, -X-alk-, -X-alk-X-, -X-arylene-, X-arylene-X-, -X-alk-arylene-, -alk-X-arylene-, -alk-arylene-X, -X-alk-X-arylene-, -alk-X-arylene-X- or -X-alk-X-arylene-X-, wherein X is N(R"), O, or S and wherein alk is $C_{1-20}$ alkylene which is optionally interrupted by N(R"), O, S or arylene, wherein R" is H, $C_1$ alkyl or aryl;

$W_A$ is a group comprising an adhesive functional group or a group which is a precursor of an adhesive functional group;

R is selected from hydrogen, aryl, heteroaryl, $C_{1-10}$ alkoxy, aryloxy, di($C_{1-10}$)alkylamino, alkylarylamino, diarylamino, $C_{1-10}$ alkylthio, arylthio and CR'$_3$, wherein each R' is independently selected from a halogen atom, aryl, heteroaryl, $C_{3-7}$ cycloalkyl, $C_{5-7}$ heterocyclyl and $C_{1-6}$ alkyl, which $C_{1-6}$ alkyl is optionally interrupted by N(R"), O, S or arylene wherein R" is as defined above;

provided that when R is aryl or heteroaryl, said aryl or heteroaryl may be unsubstituted or substituted by one, two, three, four or five groups, which groups are independently selected from $C_{1-6}$ alkyl, aryl, cyano, amino, keto, $C_{1-10}$ alkylamino, di($C_{1-10}$)alkylamino, arylamino, diarylamino, arylalkylamino, amido, hydroxy, halo, carboxy, ester, $C_{1-6}$ alkoxy, aryloxy, haloalkyl, thiol, arylthio, sulfonic acid, sulfonyl and -$L_B$-$W_B$, wherein $L_B$ is as defined above for $L_A$ and is the same as or different from $L_A$, and $W_B$ is as defined above for $W_A$ and is the same as or different from $W_A$; and provided that the compound is not:
4,4'-bis(N-acetyl-2-aminoethyl)benzophenone hydrazone, 1-{2-[4-(hydrazono-phenyl-methyl)-benzyloxy]-ethyl}-3-phenyl urea, 4,4-bis-N,N-dimethylamino benzophenone hydrazone, 4-([3,4-dimethoxyphenyl]oxymethyl)benzophenone hydrazone, 4-([3-N,N-diethylaminophenyl]oxymethyl)benzophenone hydrazone or 4-([N-ethyl-N-phenyl-2-aminoethyl]oxymethyl)benzophenone hydrazone;

the process comprising treating a compound of formula (IV) with hydrazine in the presence of heat:

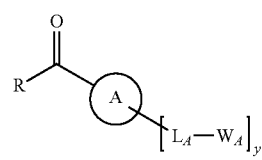

(IV)

wherein R, A, $L_A$, $W_A$, and y are as defined above.

Typically, hydrazine is used in the form of hydrazine hydrate. Typically, the compound of formula (IV) is treated with hydrazine in the presence of heat and a solvent. Any suitable solvent may be employed, for instance a polar protic solvent such as an alcohol. Typically, the solvent is methanol or ethanol. The reaction is carried out with heating, typically at the reflux temperature of the solvent used. For example, when the solvent is ethanol the reaction is suitably carried out at a temperature of 78° C. or higher, e.g. at a temperature of 80° C.

Typically, R is selected from aryl, heteroaryl, $C_{1-10}$ alkoxy, aryloxy, di($C_{1-10}$)alkylamino, alkylarylamino, diarylamino, $C_{1-10}$ alkylthio, arylthio and CR'$_3$, wherein each R' is independently selected from a halogen atom, aryl, heteroaryl, $C_{3-7}$ $C_{5-7}$ heterocyclyl and $C_{1-6}$ alkyl, which $C_{1-6}$ alkyl is optionally interrupted by N(R"), O, S or arylene wherein R" is as defined above, provided that R is not CF$_3$.

Typically, the compound of formula (III) is not 4,4'-bis(N-acetyl-2-aminoethyl)benzophenone hydrazone, 1-{2-[4-(hydrazono-phenyl-methyl)-benzyloxy]-ethyl}-3-phenyl urea, 4,4-bis-N,N-dimethylamino benzophenone hydrazone, 4-([3,4-dimethoxyphenyl]oxymethyl)benzophenone hydrazone, 4-([3-N,N-diethylaminophenyl]oxymethyl)benzophenone hydrazone, 4-([N-ethyl-N-phenyl-2-aminoethyl]oxymethyl)benzophenone hydrazone or 4,4'-bis-tert-butyl ester benzophenone hydrazone.

The ketone compounds of formula (IV):

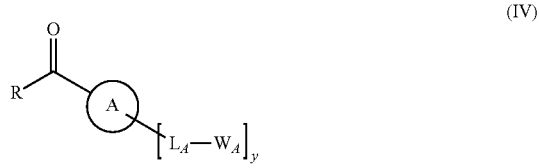

(IV)

in which R, A, $L_A$, $W_A$, and y are as defined above, may be prepared from commercially available starting materials using known synthetic procedures.

For example, many compounds of formula (IV) can be prepared by analogy with the syntheses outlined in the Examples for the ketone compounds 4-hydroxylmethyl benzophenone (3), 4-(allyloxymethyl)benzophenone (9) and 4-(Benzoyl benzyl)phosphonic acid diethyl ester (14). Each of those compounds was synthesised starting from 4-methyl benzophenone (1), which is commercially available. That compound was brominated to yield 4-bromomethyl benzophenone (2), which was subsequently converted into either 4-hydroxymethyl benzophenone (3) (by treatment of 2 with an aqueous solution of a base) or 4-(Benzoyl benzyl)phosphonic acid diethyl ester (14) (by treatment of 2 with triethyl phosphate). 4-(allyloxymethyl)benzophenone (9) was synthesised by treating 4-hydroxymethyl benzophenone (3) with sodium hydride and allyl bromide.

Many other ketone compounds of formula (IV) in which A is phenyl and R is substituted or unsubstituted phenyl may be synthesised starting from benzophenone (which is commercially available) or from a substituted derivative of benzophenone. Many substituted derivatives of benzophenone are commercially available and/or easily synthesised using known methods. Examples of commercially available substituted benzophenone compounds are 2-hydroxybenzophenone, 4-hydroxybenzophenone, 3-bromobenzophenone, 4-bromobenzophenone, 2-cyanobenzophenone, 4-cyanobenzophenone, 2-aminobenzophenone, 3-nitrobenzophenone, 4-nitrobenzophenone, and 2-ethylbenzophenone. Thus, compounds of formula (IV) in which A is phenyl and R is a substituted phenyl group may be synthesised starting from the corresponding substituted benzophenone compound. Alternatively, the (substituted) benzophenone system could be synthesised using standard synthetic approaches, for example, by Friedel-Crafts reactions or variants and equivalents thereof, or by addition of an aromatic carbanion equivalent to an aldehyde followed by oxidation, or by oxidation of a suitable substituted diarylmethane.

The one or more $-L_A$-$W_A$ groups may be introduced by analogy with the syntheses of compounds 3, 9 and 14 in the Examples, or by any other suitable synthetic procedure. For example, one or more suitable leaving groups may be introduced at the position(s) of a benzophenone or substituted benzophenone compound at which $-L_A$-$W_A$ substitution is desired. The leaving group may be a halo group, for example bromo. The leaving group may be introduced directly onto a phenyl ring of the benzophenone compound (e.g. as in 4-bromobenzophenone) or onto a phenyl ring substituent, such as an alkyl group (e.g. as in 4-methyl benzophenone). Following introduction of the one or more leaving groups, the leaving group(s) may be substituted by one or more $-L_A$-$W_A$ groups. Thus, for example, a bromo leaving group could be substituted by a hydroxyl group or a phosphonic acid ester group. Alternatively, one or more functional groups may be introduced at the position(s) of a benzophenone or substituted benzophenone compound at which $-L_A$-$W_A$ group(s) are desired. The functional group(s) may then be converted into the $-L_A$-$W_A$ group(s). For example, an aldehyde substituent on a phenyl ring may be treated with a phosphorus ylide (Wittig reaction) to yield a styryl group.

Where R is aryl or heteroaryl and one or more $-L_B$-$W_B$ groups are desired, these groups may be introduced by analogy with the synthetic methods used to introduce the one or more $-L_A$-$W_A$ groups.

Compounds of formula (IV) in which A or R is heteroaryl may be synthesised starting from ketone compounds which include a heteroaryl ring. Many ketone compounds including a heteroaryl ring are commercially available and/or easily synthesised. Examples of such commercially available compounds are 2-benzoylpyridine, di-2-pyridyl ketone and 2-benzoylthiophene.

Ketone compounds of formula (IV) in which R is other than aryl or heteroaryl may be synthesised starting from the appropriate ketone $R^B C(\!=\!O)R^A$, wherein $R^A$ is aryl or heteroaryl and $R^B$ is selected from hydrogen, $C_{1-10}$ alkoxy, aryloxy, di($C_{1-10}$)alkylamino, alkylarylamino, diarylamino, $C_{1-10}$ alkylthio, arylthio and $CR'_3$, wherein each R' is independently selected from a halogen atom, aryl, heteroaryl, $C_{3-7}$ cycloalkyl, $C_{5-7}$ heterocyclyl and $C_{1-6}$ alkyl, which $C_{1-4}$ alkyl is optionally interrupted by N(R"), O, S or arylene wherein R" is H, $C_{1-4}$ alkyl or aryl. Examples of such commercially available ketones include benzaldehyde, 2,2-Dimethylpropiophenone (i.e. tert-Butyl phenyl ketone) and 2,2,2-trifluoroacetophenone.

In the carbene precursor compounds of the invention, of formula (I), in the process of the invention for producing a carbene precursor compound of formula (I), and in the process of the invention for producing a compound of formula (III), $-L_A$-$W_A$ and, where present, $-L_A$-$W_B$, are typically other than —$NMe_2$.

Typically, $-L_A$-$W_A$ and, where present, $-L_A$-$W_B$, are other than —N=N—$Ar^P$, wherein $Ar^P$ is an unsubstituted or substituted phenyl group. Typically, $Ar^P$ is:

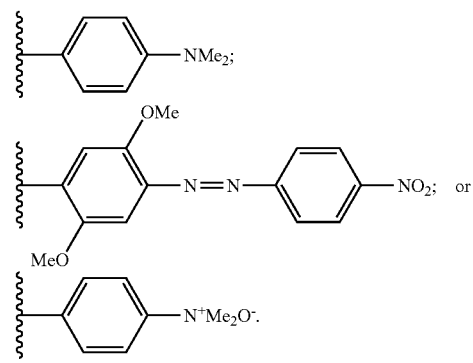

Typically, $-L_A$-$W_A$ and, where present, $-L_A$-$W_B$, are other than —$CH_2OR^{QQ}$ wherein $R^{QQ}$ is N-ethyl-N-phenyl-2-aminoethyl, 3,4-dimethoxyphenyl or 3-N,N-dimethylaminophenyl.

Typically, $-L_A-W_A$ and, where present, $-L_A-W_B$, are other than $-N^+Me_2O^-$.

Typically, $-L_A-W_A$ and, where present, $-L_A-W_B$, are other than $-CH_2O(CH_2)_2N(H)C(O)N(H)Ph$.

Typically, $-L_A-W_A$ and, where present, $-L_A-Ws$, are other than $-CH_2O(CH_2)_2N(Ph)CH_2CH_3$.

Typically, $-L_A-W_A$ and, where present, $-L_A-W_B$, are other than hydrogen.

More typically, $-L_A-W_A$ and, where present, $-L_A-W_B$, are other than each of the following moieties:
— $-CH_2OR^{QQ}$ wherein $R^{QQ}$ is N-ethyl-N-phenyl-2-aminoethyl, 3,4-dimethoxyphenyl or 3-N,N-dimethylaminophenyl;
— $-NMe_2$;
— $-N^+Me_2O^-$;
— $-CH_2O(CH_2)_2N(H)C(O)N(H)Ph$;
— $-CH_2O(CH_2)_2N(Ph)CH_2CH_3$; and
— $-N=N-Ar^P$, wherein $Ar^P$ is an unsubstituted or substituted phenyl group. Typically, $Ar^P$ is:

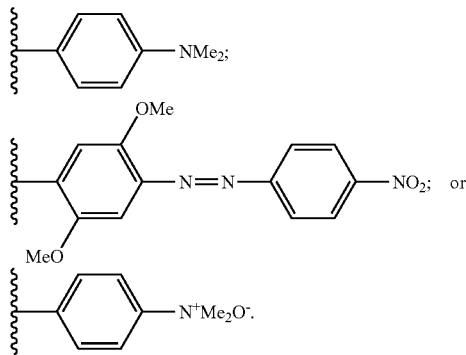

Typically, $-L_A-W_A$ and, where present, $-L_A-W_B$, are other than hydrogen and other than $Q^P$, wherein:

$Q^P$ is selected from $N(Z_1^P)(Z_2^P)$ and $CH_2-V^P-(W^P-R^P)_a$;

$Z_1^P$ and $Z_2^P$ are independently selected from aryl which is unsubstituted or substituted, heteroaryl which is unsubstituted or substituted, $C_{1-10}$ alkoxy which is unsubstituted or substituted, $C_{1-10}$ alkylamino which is unsubstituted or substituted, $di(C_{1-10})$alkylamino which is unsubstituted or substituted, $C_{1-10}$ alkylthio which is unsubstituted or substituted, and $C_{1-10}$ alkyl which is unsubstituted or substituted and which is optionally interrupted by $N(R^{2P})$, O or S wherein $R^{2P}$ is H or $C_{1-6}$ alkyl;

$V^P$ is $C_{1-10}$ alkylene, $-O-C_{1-10}$ alkylene-, $-C_{1-10}$ alkylene-$O-$ or $-O-C_{1-10}$ alkylene-$O-$;

$W^P$ is a functional group of one of the following formulae (a) to (c):

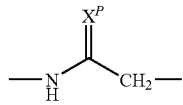
(a)

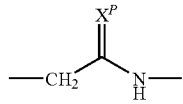
(b)

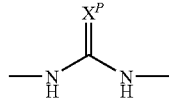
(c)

wherein $X^P$ is O, S or $NH_2^+$;

$R^P$ is selected from H, $C_{1-6}$ alkyl which is unsubstituted or substituted, aryl which is unsubstituted or substituted and heteroaryl which is unsubstituted or substituted; and a is 1, 2 or 3.

Typically, $-L_A-W_A$ and, where present, $-L_A-W_B$, are other than hydrogen and other than $-CH_2OR^Q$, wherein:

$R^Q$ is $Ar^{1Q}$ or $(CH_2)_b(NR^{1Q})(R^{2Q})$;

$Ar^{1Q}$ is:

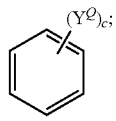

wherein $Y^Q$ is $C_{1-4}$ alkoxy or $NR^{3Q}NR^{4Q}$);

$R^{3Q}$ and $R^{4Q}$, which may be the same or different, are $C_{1-4}$ alkyl;

c is 0 or an integer of 1 to 3;

$R^{1Q}$ is $C_{1-4}$ alkyl;

$R^{2Q}$ is phenyl; and b is an integer of 1 to 4.

More typically, $-L_A-W_A$ and, where present, $-L_A-W_B$, are other than hydrogen and other than $Q^P$ and other than $-CH_2OR^Q$, wherein $Q^P$ and $R^Q$ are as defined above.

The present invention is further illustrated in the Examples which follow:

EXAMPLES

[4-(Diazo(phenyl)methyl)phenyl]methanol (5) and 7-Oxa-bicyclo[2.2.1]hept-5-ene-2-carboxylic acid-4-(diazophenylmethyl)-benzyl ester (7) were prepared and polymers were functionalised as shown in Scheme 1.

Scheme 1

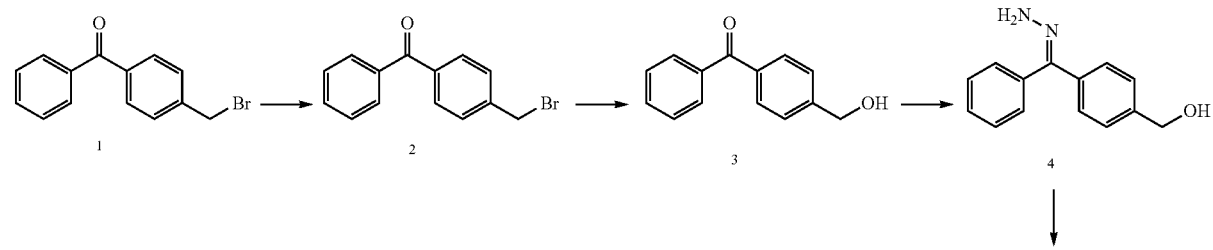

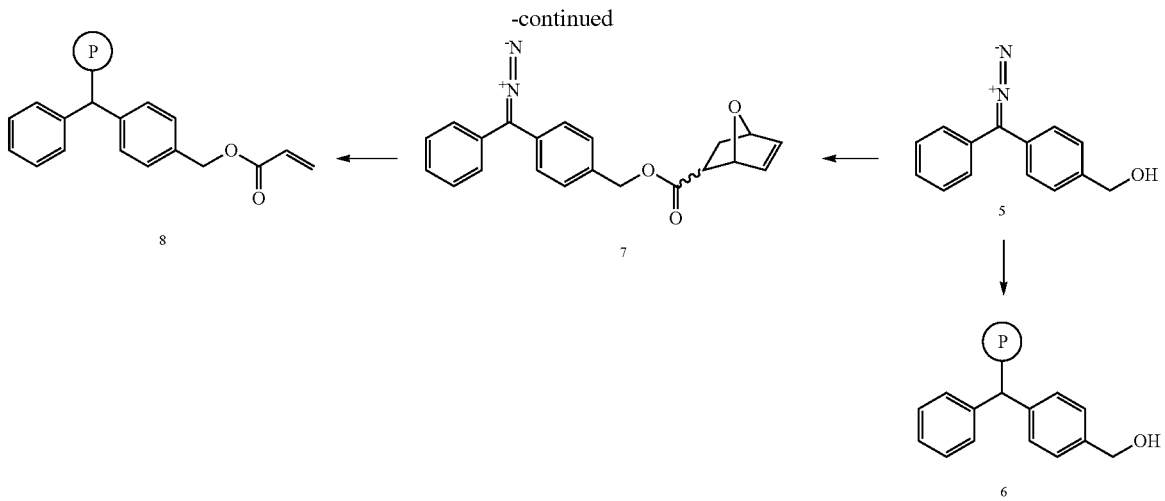

Reference Example 1

Preparation of 4-Bromomethyl benzophenone (2)

A stirred mixture of 4-methyl benzophenone (1) (15.0 g, 76 mmol) and N-bromo succinimide (14.2 g, 80 mmoll) in chloroform (100 ml) was heated to reflux for 18 h. with a 100W bulb shining 2 cm from the flask. The reaction mixture was cooled, washed with water and concentrated in vacuo. The resulting solid was washed with diethyl ether to leave 2 (15.1 g, 72%) as a white solid; $\delta_H$ (CDCl$_3$) 4.55 (2H, s, CH$_2$Br), 7.46-7.84 (9H, m, Ar—H).

Reference Example 2

Preparation of 4-Hydroxylmethyl benzophenone (3)

To a suspension of 2 (6.0 g, 22 mmol) in a mixture of 1,4 dioxane (60 ml) and water (60 ml) was added calcium carbonate (10.8 g, 110 mmol). The mixture was heated to reflux for 18 h, concentrated in vacuo and the residue portioned between DCM and water. The organic layer was collected, dried over MgSO$_4$, concentrated in vacuo then recrystalised from diethyl ether to furnish 3 (4.1 g, 89%) as a white solid; M.P. 59-61° C. (Lit 61-64° C.); $\delta_H$ (CDCl$_3$) 3.14 (s, 1H, CH$_2$OH), 4.75 (s, 2H, CH$_2$OH), 7.41-7.49 (m, 4H, 3-, 3'-, 5-, 5'-H), 7.54-7.58 (m, 1H, 4'-H), 7.72-7.76 (m, 4H, 2-, 2'-, 6-, 6'-H) ppm; $\delta_C$ (CDCl$_3$) 64.4 (CH$_2$OH), 126.4 (3'-, 5'-C), 128.3 (3-, 5-C), 130.0, 130.4 (2-, 2'-, 6-, 6'-C), 132.5 (4'-C), 136.4, 137.5 (1-, 1'-C), 140.0 (4-C), 196.9 (Ar$_2$C=O) ppm; $v_{max}$ (thin film) 3406, 3058, 2921, 1655, 1279 cm$^{-1}$; m/z (ES) 211 ([M–H]$^-$ 100%), 183 (45%).

Example 1

Preparation of [4-(Diazo(phenyl)methyl)phenyl]methanol (5)

4-Hydroxymethyl benzophenone hydrazone (4)

4-Bromomethyl benzophenone (2) was prepared as described in Reference Example 1. 4-Bromomethyl benzophenone (2) was converted into 4-Hydroxylmethyl benzophenone (3) as described in Reference Example 2. To solution of 3 (2.5 g, 12 mmol) in ethanol (20 ml) was added hydrazine hydrate (2.9 g 59 mmol). The mixture was heated to reflux for 24 h. then concentrated in vacuo. The residue was portioned between DCM and water and the organic layer collected and concentrated to yield 4 (2.6 g, 98%) a mixture of cis and trans isomers and as a yellow semi solid; $\delta_H$ (CDCl$_3$) 2.84, 3.09 (2×bs, 1H, OH), 4.51, 4.61 (2×s, 2H, CH$_2$OH), 5.32 (bs, 2H, NNH$_2$), 7.13-7.17 (m, 4H, 3-, 3'-, 5-, 5'-H), 7.30-7.43 (m, 5H, 2-, 2'-, 4'-, 6-, 6'-H) ppm; $\delta_C$ (CDCl$_3$) 64.4, 64.6 (2×CH$_2$OH), 126.4, 126.6, 127.7, 128.0, 128.1, 128.6, 128.8, 128.9, 129.3 (Ar—C), 131.8, 132.7 (2×1'-C), 137.5, 138.2 (2×1-C), 141.0, 141.8 (2×4'-C), 149.2 (C=N) ppm; $v_{max}$ (thin film) 3384, 2870, 1583, 1444, 1412, 1015 cm$^{-1}$; found (ES) 227.1180, C$_{14}$H$_{15}$N$_2$O requires 227.1179.

[4-(Diazo(phenyl)methyl)phenyl]methanol (5)

To a mixture of mercury (II) oxide (2.9 g, 13 mmol), sodium sulphate (2.2 g, 15 mmol) and sat potassium hydroxide in ethanol (4 ml) was added a solution of 4 (2.6 g, 11 mmol) in dry THF (20 ml). The mixture was stirred in the dark for 2 h. then filtered through a celite pad. Concentration of the filtrate in vacuo yielded 5 (2.4 g, 100%) as a dark red oil; $\delta_H$ (CDCl$_3$) 4.69 (s, 2H, CH$_2$OH), 7.29-7.31 (m, 4H, 3-, 3'-, 5-, 5'-H), 7.39-7.41 (m, 5H, 2-, 2'-, 4'-, 6-, 6'-H) ppm; $\delta_C$ (CDCl$_3$) 64.8 (CH$_2$OH), 125.1, 125.2 (3-, 3'-, 5-, 5'-C), 125.6 (4'-C), 127.9, 129.1 (2-, 2'-, 6-, 6'-C), 128.9, 129.4 (1-, 1'-C), 138.2 (4-C) ppm; $v_{max}$ (thin film) 3346, 2872, 2038, 1511, 1493 cm$^{-1}$; m/z (FI4) 224 ([M]$^+$, 100%); found (FT) 224.0949, C$_{14}$H$_{12}$N$_2$O requires 224.0950.

Example 2

Preparation of hydroxy polymer (6)

[4-(Diazo(phenyl)methyl)phenyl]methanol (5) was prepared as described in Example 1. A solution of 5 in THF was coated onto the polymer and to heated to 120° C. for 10 mins, then washed with acetone to yield the hydroxyl functionalised polymer 6.

Example 3

Preparation of 7-Oxa-bicyclo[2.2.1]hept-5-ene-2-carboxylic acid-4-(diazo-phenylmethyl)-benzyl ester (7)

[4-(Diazo(phenyl)methyl)phenyl]methanol (5) was prepared as described in Example 1. To a solution of 5 (5 g, 22 mmol) in dry toluene (50 ml) and dry triethylamine (6.7 g, 66 mmol) at 0° C. was added a solution of 7-oxabicyclo[2.2.1]heptane-2-carbonyl chloride (7.0 g, 44 mmol) in dry toluene. The mixture was stirred at 0° C. for 2 h. then quenched with sat. aqueous sodium carbonate (50 ml). The organic layer was separated and dried over MgSO$_4$ to yield 7 as a red solution in toluene.

Example 4

Preparation of acrylate polymer (8)

7-Oxa-bicyclo[2.2.1]hept-5-ene-2-carboxylic acid-4-(diazo-phenylmethyl)-benzyl ester (7) was prepared as described in Example 3. A solution of 7 in toluene was coated onto the polymer and heated to 120° C. for 15 mins, then washed with acetone to yield the acrylate functionalised polymer 8.

1-(allyloxymethyl)-4-(diazo(phenyl)methyl)benzene (11) was prepared and polymers were functionalised as shown in Scheme 2.

$OCH_2CH=CHH$), 5.34 (ddt 1H, J=1.4, 3.2, 17.3 Hz, $OCH_2CH=CHH$), 5.88-6.08 (m, 1H, $OCH_2CH=CHH$), 7.42-7.50 (m, 4H, 3-, 3'-, 5-, 5'-H), 7.54-7.62 (m, 1H, 4'-H), 7.78-7.82 (m, 4H, 2-, 2'-, 6-, 6'-H) ppm; $\delta_C$ (CDCl$_3$) 61.4, 71.3 (ArCH$_2$O, OCH$_2$CH=CH$_2$), 117.3 (OCH$_2$CH=CH$_2$), 127.0, 128.1 (3-, 3'-, 5-, 5'-C), 129.8, 130.1 (2-, 2'-, 6-, 6'-C), 132.2 (4'-C), 134.3 (OCH$_2$CH=CH$_2$), 136.6, 137.5 (1-, 1'-C), 143.1 (4-C), 196.2 (C=O) ppm; $\nu_{max}$ (thin film) 3061, 2855, 1658, 1609, 1447, 1412, 1278, 1089, 924 cm$^{-1}$; m/z (Er) 252 ([M$^+$], 85%), 222 (100%); found 252.1158, C$_{17}$H$_{16}$O$_2$ requires 252.1150.

[(4-(Allyloxylmethyl)phenyl)(phenyl)methylene]hydrazine (10)

To solution of 9 (1.09 g, 43 mmol) in methanol (10 ml) was added hydrazine hydrate (1.08 g 20 mmol). The mixture was heated to reflux for 48 h. then concentrated in vacuo. The residue was partioned between DCM and water and the organic layer collected and concentrated to yield 10 (1.10 g, 98%) as a mixture of cis and trans isomers and as a yellow oil;

Scheme 2

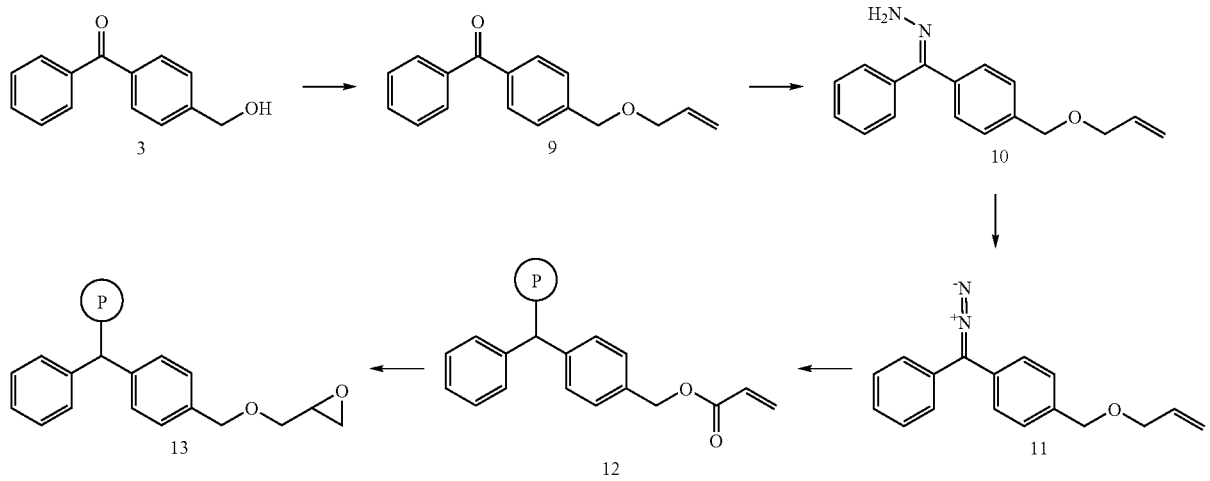

Example 5

Preparation of 1-(allyloxymethyl)-4-(diazo(phenyl)methyl)benzene (11)

4-(Allyloxymethyl)benzophenone (9)

4-Bromomethyl benzophenone (2) was prepared as described in Reference Example 1. 4-Bromomethyl benzophenone (2) was converted into 4-Hydroxylmethyl benzophenone (3) as described in Reference Example 2. To a solution of 3 (0.5 g, 3.4 mmol) in dry THF (10 ml) was added sodium hydride (0.3 g, 60% dispersion in mineral oil, 6.7 mmol). The mixture was stirred for 5 min, then allyl bromide (0.8 g, 6.7 mmol) was added. The mixture as stirred for 18 h. the quenched with water and concentrated in vacuo. The residue was portioned between DCM and water, the organic layer collected, dried over MgSO$_4$ and concentrated. A mineral oil impurity was removed using a silica plug eluting with petrol then ethyl acetate to yield 9 (0.6 g, 92%) as a yellow oil; $\delta_H$ (CDCl$_3$) 4.08 (dt, 2H, J=1.4, 5.5 Hz, OCH$_2$CH=CH$_2$), 4.60 (s, 2H, ArCH$_2$O), 5.24 (ddt 1H, J=1.4, 3.2, 10.3 Hz, $\delta_H$ (CDCl$_3$) 4.03, 4.13 (2×dt, 2H, J=1.4, 5.6 Hz, OCH$_2$CH=CH$_2$) 4.52, 4.60 (2×s, 2H, ArCH$_2$O), 5.20, 5.27 (ddd, 1H, J=1.4, 3.0, 10.4 Hz, OCH$_2$CH=CHH), 5.32, 5.37 (ddd, 1H, J=1.4, 3.2, 17.3 Hz, OCH$_2$CH=CHH), 5.45 (bs, 2H, NNH$_2$), 5.91-6.06 (m, 1H, OCH$_2$CH=CH$_2$), 7.28-7.31 (m, 4H, 3-, 3'-, 5-, 5'-H), 7.46-7.55 (m, 5H, 2-, 2'-, 4'-, 6-, 6'-H) ppm; $\delta_C$ (CDCl$_3$) 60.1, 71.5, 71.7 (ArCH$_2$O, OCH$_2$CH=CH$_2$), 117.0, 117.3 (OCH$_2$CH=CH$_2$), 126.3, 126.4, 127.4, 128.0, 128.5, 128.7, 129.3 (Ar—C), 134.4, 134.6 (2×OCH$_2$CH=CH$_2$), 137.7, 138.1, 139.1 (Ar—C), 148.7 (C=N) ppm; $\nu_{max}$ (thin film) 3404, 3289, 3057, 2855, 1612, 1444, 1411, 1277, 1083 cm$^{-1}$; m/z (ES$^+$) 267 ([M+H]$^+$, 100%); found (ES$^+$) 267.1492, C$_{17}$H$_{19}$N$_2$O requires 267.1492.

1-(allyloxymethyl)-4-(diazo(phenyl)methyl)benzene (11)

To a mixture of mercury (II) oxide (3.1 g, 14 mmol), sodium sulphate (2.4 g, 16 mmol) and sat potassium hydroxide in ethanol (3 ml) was added a solution of 10 (3.2 g, 12 mmol) in dry TIM (20 ml). The mixture was stirred in the dark for 2 h. then filtered through a celite pad. Concentration of the filtrate in vacuo yielded 11 (3.1 g, 100%) as a dark red oil; δ$_H$ (CDCl$_3$) 3.90-3.94 (m, 2H, OCH$_2$CH=CH$_2$), 4.38 (s, 2H, ArCH$_2$O), 5.05-5.26 (m, 2H, OCH$_2$CH=CH$_2$), 5.74-5.94 (m, 1H, OCH$_2$CH=CH$_2$), 7.12-7.36 (m, 9H, Ar—H) ppm;

chloroperbenzoic acid in DCM. The polymer was soaked for 20 h. then filtered and washed with DCM and water to yield the epoxide functionalised polymer 13.

[4-(Diazo-phenyl-methyl)-benzyl]phosphonic acid diethyl ester (16) was prepared and polymers were functionalised as shown in Scheme 3.

Scheme 3

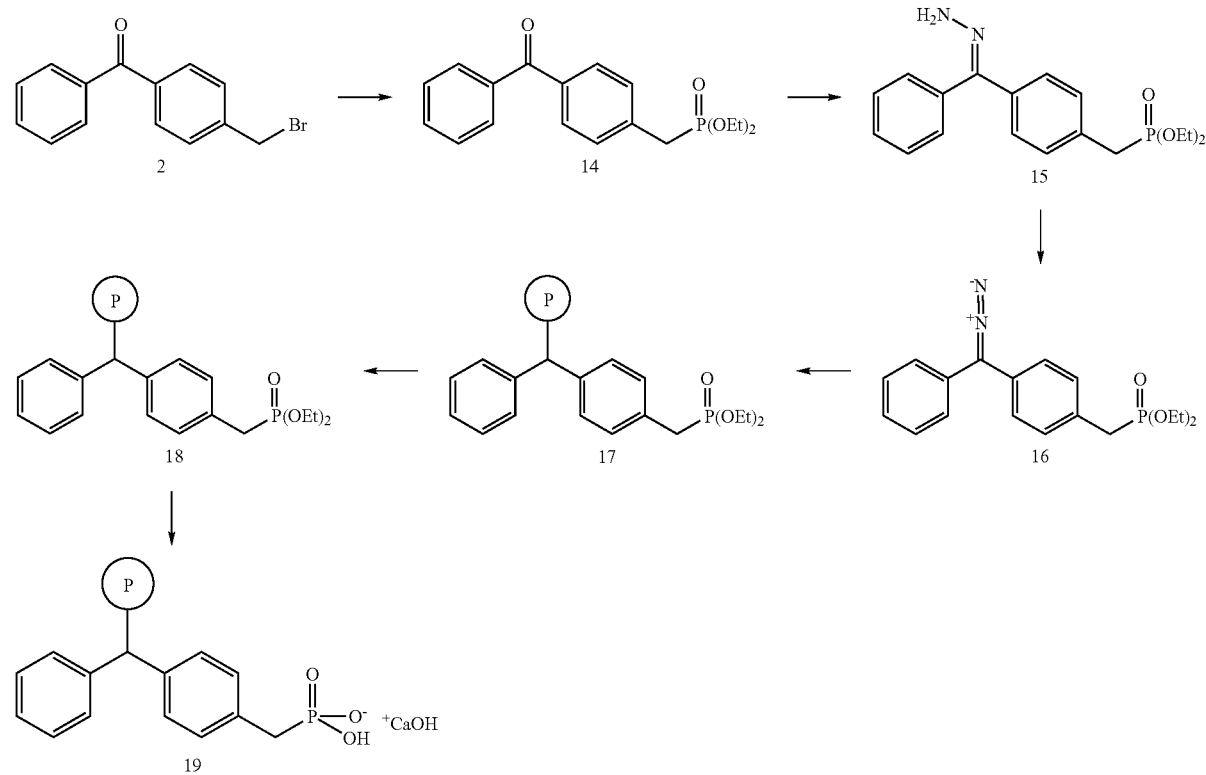

δ$_C$ 71.0, 71.6 (OCH$_2$CH=CH$_2$, ArCH$_2$O), 117.0 (OCH$_2$CH=CH$_2$), 124.9, 125.0, 125.4, 128.5, 129.0 (Ar—C), 129.8, 130.1 (1-, 1'-C), 134.5 (OCH$_2$CH=CH$_2$), 135.6 (4-C) ppm; ν$_{max}$ (thin film) 3029, 2855, 2038, 1596, 1512, 1494, 1085 cm$^{-1}$; m/z (Fr) 264 ([M]$^+$, 70%), 252 (100%), 196 (35%); found (Fr) 264.1250, C$_{17}$H$_{16}$N$_2$O requires 264.1263.

Example 6

Preparation of olefin polymer (12)

1-(allyloxymethyl)-4-(diazo(phenyl)methyl)benzene (11) was prepared as described in Example 5. A solution of 11 in THF was coated onto the polymer and heated to 120° C. for 15 mins, then washed with acetone to yield the olefin functionalised polymer 12.

Example 7

Preparation of epoxide polymer (13)

Olefin functionalised polymer 12 was prepared as described in Example 6. To a flask containing the olefin functionalised polymer 12 was added a solution of meta- Example 8

Preparation of [4-(Diazo-phenyl-methyl)-benzyl]phosphonic acid diethyl ester (16)

4-(Benzoyl benzyl)phosphonic acid diethyl ester (14)

4-Bromomethyl benzophenone (2) was prepared as described in Reference Example 1. A solution of 2 (7.8 g, 28 mmol) in triethyl phosphite (20 ml) was heated to reflux for 4 h. then concentrated in vacuo. The residue was purified by flash chromatography on silica gel eluting with 65% ethyl acetate: petrol to yield 14 (8.1 g, 86%) as a pale yellow oil; 8H (CDCl$_3$) 1.24 (6H, dt, J$_{H-H}$=7.1 Hz, J$_{H-P}$=3.6 Hz, 2×CH$_2$CH$_3$), 3.22 (2H, d, J$_{H-P}$=22.1 Hz, ArCH$_2$P), 4.04 (4H, q, J$_{H-H, H-P}$=7.1 Hz, 2×CH$_2$CH$_3$), 7.47-7.78 (9H, m, Ar—H) ppm; δ$_C$(CDCl$_3$) 16.4 (d, J$_{C-P}$=4.9 Hz, 2×CH$_2$CH$_3$), 33.9 (d, J$_{C-P}$=137.5 Hz, ArCH$_2$P), 62.3 (d, J$_{C-P}$=7.0 Hz, 2×CH$_2$CH$_3$), 128.3 and 129.7 (3-, 5-, 3'-, 5'-C), 130.3 and 132.3 (2-, 6-, 2'-, 6'-C), 132.4 (4'-C), 136.1 and 136.7 (1-, 1'-C), 137.5 (4-C), 196.2 (Ar$_2$CO) ppm; δ$_P$ (CDCl$_3$) 26.47 ppm; ν$_{max}$ (thin film) 2984 (C—H$_{st}$), 1657 (C=O$_{st}$), 1278

(P=O$_{st}$), 1026 (P—O$_{st}$) cm$^{-1}$; m/z (ES) 333 ([M+H]$^+$5%), 355 ([M+Na]$^+$10%), 391 ([M+NH$_4$+MeCN]$^+$100%), 687 ([M2+Na]$^+$ 30%).

[4-(Hydrazono-phenyl-methyl)-benzyl]phosphonic acid diethyl ester (15)

To solution of 14 (2.2 g, 6.6 mmol) in methanol (20 ml) was added hydrazine hydrate (10 ml). The mixture was heated to reflux for 6 h. then concentrated in vacuo. The residue was portioned between DCM and water and the organic layer collected and concentrated to yield 15 (2.3 g, 100%) as a mixture of cis and trans isomers and as a yellow oil; $\delta_H$ (CDCl$_3$) 1.23 (6H, dt, J$_{H-H}$=7.1 Hz, J$_{H-P}$=3.0 Hz, 2×CH$_2$CH$_3$), 1.27 (6H, dt, J$_{H-H}$=7.1 Hz, J$_{H-P}$=3.0 Hz, 2×CH$_2$CH$_3$'), 3.12 (2H, d, J$_{H-P}$=17.6 Hz, ArCH$_2$P), 3.23 (2H, d, J$_{H-P}$=17.6 Hz, ArCH$_2$P'), 4.08 (4H, m, 2×CH$_2$CH$_3$), 5.44 (2H, bs, NH$_2$), 7.47-7.78 (9H, m, Ar—H) ppm; $\delta_C$ (CDCl$_3$) 16.3 (d, J$_{C-P}$=6.0 Hz, 2×CH$_2$CH$_3$), 16.4 (d, J$_{C-P}$=6.2 Hz, 2×CH$_2$CH$_3$'), 33.4 (d, J$_{C-P}$=137.9 Hz, ArCH$_2$P), 33.4 (d, J$_{C-P}$= 138.9 Hz, ArCH$_2$P'), 62.1 (m, 2×CH$_2$CH$_3$), 126.4-138.4 (Ar—C), 148.3 and 148.4 (Ar$_2$CNNH$_2$) ppm; $\delta_P$ (CDCl$_3$) 26.04, 26.26 ppm; $\nu_{max}$ (thin film) 3387 (N—H$_{st}$), 2983 (C—H$_{st}$), 1611 (C=N$_{st}$), 1234 (P=O$_{st}$), 1023 (P—O$_{st}$); m/z (ES$^+$) 347.16 ([M+H]$^+$60%), 26919 ([M+Na]$^+$ 60%), 405.28 ([M+NH$_4$+MeCN]$^+$100%); found (ES) 347.1541, C$_{18}$H$_{24}$N$_2$O$_3$P requires 347.1525.

[4-(Diazo-phenyl-methyl)-benzyl]phosphonic acid diethyl ester (16)

To a mixture of mercury (II) oxide (0.21 g, 0.97 mmol), sodium sulphate (0.16 g, 1.1 mmol) and sat potassium hydroxide in ethanol (0.2 ml) was added a solution of 15 (0.28 g, 0.81 mmol) in dry THF (20 ml). The mixture was stirred in the dark for 1 h. the filtered through a celite pad. Concentration of the filtrate in vacuo yielded 16 (0.25 g, 89%) as a dark red oil; $\delta_H$ (CDCl$_3$) 1.28 (6H, d, J$_{H-H}$=7.1 Hz, 2×CH$_2$CH$_3$), 3.16 (2H, d, J$_{H-P}$=21.7 Hz, ArCH$_2$P), 3.98-4.13 (4H, m, 2×CH$_2$CH$_3$), 7.15-7.43 (9H, m, Ar—H) ppm; $\delta_C$ (CDCl$_3$) 16.4 (d, J$_{C-P}$=6.0 Hz, 2×CH$_2$CH$_3$), 33.3 (d, J$_{C-P}$=138.2 Hz, ArCH$_2$P), 62.1 (d, J$_{C-P}$=6.8 Hz, 2×CH$_2$CH$_3$), 125.1, 125.2, 125.2, 125.6, 129.1 (Ar—C), 129.4 (4-C), 130.4 and 130.5 (1-, 1'-C) ppm; $\delta_P$ (CDCl$_3$) 26.37 ppm; $\nu_{max}$ (thin film) 2982 (C—H$_{st}$), 2039 (C=N=N$_{st}$), 1248 (P=O$_{st}$), 1027 (P—O$_{st}$) cm$^{-1}$; m/z (ES$^+$) 403 ([M+NH$_4$+MeCN]$^+$100%); found (FI$^+$) 344.1778, C$_{18}$H$_{21}$N$_2$O$_3$P requires 344.1290.

Example 9

Preparation of phosphonate ester polymer (17)

[4-(Diazo-phenyl-methyl)-benzyl]phosphonic acid diethyl ester (16) was prepared as described in Example 8. A solution of 16 in DCM was coated onto the polymer and heated to 100° C. for 10 mins, then washed with DCM to yield the functionalised polymer 17.

Example 10

Preparation of phosphonic acid polymer (18)

Phosphonate ester polymer (17) was prepared as described in Example 9. To a flask containing the polymeric phosphonate ester 17 was added 1M hydrochloric acid. The mixture was stirred for 18 h., filtered and the polymer washed with water to yield polymeric phosphonic acid 18.

Example 11

Preparation of phosphonic acid calcium salt polymer (19)

Polymeric phosphonic acid 18 was immersed in an aqueous calcium hydroxide solution for 6 h., then washed with water to yield polymeric phosphonic acid calcium salt 19.

Example 12

Coating and Adhesion of 6 and 8

To a sample of treated polymer (6 or 8) was added the required coating. A second sheet of unfunctionalised polymer was placed on top and the laminate was flattened using a roller. The composite material was cured (using heat and/or light), the sheets separated and the coating tested for adhesion using a tape test and a cross hatch tape test.

TABLE 2

Tape Test and Cross Hatch Test results for 6 and 8

| Test | System | Coating | Conditions | Tape Test | Cross Hatch Test |
|---|---|---|---|---|---|
| 1 | 6 | Laromer 5000 | UVCure, then 140° C. 5 min | Pass | Pass |
| 2 | 6 | Cationic coating mixture 1 | UV Cure | Pass | Pass |
| 3 | 8 | Acrylate coating mixture 2 | UV Cure | Pass | Fail |

The last two tests (Tests 2 and 3) were repeated on blank material, and in both cases the result was a fail. Based on experienced, the first test (Test 1) would also have failed had it been repeated using blank material.

Description of the Tape Test:

The treated polymers were taped with a strip of adhesive tape. In each case the tape was secured by rubbing down with an appropriate smooth edged tool, and the strip was then rapidly pulled off. A "Pass" occurs when the top laminate layer remains fast.

Description of the Cross Hatch Test:

The treated polymers were scratched with a sharp blade in a series of "X" marks, and then taped with a strip of adhesive tape. In each case the tape was secured by rubbing down with an appropriate smooth edged tool, and the strip was then rapidly pulled off. A "Pass" occurs when the top laminate layer remains fast.

A full description of the Tape Test and Cross Hatch test is given in ASTM D3359, which describes a standard method for the application and performance of these tests.

Example 13

Biocompatibility Against MG63 Human Osteosarcoma Cell Line

AlamarBlue™ Proliferation Study:

Cells were seeded at 5×10$^3$ cells per 10×10 mm membrane and left to culture for a 2-week period. Within this period of in vitro culture, the AlamarBlue™ assay was performed at day 5, day 8 and day 13 time points. The study was carried out on unmodified Hybond-N polymer membrane (control), as well as on a Hybond-N membrane functionalised with phosphonic acid (18) and a Hybond-N membrane functionalised with phosphonic acid calcium salt (19). The results are shown in FIG. 1, in which the control is denoted "C", and in the following Table 3. The phosphonic acid-functionalised Hybond-N (18) was prepared as described in Examples 9 and 10, using a Hybond-N membrane as the polymer. The phosphonic acid calcium salt-functionalised Hybond-N (19) was prepared as described in Examples 9, 10 and 11 using a Hybond-N membrane as the polymer.

TABLE 3

Results of AlamarBlue ™ proliferation study on unmodified Hybond-N polymer (control) and modified Hybond-N polymer (18 and 19)

| Time/days | Control/(Average RFU value) | 18/(Average RFU value) | 19/(Average RFU value) |
|---|---|---|---|
| 5 | 1233.64 | 496.07 | 557.38 |
| 8 | 1962.44 | 1092.87 | 1961.33 |
| 13 | 3042.34 | 3288.06 | 3896.38 |

The invention claimed is:

1. A carbene precursor compound of the following formula (I):

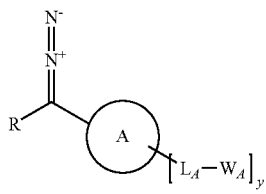

(I)

wherein:

A is an aryl or heteroaryl ring;

y is 1 or 2;

$L_A$ is -alk-, -arylene-, -alk-arylene-, -alk-X-arylene-, -alk-arylene-X-, or -alk-X-arylene-X-, wherein X is N(R"), O, or S and wherein alk is $C_{1-20}$ alkylene which is uninterrupted or interrupted by N(R"), O, S or arylene, wherein R" is H, $C_{1-6}$ alkyl or aryl;

$W_A$ is a group comprising an adhesive functional group or a group which is a precursor of an adhesive functional group, wherein $W_A$ is:

a group selected from: $-L^2-OH$, $-L^2-NH_2$, $-L^2-SH$, $C_{1-20}$ alkyl, $C_{3-20}$ cycloalkyl, $C_{3-20}$ heterocyclyl, aryl and heteroaryl, wherein said $C_{1-20}$ alkyl, $C_{3-20}$ cycloalkyl, $C_{3-20}$ heterocyclyl, aryl and heteroaryl are each substituted by $-L^2-OH$, $-L^2-NH_2$ or $-L^2-SH$, wherein said $C_{1-20}$ alkyl is uninterrupted or interrupted by N(R"), O, S or arylene, wherein R" is H, $C_{1-6}$ alkyl or aryl, and wherein $L^2$ is a single bond, $C_{1-6}$ alkylene, arylene, -arylene-$C_{1-6}$ alkylene- or -$C_{1-6}$ alkylene-arylene-, wherein each of said $C_{1-6}$ alkylene groups is uninterrupted or interrupted by N(R"), O, S or arylene;

a group which comprises a plurality of —OH, —NH$_2$ or —SH moieties;

a group which comprises at least one aliphatic carbon-carbon double bond;

a group which comprises at least one epoxide group;

a group which comprises one or more of any one of the following groups: a phosphonic acid group or a salt thereof, a sulfonic acid group or a salt thereof, a carboxylic acid group or a salt thereof, a sulfonamide group, and $C(O)NH_2$;

a group which comprises at least one group having the structure:

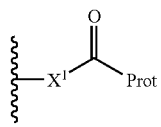

wherein $X^1$ is a single bond, C(R")(R'''), N(R") or O, wherein R" and R''' are independently selected from H, $C_{1-6}$ alkyl or aryl, and wherein Prot is a protecting group which is a precursor to a —CH=CH$_2$ group, wherein Prot is selected from 7-oxabicyclo[2.2.1]hept-2-yl, an organometallic group, and a 1,2-dioxygenated substrate; or a group which comprises $-P(=O)(OR^4)_2$ or

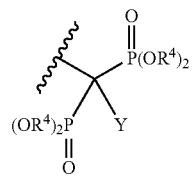

wherein $R^4$ is $C_{1-6}$ alkyl or aryl; and Y is H, $C_{1-6}$ alkyl, aryl, —OH, —SH or NH$_2$;

R is selected from aryl, heteroaryl and H;

provided that when R is aryl or heteroaryl, said aryl or heteroaryl may be unsubstituted or substituted by one or two groups, which groups are independently selected from $C_{1-6}$ alkyl, aryl, cyano, amino, keto, $C_{1-10}$ alkylamino, di($C_{1-10}$)alkylamino, arylamino, diarylamino, arylalkylamino, amido, hydroxy, halo, carboxy, ester, $C_{1-6}$ alkoxy, aryloxy, haloalkyl, thiol, $C_{1-10}$ alkylthio, arylthio, sulfonic acid, sulfonyl and -$L_B$-$W_B$, wherein $L_B$ is as defined above for $L_A$ and is the same as or different from $L_A$, and $W_B$ is as defined above for $W_A$ and is the same as or different from $W_A$.

2. A compound according to claim 1 wherein $W_A$ and $W_B$ are independently selected from:

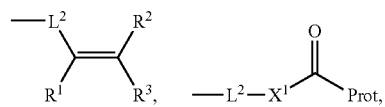

$-L^2$-OH, $-L^2$-NH$_2$, $-L^2$-SH, $-L^2$-M, $C_{1-20}$ alkyl, $C_{3-20}$ cycloalkyl, $C_{3-20}$ heterocyclyl, aryl and heteroaryl, wherein said $C_{1-20}$ alkyl, $C_{3-20}$ cycloalkyl, $C_{3-20}$ heterocyclyl, aryl and heteroaryl are each substituted by one or more groups selected from:

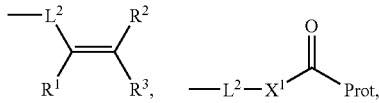

$-L^2$—OH, $-L^2$—NH$_2$, $-L^2$—SH and $-L^2$-M, and wherein said $C_{1-20}$ alkyl is uninterrupted or interrupted by N(R"), O, S or arylene, wherein R" is as defined in claim 1;

$X^1$ is a single bond, C(R")(R'"), N(R") or O, wherein R" is as defined in claim 1 and R'" is H, $C_{1-6}$ alkyl or aryl;

Prot is a protecting group which is a precursor to a —CH=CH$_2$ group, wherein Prot is selected from 7-oxabicyclo[2.2.1]hept-2-yl, an organometallic group, and a 1,2-dioxygenated substrate;

$L^2$ is a single bond, $C_{1-6}$ alkylene, arylene, -arylene-$C_{1-6}$ alkylene- or -$C_{1-6}$ alkylene -arylene-, wherein each of said $C_{1-6}$ alkylene groups is uninterrupted or interrupted by N(R"), O, S or arylene, wherein R" is as defined in claim 1, provided that when $L^2$ is a single bond the groups

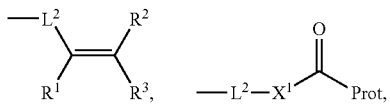

$-L^2$-OH, $-L^2$-NH$_2$ and $-L^2$—SH may not be bonded directly to X;

$R^1$, $R^2$ and $R^3$, which may be the same or different, are each selected from H, $C_{1-6}$ alkyl, aryl, cyano, amino, $C_{1-10}$ alkylamino, di($C_{1-10}$)alkylamino, arylamino, diarylamino, arylalkylamino, amido, halo, carboxy, ester, $C_{1-6}$ alkoxy, aryloxy, $C_{1-10}$ alkylthio and arylthio; and M is selected from a group that is capable of adhering to a metal, a metal alloy, or a metal salt, and a group which is a precursor of a group that is capable of adhering to a metal, metal alloy or a metal salt, wherein M is a group which comprises one or more of any one of the following groups: a phosphonic acid group or a salt thereof, a sulfonic acid group or a salt thereof, a carboxylic acid group or a salt thereof, a sulfonamide group, and C(O)NH$_2$, or wherein M is -P(=O)(OR$^4$)$_2$ or

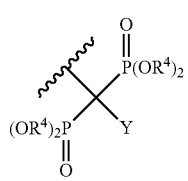

wherein R$^4$ is $C_{1-6}$ alkyl or aryl; and Y is H, $C_{1-6}$ alkyl, aryl, —OH, —SH or NH$_2$.

3. A compound according to claim 2 wherein M is selected from:
(a) P(=O)(OR$^4$)$_2$;

(b) 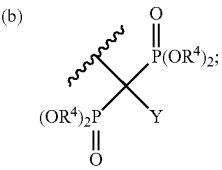

(c) —C(=O)OH;
(d) —CY(COOH)$_2$;
(e) —S(=O)$_2$OH;
(f) —CY[S(=O)$_2$OH]$_2$;
(g) —C(=O)NH$_2$;
(h) —CY[C(=O)NH$_2$]$_2$;
(i) —S(=O)$_2$NH$_2$; and
(j) —CY[S(=O)$_2$NH$_2$]$_2$, wherein R$^4$ is $C_{1-6}$ alkyl or aryl; and Y is H, $C_{1-6}$ alkyl, aryl, —OH, —SH or NH$_2$.

4. A compound according to claim 1, which compound is selected from:
[4-(Diazo(phenyl)methyl)phenyl]methanol, 7-Oxa-bicyclo[2.2.1]hept-5-ene-2-carboxylic acid-4-(diazo-phenylmethyl)-benzyl ester, 1-(allyloxymethyl)-4-(diazo(phenyl)methyl)benzene and [4-(Diazo-phenyl-methyl)-benzyl] phosphonic acid diethyl ester.

5. A compound according to claim 1 wherein said group which comprises a plurality of —OH, —NH$_2$ or —SH moieties is a polyol, a polythiol, a group containing a plurality of amino groups, or a group of the following structure:

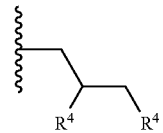

in which each R$^4$, which may be the same or different, is OH, NH$_2$ or SH.

6. A compound according to claim 1 wherein R is aryl or heteroaryl, which aryl or heteroaryl is unsubstituted or substituted by one or two groups, which groups are independently selected from $C_{1-6}$ alkyl, aryl, cyano, amino, keto, $C_{1-10}$ alkylamino, di($C_{1-10}$)alkylamino, arylamino, diarylamino, arylalkylamino, amido, hydroxy, halo, carboxy, ester, $C_{1-6}$ alkoxy, aryloxy, haloalkyl, thiol, $C_{1-10}$ alkylthio, arylthio, sulfonic acid, sulfonyl and -L$_B$-W$_B$, wherein L$_B$ and W$_B$ are as defined in claim 1.

7. A compound according to claim 1 wherein:
L$_A$ is $C_{1-20}$ alkylene which is substituted or unsubstituted and uninterrupted or interrupted by N(R"), O, S or arylene, wherein R" is H, $C_{1-6}$ alkyl or aryl; and
R is aryl or heteroaryl, which aryl or heteroaryl is unsubstituted or substituted by one or two groups, which groups are independently selected from $C_{1-6}$ alkyl, aryl, cyano, amino, keto, $C_{1-10}$ alkylamino, di($C_{1-10}$)alkylamino, arylamino, diarylamino, arylalkylamino, amido, hydroxy, halo, carboxy, ester, $C_{1-6}$ alkoxy, aryloxy, haloalkyl, thiol, $C_{1-10}$ alkylthio, arylthio, sulfonic acid, sulfonyl and -L$_B$-W$_B$, wherein L$_B$ is as defined above for L$_A$ and is the same as or different from L$_A$, and wherein W$_B$ is as defined in claim 1.

8. A compound according to claim 1 wherein:
$L_A$ is $C_{1-20}$ alkylene which is substituted or unsubstituted and uninterrupted or interrupted by N(R"), O, S or arylene, wherein R" is H, $C_{1-6}$ alkyl or aryl;
y is 1; and
R is aryl or heteroaryl, which aryl or heteroaryl is unsubstituted or substituted by one group, which group is selected from $C_{1-6}$ alkyl, aryl, cyano, amino, keto, $C_{1-10}$ alkylamino, di($C_{1-10}$) alkylamino, arylamino, diarylamino, arylalkylamino, amido, hydroxy, halo, carboxy, ester, $C_{1-10}$) 6alkoxy, aryloxy, haloalkyl, thiol, $C_{1-10}$ alkylthio, arylthio, sulfonic acid, sulfonyl and -$L_B$-$W_B$, wherein $L_B$ is as defined above for $L_A$ and is the same as or different from $L_A$, and wherein $W_B$ is as defined in claim 1.

9. A compound according to claim 1 wherein:
$L_A$ is $C_{1-20}$ alkylene which is substituted or unsubstituted and uninterrupted or interrupted by N(R"), O, S or arylene, wherein R" is H, $C_{1-6}$ alkyl or aryl;
A is an aryl ring;
y is 1; and
R is aryl, which aryl is unsubstituted or substituted by one group, which group is selected from $C_{1-6}$ alkyl, aryl, cyano, amino, keto, $C_{1-10}$ alkylamino, di($C_{1-10}$)alkylamino, arylamino, diarylamino, arylalkylamino, amido, hydroxy, halo, carboxy, ester, $C_{1-6}$ alkoxy, aryloxy, haloalkyl, thiol, $C_{1-10}$ alkylthio, arylthio, sulfonic acid, sulfonyl and -$L_B$-$W_B$, wherein $L_B$ is as defined above for $L_A$ and is the same as or different from $L_A$, and wherein $W_B$ is as defined in claim 1.

10. A compound according to claim 1 wherein:
$L_A$ is $C_{1-20}$ alkylene which is substituted or unsubstituted and uninterrupted or interrupted by N(R"), O, S or arylene, wherein R" is H, $C_{1-6}$ alkyl or aryl; and
R is aryl or heteroaryl, which aryl or heteroaryl is unsubstituted.

11. A compound according to claim 1 wherein:
$L_A$ is $C_{1-20}$ alkylene which is substituted or unsubstituted and uninterrupted or interrupted by N(R"), O, S or arylene, wherein R" is H, $C_{1-6}$ alkyl or aryl;
A is an aryl ring;
y is 1; and
R is aryl, which aryl is unsubstituted.

12. A compound according to claim 1 wherein:
$L_A$ is $C_{1-20}$ alkylene which is substituted or unsubstituted and uninterrupted or interrupted by N(R"), O, S or arylene, wherein R" is H, $C_{1-6}$ alkyl or aryl;
A is phenyl;
y is 1; and
R is phenyl, which phenyl is unsubstituted or substituted by one group, which group is selected from $C_{1-6}$ alkyl, aryl, cyano, amino, keto, $C_{1-10}$ alkylamino, di($C_{1-10}$)alkylamino, arylamino, diarylamino, arylalkylamino, amido, hydroxy, halo, carboxy, ester, $C_{1-6}$ alkoxy, aryloxy, haloalkyl, thiol, $C_{1-10}$ alkylthio, arylthio, sulfonic acid, sulfonyl and -$L_B$-$W_B$, wherein $L_B$ is as defined above for $L_A$ and is the same as or different from $L_A$, and wherein $W_B$ is as defined in claim 1.

13. A compound according to claim 1 wherein:
$L_A$ is $C_{1-6}$ alkylene which is uninterrupted or interrupted by O;
A is phenyl;
y is 1; and
R is phenyl, which phenyl is unsubstituted or substituted by one group, which group is selected from $C_{1-6}$ alkyl, aryl, cyano, amino, keto, $C_{1-10}$ alkylamino, di($C_{1-10}$)alkylamino, arylamino, diarylamino, arylalkylamino, amido, hydroxy, halo, carboxy, ester, $C_{1-6}$ alkoxy, aryloxy, haloalkyl, thiol, $C_{1-10}$ alkylthio, arylthio, sulfonic acid, sulfonyl and -$L_B$-$W_B$, wherein $L_B$ is as defined above for $L_A$ and is the same as or different from $L_A$, and wherein $W_B$ is as defined in claim 1.

14. A compound according to claim 1 wherein:
$L_A$ is $C_{1-6}$ alkylene which is uninterrupted or interrupted by O;
A is phenyl;
y is 1; and
R is unsubstituted phenyl.

15. A process for producing a substrate having a functionalised surface, which process comprises:
(a) contacting the substrate with a carbene precursor, which carbene precursor is a compound as defined in claim 1; and
(b) generating a carbene reactive intermediate from the carbene precursor so that it reacts with the substrate to functionalise the surface, thereby yielding said substrate having a functionalised surface.

16. A process according to claim 15 wherein the carbene precursor is a compound selected from:
[4-(Diazo(phenyl)methyl)phenyl]methanol, 7-Oxa-bicyclo[2.2.1]hept-5-ene-2-carboxylic acid-4-(diazo-phenylmethyl)-benzyl ester, 1-(allyloxymethyl)-4-(diazo(phenyl)methyl)benzene and [4-(Diazo-phenylmethyl)-benzyl] phosphonic acid diethyl ester.

17. A process according to claim 15 wherein the substrate comprises a polymer, an inorganic material, a pigment, a nanoparticle, a microparticle, textile, paper, a thermoplastic resin or a thermosetting resin.

18. A process according to claim 17 wherein the polymer is selected from polyolefins, polyesters, epoxy resins, polyacrylates, polyacrylics, polyamides, polyimides, polystyrenics, polytetrafluoroethylene, polyglycosides, polypeptides, polycarbonates, polyethers, polyketones, rubbers, polysulfones, polyurethanes, polyvinyls, cellulose and block copolymers, and wherein the nanoparticle is $C_{60}$ or a nanotube, and wherein the inorganic material is selected from silica, alumina, titania, glass, an allotrope of carbon, a metal salt, a metal other than an alkali metal or an alkaline earth metal, and an alloy of a metal other than an alkali metal or an alkaline earth metal.

19. A process according to claim 15 which further comprises:
contacting the functionalised surface of said substrate, or a part thereof, with an adherend, under conditions which cause adhesion of said substrate to said adherend.

20. A process according to claim 19 wherein wherein the adherend comprises a polymer, an inorganic material, a pigment, a nanoparticle, a microparticle, a textile, paper, a thermoplastic resin, a thermosetting resin, a biological cell or biological tissue.

21. A process according to claim 20 wherein the polymer is selected from polyolefins, polyesters, epoxy resins, polyacrylates, polyacrylics, polyamides, polyimides, polystyrenics, polytetrafluoroethylene, polyglycosides, polypeptides, polycarbonates, polyethers, polyketones, rubbers, polysulfones, polyurethanes, polyvinyls, cellulose and block copolymers, and wherein the nanoparticle is $C_{60}$ or a nanotube, and wherein the inorganic material is selected from silica, alumina, titania, glass, an allotrope of carbon, a metal salt, a metal other than an alkali metal or an alkaline earth metal, or an alloy of a metal other than an alkali metal or an alkaline earth metal.

* * * * *